US012679894B2

(12) United States Patent
Gibson et al.

(10) Patent No.: US 12,679,894 B2
(45) Date of Patent: ***Jul. 14, 2026

(54) ANTI-MICA/B ANTIBODIES THAT BLOCK MICA/B SHEDDING AND METHODS OF USE

(71) Applicant: Cullinan Mica Corp, Cambridge, MA (US)

(72) Inventors: Neil Gibson, Cambridge, MA (US); Justin Chapman, Cambridge, MA (US); Xin Du, Cambridge, MA (US)

(73) Assignee: Cullinan Mica Corp, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/751,276

(22) Filed: Jun. 23, 2024

(65) Prior Publication Data

US 2025/0034262 A1    Jan. 30, 2025

Related U.S. Application Data

(63) Continuation of application No. 17/162,585, filed on Jan. 29, 2021, now Pat. No. 12,065,493, which is a continuation of application No. PCT/US2019/044234, filed on Jul. 30, 2019.

(60) Provisional application No. 62/712,608, filed on Jul. 31, 2018.

(51) Int. Cl.
*C07K 16/28*        (2006.01)

(52) U.S. Cl.
CPC ...... *C07K 16/2833* (2013.01); *C07K 2317/24* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 8,716,195 B2 | 5/2014 | Cappuccilli et al. | |
| 9,725,515 B2 | 8/2017 | Anderson et al. | |
| 12,065,493 B2 * | 8/2024 | Gibson | ............. C07K 16/2833 |
| 2017/0342161 A1 * | 11/2017 | Moon | .................... A61K 33/24 |

FOREIGN PATENT DOCUMENTS

| | | |
|---|---|---|
| WO | 2013117647 A1 | 8/2013 |
| WO | 2014140904 A2 | 9/2014 |
| WO | 2017157895 A1 | 9/2017 |
| WO | 2018081648 A2 | 5/2018 |

OTHER PUBLICATIONS

Brown et al. Tolerance to Single, but Not Multiple, Amino Acid Replacements in Antibody VH, CDR2. J Immunol (1996) 156 (9):3285-3291, DOI: 10.4049/jimmunol.156.9.3285 (Year: 1996).*

(Continued)

*Primary Examiner* — Amy E Juedes
*Assistant Examiner* — Hilary Ann Petrash
(74) *Attorney, Agent, or Firm* — Lathrop GPM LLP; Malaika O.D. Tyson

(57) ABSTRACT

Provided herein are antibodies that specifically bind to MICA/B having heavy chain, light chain, variable heavy chain domains (VH), variable light chain domains (VL), and complementarity determining regions (CDRs) disclosed herein, as well as methods and uses thereof.

4 Claims, 8 Drawing Sheets
Specification includes a Sequence Listing.

(56) References Cited

OTHER PUBLICATIONS

Clark et al. Influence of canonical structure determining residues on antibody affinity and stability. Journal of Structural Biology 185 (2014) 223-227, DOI: 10.1016/j.jsb.2013.08.009 (Year: 2014).*

Culang et al. The structural basis of antibody-antigen recognition. Front. In Immun. 2013. vol. 4, Article 302, pp. 1-13. DOI: 10.3389/fimmu.2013.00302 (Year: 2013).*

Jaiswal et al. (2022) Antibody multispecificity: a necessary evil? Molecular Immunology 152, pp. 153-161, DOI: 10.1016/j.molimm. 2022.10.012 (Year: 2022).*

Nakano et al. (2011) Free immunoglobulin light chain: its biology and implications in diseases. Clinica Chimica Acta 412, pp. 843-849, DOI: 10.1016/j.cca.2011.03.007 (Year: 2011).*

Quintero et al. (2021) Germline-Dependent Antibody Paratope States and Pairing Specific VH-VL Interface Dynamics. Front. Immunol. 12:675655. doi: 10.3389/fimmu.2021.675655 (Year: 2021).*

Bonnafous, C., et al., "Targeting MICA with therapeutic antibodies for the treatment of cancer," Journal for ImmunoTherapy of Cancer 2013, 1(Suppl 1):P41 http://www.immunotherapyofcancer.org/content/1/S1/P41, 2 pages, dated Nov. 7, 2013.

Ca Intellectual Property Office, "Office Action," regarding Application No. 3,108,022, 4 pages, dated Oct. 17, 2023.

Ferrari De Andrade, et al., Antibody-mediated inhibition of MICA and MICB shedding promotes NK cell-driven tumor immunity, Science. Mar. 30, 2018; 359(6383), 14 pages, dated Mar. 30, 2018. 4 pages, dated Dec. 17, 2023ISRAELI Patent Office, "Office Action," regarding Application No. 280487, dated Dec. 17, 2023.

MX Patent Office, "Office Action," regarding Application No. MX/a/2021/001254, 22 pages, mailed Mar. 24, 2025.

PH Patent Office, Request for Substantive Exam, regarding Application No. 1-2021-550232, 4 pages, mailed Nov. 27, 2024.

Australian Patent Office, Office Action, Notice of acceptance for patent application, AU Application No. 2019312656, dated Aug. 26, 2025.

Whalen et al., "CLN-619, a MICA/B monoclonal antibody that promotes innate immune cell-mediated antitumor activity", J. Immunother. Cancer, Apr. 23, 2025, 13(4): e008987.

Dondelinger et al., "Understanding the Significance and Implications of Antibody Numbering and Antigen-Binding Surface/Residue Definition", Frontiers in Immunology 9 (2018).

European Patent Office, Examination Report for EP Application No. 19844652.8 mailed Nov. 24, 2025, 8 pages.

Rudikoff et al., "Single amino acid substitution altering antigen-binding specificity" PNAS, USA 79:1979-1983 (1982).

Safdari et al., "Antibody humanization methods—a review and update", Biotechnology and Genetic Engineering Reviews 29(2):175-186 (2013).

* cited by examiner

NKG2D expression of
TIL alpha beta CD8⁺ T cells

NKG2D expression of
TIL gamma delta T cells

Soluble MicA

Surface MicA

Non-competition ctrl 5C3 binds α1/α2 domain

A4          Time (s)

ANTI-MICA/B ANTIBODIES THAT BLOCK MICA/B SHEDDING AND METHODS OF USE

CROSS-REFERENCE

This application is a continuation of U.S. patent application Ser. No. 17/162,585, filed Jan. 29, 2021, which issued as U.S. Pat. No. 12,065,493 on Jul. 31, 2024. U.S. patent application Ser. No. 17/162,585 is a bypass continuation of the then PCT Application No. PCT/US2019/044234, filed on Jul. 30, 2019, which claims the benefit of U.S. Provisional Application No. 62/712,608 filed Jul. 31, 2018. All of which are incorporated by reference herein in their entirety.

INCORPORATION BY REFERENCE OF SEQUENCE LISTING

This application contains a Sequence listing that has been submitted in a computer readable format and is hereby incorporated by reference in its entirety. The XML file, created on Sep. 1, 2024, is named 67252US03seq and is 47,432 bytes in size.

SUMMARY

Disclosed herein, are monoclonal antibodies that specifically bind to MICA/B and thereby modulating an immune response against disease cells.

Disclosed herein, in certain embodiments, are monoclonal antibodies or an antigen-binding fragments thereof, comprising a light chain comprising an amino acid sequence at least 80% identical to an amino acid sequence set forth as SEQ ID NO: 21, SEQ ID NO: 23, or SEQ ID NO: 24. In some embodiments, the monoclonal antibodies or an antigen-binding fragments thereof further comprises a heavy chain comprising an amino acid sequence at least 80% identical to an amino acid sequence set forth as SEQ ID NO: 22. SEQ ID NO: 25, or SEQ ID NO: 26.

Disclosed herein, in certain embodiments, are monoclonal antibodies or an antigen-binding fragments thereof, comprising a light chain variable domain (VL) comprising an amino acid sequence at least 80% identical to an amino acid sequence set forth as SEQ ID NO: 7, SEQ ID NO: 15, or SEQ ID NO: 19. Disclosed herein, in certain embodiments, are monoclonal antibodies or an antigen-binding fragments thereof, comprising a light chain variable domain (VL) comprising an amino acid sequence at least 90% identical to an amino acid sequence set forth as SEQ ID NO: 7. SEQ ID NO: 15, or SEQ ID NO: 19. Disclosed herein, in certain embodiments, are monoclonal antibodies or an antigen-binding fragments thereof, comprising a light chain variable domain (VL) comprising an amino acid sequence at least 95% identical to an amino acid sequence set forth as SEQ ID NO: 7, SEQ ID NO: 15, or SEQ ID NO: 19. Disclosed herein, in certain embodiments, are monoclonal antibodies or an antigen-binding fragments thereof, comprising a light chain variable domain (VL) comprising an amino acid sequence at least 99% identical to an amino acid sequence set forth as SEQ ID NO: 7, SEQ ID NO: 15, or SEQ ID NO: 19. Disclosed herein, in certain embodiments, are monoclonal antibodies or an antigen-binding fragments thereof, comprising a light chain variable domain (VL) comprising an amino acid sequence 100% identical to an amino acid sequence set forth as SEQ ID NO: 7, SEQ ID NO: 15, or SEQ ID NO: 19. In some instances, the monoclonal antibody or antigen-binding fragment thereof comprises a heavy chain variable domain (VH) comprising an amino acid sequence at least 80% identical to an amino acid sequence set forth as SEQ ID NO: 8, SEQ ID NO: 16, or SEQ ID NO: 20. In some instances, the monoclonal antibody or antigen-binding fragment thereof comprises a heavy chain variable domain (VH) comprising an amino acid sequence at least 90% identical to an amino acid sequence set forth as SEQ ID NO: 8. SEQ ID NO: 16, or SEQ ID NO: 20. In some instances, the monoclonal antibody or antigen-binding fragment thereof comprises a heavy chain variable domain (VH) comprising an amino acid sequence at least 95% identical to an amino acid sequence set forth as SEQ ID NO: 8, SEQ ID NO: 16, or SEQ ID NO: 20. In some instances, the monoclonal antibody or antigen-binding fragment thereof comprises a heavy chain variable domain (VH) comprising an amino acid sequence at least 99% identical to an amino acid sequence set forth as SEQ ID NO: 8, SEQ ID NO: 16, or SEQ ID NO: 20. In some instances, the monoclonal antibody or antigen-binding fragment thereof comprises a heavy chain variable domain (VH) comprising an amino acid sequence 100% identical to an amino acid sequence set forth as SEQ ID NO: 8, SEQ ID NO: 16, or SEQ ID NO: 20. In some instances, the monoclonal antibody or antigen-binding fragment thereof comprises a light chain variable domain (VL) comprising an amino acid sequence at least 80% identical to SEQ ID NO: 7 and a heavy chain variable domain (VH) comprising an amino acid sequence at least 80% identical to SEQ ID NO: 8. In some instances, the monoclonal antibody or antigen-binding fragment thereof comprises a light chain variable domain (VL) comprising an amino acid sequence at least 80% identical to SEQ ID NO: 15 and a heavy chain variable domain (VH) comprising an amino acid sequence at least 80% identical to SEQ ID NO: 16. In some instances, the monoclonal antibody or antigen-binding fragment thereof comprises a light chain variable domain (VL) comprising an amino acid sequence at least 80% identical to SEQ ID NO: 19 and a heavy chain variable domain (VH) comprising an amino acid sequence at least 80% identical to SEQ ID NO: 20. In some instances, the monoclonal antibody or antigen-binding fragment thereof comprises a light chain comprising an amino acid sequence at least 80% identical to an amino acid sequence set forth as SEQ ID NO: 21, SEQ ID NO: 23, or SEQ ID NO: 24. In some instances, the monoclonal antibody or antigen-binding fragment thereof comprises heavy chain comprising an amino acid sequence at least 80% identical to an amino acid sequence set forth as SEQ ID NO: 22. SEQ ID NO: 25, or SEQ ID NO: 26. In some instances, the monoclonal antibody or antigen-binding fragment thereof specifically binds to a MICA protein, a MICB protein, or both MICA and MICB protein. In some instances, the monoclonal antibody or antigen-binding fragment thereof binds to an alpha-3 domain of a MICA protein, a MICB protein, or both MICA and MICB protein. In some instances, the MICA protein is membrane-bound MICA protein, soluble MICA protein, or both. In some instances, the MICB protein is membrane-bound MICB protein, soluble MICB protein, or both. In some instances, the monoclonal antibody or antigen-binding fragment thereof is selected from a whole immunoglobulin, an seFv, a Fab, a F(ab')$_2$, or a disulfide linked Fv. In some instances, the monoclonal antibody or antigen-binding fragment thereof is an IgG or IgM. In some instances, the monoclonal antibody or antigen-binding fragment thereof is humanized or chimeric.

Disclosed herein, in certain embodiments, are monoclonal antibodies or an antigen-binding fragments thereof, comprising a heavy chain variable domain (VH) comprising an amino acid sequence at least 80% identical to an amino acid sequence set forth as SEQ ID NO: 8, SEQ ID NO: 16, or SEQ ID NO: 20. Disclosed herein, in certain embodiments, are monoclonal antibodies or an antigen-binding fragments thereof, comprising a heavy chain variable domain (VH) comprising an amino acid sequence at least 90% identical to an amino acid sequence set forth as SEQ ID NO: 8. SEQ ID NO: 16, or SEQ ID NO: 20. Disclosed herein, in certain embodiments, are monoclonal antibodies or an antigen-binding fragments thereof, comprising a heavy chain variable domain (VH) comprising an amino acid sequence at least 95% identical to an amino acid sequence set forth as SEQ ID NO: 8, SEQ ID NO: 16, or SEQ ID NO: 20. Disclosed herein, in certain embodiments, are monoclonal antibodies or an antigen-binding fragments thereof, comprising a heavy chain variable domain (VH) comprising an amino acid sequence at least 99% identical to an amino acid sequence set forth as SEQ ID NO: 8, SEQ ID NO: 16, or SEQ ID NO: 20. Disclosed herein, in certain embodiments, are monoclonal antibodies or an antigen-binding fragments thereof, comprising a heavy chain variable domain (VH) comprising an amino acid sequence 100% identical to an amino acid sequence set forth as SEQ ID NO: 8, SEQ ID NO: 16, or SEQ ID NO: 20. In some instances, the monoclonal antibody or antigen-binding fragment thereof comprises a light chain variable domain (VL) comprising an amino acid sequence at least 80% identical to an amino acid sequence set forth as SEQ ID NO: 7, SEQ ID NO: 15, or SEQ ID NO: 19. In some instances, the monoclonal antibody or antigen-binding fragment thereof comprises a light chain variable domain (VL) comprising an amino acid sequence at least 90% identical to an amino acid sequence set forth as SEQ ID NO: 7, SEQ ID NO: 15, or SEQ ID NO: 19. In some instances, the monoclonal antibody or antigen-binding fragment thereof comprises a light chain variable domain (VL) comprising an amino acid sequence at least 95% identical to an amino acid sequence set forth as SEQ ID NO: 7, SEQ ID NO: 15, or SEQ ID NO: 19. In some instances, the monoclonal antibody or antigen-binding fragment thereof comprises a light chain variable domain (VL) comprising an amino acid sequence at least 99% identical to an amino acid sequence set forth as SEQ ID NO: 7. SEQ ID NO: 15, or SEQ ID NO: 19. In some instances, the monoclonal antibody or antigen-binding fragment thereof comprises a light chain variable domain (VL) comprising an amino acid sequence 100% identical to an amino acid sequence set forth as SEQ ID NO: 7, SEQ ID NO: 15, or SEQ ID NO: 19. In some instances, the monoclonal antibody or antigen-binding fragment thereof comprises a heavy chain variable domain (VH) comprising an amino acid sequence at least 80% identical to SEQ ID NO: 8 and a light chain variable domain (VL) comprising an amino acid sequence at least 80% identical to SEQ ID NO: 7. In some instances, the monoclonal antibody or antigen-binding fragment thereof comprises a heavy chain variable domain (VH) comprising an amino acid sequence at least 80% identical to SEQ ID NO: 16 and a light chain variable domain (VL) comprising an amino acid sequence at least 80% identical to SEQ ID NO: 15. In some instances, the monoclonal antibody or antigen-binding fragment thereof comprises a heavy chain variable domain (VH) comprising an amino acid sequence at least 80% identical to SEQ ID NO: 20 and a light chain variable domain (VL) comprising an amino acid sequence at least 80% identical to SEQ ID NO: 19. In some instances, the monoclonal antibody or antigen-binding fragment thereof comprises a heavy chain comprising an amino acid sequence at least 80% identical to an amino acid sequence set forth as SEQ ID NO: 22, SEQ ID NO: 25, or SEQ ID NO: 26. In some instances, the monoclonal antibody or antigen-binding fragment thereof comprises a light chain comprising an amino acid sequence at least 80% identical to an amino acid sequence set forth as SEQ ID NO: 21, SEQ ID NO: 23, or SEQ ID NO: 24. In some instances, the monoclonal antibody or antigen-binding fragment thereof specifically binds to a MICA protein, a MICB protein, or both MICA and MICB protein. In some instances, the monoclonal antibody or antigen-binding fragment thereof binds to an alpha-3 domain of a MICA protein, a MICB protein, or both MICA and MICB protein. In some instances, the MICA protein is membrane-bound MICA protein, soluble MICA protein, or both. In some instances, the MICB protein is membrane-bound MICB protein, soluble MICB protein, or both. In some instances, the monoclonal antibody or antigen-binding fragment thereof is selected from a whole immunoglobulin, an scFv, a Fab, a F(ab')$_2$, or a disulfide linked Fv. In some instances, the monoclonal antibody or antigen-binding fragment thereof is an IgG or IgM. In some instances, the monoclonal antibody or antigen-binding fragment thereof is humanized or chimeric.

Disclosed herein, in certain embodiments, are monoclonal antibodies or an antigen-binding fragments thereof, comprising a light chain complementarity determining region (CDR) having an amino acid sequence at least 80% identical to at least one of the amino acid sequences set forth as SEQ ID NOS: 1-3, 9-11, and 17, wherein the monoclonal antibody does not have at least one CDR selected from the list comprising: SASQGISNYLN, TSLLHSG, QQYSKFPRT, GYTFTNYGMN, INTYTGEPTYADDFKG, and NYGNYLFDY. Disclosed herein, in certain embodiments, are monoclonal antibodies or an antigen-binding fragments thereof, comprising a light chain complementarity determining region (CDR) having an amino acid sequence at least 90% identical to at least one of the amino acid sequences set forth as SEQ ID NOS: 1-3, 9-11, and 17, wherein the monoclonal antibody does not have at least one CDR selected from the list comprising: SASQGISNYLN, TSLLHSG, QQYSKFPRT, GYTFTNYGMN, INTYTGEPTY ADDFKG, and NYGNYLFDY. Disclosed herein, in certain embodiments, are monoclonal antibodies or an antigen-binding fragments thereof, comprising a light chain complementarity determining region (CDR) having an amino acid sequence at least 95% identical to at least one of the amino acid sequences set forth as SEQ ID NOS: 1-3, 9-11, and 17, wherein the monoclonal antibody does not have at least one CDR selected from the list comprising: SASQGISNYLN, TSLLHSG, QQYSKFPRT, GYTFTNYGMN, INTYTGEPTYADDFKG, and NYGNYLFDY. Disclosed herein, in certain embodiments, are monoclonal antibodies or an antigen-binding fragments thereof, comprising a light chain complementarity determining region (CDR) having an amino acid sequence at least 99% identical to at least one of the amino acid sequences set forth as SEQ ID NOS: 1-3, 9-11, and 17, wherein the monoclonal antibody does not have at least one CDR selected from the list comprising: SASQGISNYLN, TSLLHSG, QQYSKFPRT, GYTFTNYGMN, INTYTGEPTYADDFKG, and NYGNYLFDY. Disclosed herein, in certain embodiments, are monoclonal antibodies or an antigen-binding fragments thereof, comprising a light chain complementarity determining region (CDR) having an amino acid sequence 100% identical to at least one of the amino acid sequences set forth as SEQ ID NOS: 1-3, 9-11, and 17, wherein the monoclonal antibody does not have at least one CDR selected from the list comprising: SASQ- GISNYLN, TSLLHSG, QQYSKFPRT, GYTFTNYGMN, INTYTGEPTY ADDFKG, and NYGNYLFDY. In some instances, the monoclonal antibody or antigen-binding fragment thereof comprises a heavy chain complementarity determining region (CDR) having an amino acid sequence at least 80% identical to at least one of the amino acid sequences set forth as SEQ ID NOS: 4-6, 12-14, and 18. In some instances, the monoclonal antibody or antigen-binding fragment thereof comprises a heavy chain complementarity determining region (CDR) having an amino acid sequence at least 90% identical to at least one of the amino acid sequences set forth as SEQ ID NOS: 4-6, 12-14, and 18. In some instances, the monoclonal antibody or antigen-binding fragment thereof comprises a heavy chain complementarity determining region (CDR) having an amino acid sequence at least 95% identical to at least one of the amino acid sequences set forth as SEQ ID NOS: 4-6, 12-14, and 18. In some instances, the monoclonal antibody or antigen-binding fragment thereof comprises a heavy chain complementarity determining region (CDR) having an amino acid sequence at least 99% identical to at least one of the amino acid sequences set forth as SEQ ID NOS: 4-6, 12-14, and 18. In some instances, the monoclonal antibody or antigen-binding fragment thereof comprises a heavy chain complementarity determining region (CDR) having an amino acid sequence 100% identical to at least one of the amino acid sequences set forth as SEQ ID NOS: 4-6, 12-14, and 18. In some instances, the monoclonal antibody or antigen-binding fragment thereof comprises a light chain complementarity determining region 1 (CDR1) having an amino acid sequence at least 80% identical to one of SEQ ID NO: 1. SEQ ID NO: 9, or SEQ ID NO: 17, a light chain complementarity determining region 2 (CDR2) having an amino acid sequence at least 80% identical to one of SEQ ID NOS: SEQ ID NO: 2, or SEQ ID NO: 10, a light chain complementarity determining region 3 (CDR3) having an amino acid sequence at least 80% identical to one of SEQ ID NO: 3, or SEQ ID NO: 11, a heavy chain complementarity determining region 1 (CDR1) having an amino acid sequence at least 80% identical to one of SEQ ID NO: 4, or SEQ ID NO: 12, a heavy chain complementarity determining region 2 (CDR2) having an amino acid sequence at least 80% identical to one of SEQ ID NO: 5, SEQ ID NO: 13, or SEQ ID NO: 18, and a heavy chain complementarity determining region 3 (CDR3) having an amino acid sequence at least 80% identical to one of SEQ ID NO: 6, or SEQ ID NO: 14. In some instances, the monoclonal antibody or antigen-binding fragment thereof comprises at least one of a light chain complementarity determining region 1 (CDR1) having an amino acid sequence at least 80% identical to SEQ ID NO: 1, a light chain complementarity determining region 2 (CDR2) having an amino acid sequence at least 80% identical to SEQ ID NO: 2, and a light chain complementarity determining region 3 (CDR3) having an amino acid sequence at least 80% identical to SEQ ID NO: 3. In some instances, the monoclonal antibody or antigen-binding fragment thereof comprises at least one of a light chain complementarity determining region 1 (CDR1) having an amino acid sequence at least 80% identical to SEQ ID NO: 9, a light chain complementarity determining region 2 (CDR2) having an amino acid sequence at least 80% identical to SEQ ID NO: 10, and a light chain complementarity determining region 3 (CDR3) having an amino acid sequence at least 80% identical to SEQ ID NO: 11. In some instances, the monoclonal antibody or antigen-binding fragment thereof comprises at least one of a light chain complementarity determining region 1 (CDR1) having an amino acid sequence at least 80% identical to SEQ ID NO: 17, a light chain complementarity determining region 2 (CDR2) having an amino acid sequence at least 80% identical to SEQ ID NO: 2, and a light chain complementarity determining region 3 (CDR3) having an amino acid sequence at least 80% identical to SEQ ID NO: 3. In some instances, the monoclonal antibody or antigen-binding fragment thereof comprises at least one of a heavy chain complementarity determining region 1 (CDR1) having an amino acid sequence at least 80% identical to SEQ ID NO: 4, a heavy chain complementarity determining region 2 (CDR2) having an amino acid sequence at least 80% identical to SEQ ID NO: 5, and a heavy chain complementarity determining region 3 (CDR3) having an amino acid sequence at least 80% identical to SEQ ID NO: 6. In some instances, the monoclonal antibody or antigen-binding fragment thereof comprises at least one of a heavy chain complementarity determining region 1 (CDR1) having an amino acid sequence at least 80% identical to SEQ ID NO: 12, a heavy chain complementarity determining region 2 (CDR2) having an amino acid sequence at least 80% identical to SEQ ID NO: 13, and a heavy chain complementarity determining region 3 (CDR3) having an amino acid sequence at least 80% identical to SEQ ID NO: 14. In some instances, the monoclonal antibody or antigen-binding fragment thereof comprises at least one of a heavy chain complementarity determining region 1 (CDR1) having an amino acid sequence at least 80% identical to SEQ ID NO: 4, a heavy chain complementarity determining region 2 (CDR2) having an amino acid sequence at least 80% identical to SEQ ID NO: 18, and a heavy chain complementarity determining region 3 (CDR3) having an amino acid sequence at least 80% identical to SEQ ID NO: 6. In some instances, the monoclonal antibody or antigen-binding fragment thereof comprises a light chain variable domain (VL) comprising an amino acid sequence at least 80% identical to an amino acid sequence set forth as SEQ ID NO: 7, SEQ ID NO: 15, or SEQ ID NO: 19. In some instances, the monoclonal antibody or antigen-binding fragment thereof comprises a heavy chain variable domain (VH) comprising an amino acid sequence at least 80% identical to an amino acid sequence set forth as SEQ ID NO: 8, SEQ ID NO:16, or SEQ ID NO: 20. In some instances, the monoclonal antibody or antigen-binding fragment thereof comprises a light chain variable domain (VL) comprising an amino acid sequence at least 80% identical to an amino acid sequence set forth as SEQ ID NO: 7, or SEQ ID NO: 15; and a heavy chain variable domain (VH) comprising an amino acid sequence at least 80% identical to an amino acid sequence set forth as SEQ ID NO: 8, or SEQ ID NO: 16. In some instances, the monoclonal antibody or antigen-binding fragment thereof comprises a heavy chain variable domain (VH) comprising an amino acid sequence at least 80% identical to an amino acid sequence set forth as SEQ ID NO: 8, or SEQ ID NO: 16; and a light chain variable domain (VL) comprising an amino acid sequence at least 80% identical to an amino acid sequence set forth as SEQ ID NO: 7, or SEQ ID NO: 15. In some instances, the monoclonal antibody or antigen-binding fragment thereof comprises a light chain variable domain (VL) comprising an amino acid sequence at least 80% identical to SEQ ID NO: 7 and a heavy chain variable domain (VH) comprising an amino acid sequence at least 80% identical to SEQ ID NO: 8. In some instances, the monoclonal antibody or antigen-binding fragment thereof comprises a light chain variable domain (VL) comprising an amino acid sequence at least 80% identical to SEQ ID NO: 15 and a heavy chain variable domain (VH) comprising an amino acid sequence at least 80% identical to SEQ ID NO: 16. In some instances, the monoclonal antibody or antigen-binding fragment thereof comprises a light chain variable domain (VL) comprising an amino acid sequence at least 80% identical to SEQ ID NO: 19 and a heavy chain variable domain (VH) comprising an amino acid sequence at least 80% identical to SEQ ID NO: 20. In some instances, the monoclonal antibody or antigen-binding fragment thereof comprises a light chain comprising an amino acid sequence at least 80% identical to an amino acid sequence set forth as SEQ ID NO: 21. SEQ ID NO: 23, or SEQ ID NO: 24. In some instances, the monoclonal antibody or antigen-binding fragment thereof comprises heavy chain comprising an amino acid sequence at least 80% identical to an amino acid sequence set forth as SEQ ID NO: 22, SEQ ID NO: 25, or SEQ ID NO: 26. In some instances, the monoclonal antibody or antigen-binding fragment thereof specifically binds to a MICA protein, a MICB protein, or both MICA and MICB protein. In some instances, the monoclonal antibody or antigen-binding fragment thereof binds to an alpha-3 domain of a MICA protein, a MICB protein, or both MICA and MICB protein. In some instances, the MICA protein is membrane-bound MICA protein, soluble MICA protein, or both. In some instances, the MICB protein is membrane-bound MICB protein, soluble MICB protein, or both. In some instances, the monoclonal antibody or antigen-binding fragment thereof is selected from a whole immunoglobulin, an scFv, a Fab, a F(ab')₂, or a disulfide linked Fv. In some instances, the monoclonal antibody or antigen-binding fragment thereof is an IgG or IgM. In some instances, the monoclonal antibody or antigen-binding fragment thereof is humanized or chimeric.

Disclosed herein, in certain embodiments, are monoclonal antibodies or an antigen-binding fragments thereof, comprising a heavy chain complementarity determining region (CDR) having an amino acid sequence at least 80% identical to at least one of the amino acid sequences set forth as SEQ ID NOS: 4-6, 12-14, and 18, wherein the monoclonal antibody does not have at least one CDR selected from the list comprising: SASQGISNYLN, TSLLHSG, QQYSKF-PRT, GYTFTNYGMN. INTYTGEPTYADDFKG, and NYGNYLFDY. Disclosed herein, in certain embodiments, are monoclonal antibodies or an antigen-binding fragments thereof, comprising a heavy chain complementarity determining region (CDR) having an amino acid sequence at least 90% identical to at least one of the amino acid sequences set forth as SEQ ID NOS: 4-6, 12-14, and 18, wherein the monoclonal antibody does not have at least one CDR selected from the list comprising: SASQGISNYLN, TSLLHSG, QQYSKFPRT. GYTFTNYGMN, INTYTGEP-TYADDFKG, and NYGNYLFDY. Disclosed herein, in certain embodiments, are monoclonal antibodies or an antigen-binding fragments thereof, comprising a heavy chain complementarity determining region (CDR) having an amino acid sequence at least 95% identical to at least one of the amino acid sequences set forth as SEQ ID NOS: 4-6, 12-14, and 18, wherein the monoclonal antibody does not have at least one CDR selected from the list comprising: SASQGISNYLN, TSLLHSG, QQYSKFPRT, GYTFTNYGMN, INTYTGEPTYADDFKG, and NYG-NYLFDY. Disclosed herein, in certain embodiments, are monoclonal antibodies or an antigen-binding fragments thereof, comprising a heavy chain complementarity deter-mining region (CDR) having an amino acid sequence at least 99% identical to at least one of the amino acid sequences set forth as SEQ ID NOS: 4-6, 12-14, and 18, wherein the monoclonal antibody does not have at least one CDR selected from the list comprising: SASQGISNYLN, TSLLHSG, QQYSKFPRT. GYTFTNYGMN. INTYTGEP-TYADDFKG, and NYGNYLFDY. Disclosed herein, in cer-tain embodiments, are monoclonal antibodies or an antigen-binding fragments thereof, comprising a heavy chain complementarity determining region (CDR) having an amino acid sequence 100% identical to at least one of the amino acid sequences set forth as SEQ ID NOS: 4-6, 12-14, and 18, wherein the monoclonal antibody does not have at least one CDR selected from the list comprising: SASQ-GISNYLN, TSLLHSG, QQYSKFPRT, GYTFTNYGMN, INTYTGEPTYADDFKG, and NYGNYLFDY. In some instances, the monoclonal antibody or antigen-binding frag-ment comprises a light chain complementarity determining region (CDR) having an amino acid sequence at least 80% identical to at least one of the amino acid sequences set forth as SEQ ID NOS: 1-3, 9-11, and 17. In some instances, the monoclonal antibody or antigen-binding fragment com-prises a light chain complementarity determining region (CDR) having an amino acid sequence at least 90% identical to at least one of the amino acid sequences set forth as SEQ ID NOS: 1-3, 9-11, and 17. In some instances, the mono-clonal antibody or antigen-binding fragment comprises a light chain complementarity determining region (CDR) hav-ing an amino acid sequence at least 95% identical to at least one of the amino acid sequences set forth as SEQ ID NOS: 1-3, 9-11, and 17. In some instances, the monoclonal anti-body or antigen-binding fragment comprises a light chain complementarity determining region (CDR) having an amino acid sequence at least 99% identical to at least one of the amino acid sequences set forth as SEQ ID NOS: 1-3, 9-11, and 17. In some instances, the monoclonal antibody or antigen-binding fragment comprises a light chain comple-mentarity determining region (CDR) having an amino acid sequence 100% identical to at least one of the amino acid sequences set forth as SEQ ID NOS: 1-3, 9-11, and 17. In some instances, the monoclonal antibody or antigen-binding fragment thereof comprises a heavy chain complementarity determining region 1 (CDR1) having an amino acid sequence at least 80% identical to one of SEQ ID NO: 4, or SEQ ID NO: 12, a heavy chain complementarity determin-ing region 2 (CDR2) having an amino acid sequence at least 80% identical to one of SEQ ID NO: 5, SEQ ID NO: 13, or SEQ ID NO: 18, a heavy chain complementarity determin-ing region 3 (CDR3) having an amino acid sequence at least 80% identical to one of SEQ ID NO: 6, or SEQ ID NO: 14, a light chain complementarity determining region 1 (CDR1) having an amino acid sequence at least 80% identical to one of SEQ ID NO: 1, SEQ ID NO: 9, or SEQ ID NO: 17, a light chain complementarity determining region 2 (CDR2) having an amino acid sequence at least 80% identical to one of SEQ ID NO: 2, or SEQ ID NO: 10, and a light chain comple-mentarity determining region 3 (CDR3) having an amino acid sequence at least 80% identical to one of SEQ ID NO: 3, or SEQ ID NO: 11. In some instances, the monoclonal antibody or antigen-binding fragment thereof comprises at least one of a heavy chain complementarity determining region 1 (CDR1) having an amino acid sequence at least 80% identical to SEQ ID NO: 4, a heavy chain complemen-tarity determining region 2 (CDR2) having an amino acid sequence at least 80% identical to SEQ ID NO: 5, and a heavy chain complementarity determining region 3 (CDR3) having an amino acid sequence at least 80% identical to SEQ ID NO: 6. In some instances, the monoclonal antibody or antigen-binding fragment thereof comprises at least one of a heavy chain complementarity determining region 1 (CDR1) having an amino acid sequence at least 80% identical to SEQ ID NO: 12, a heavy chain complementarity determining region 2 (CDR2) having an amino acid sequence at least 80% identical to SEQ ID NO: 13, and a heavy chain complementarity determining region 3 (CDR3) having an amino acid sequence at least 80% identical to SEQ ID NO: 14. In some instances, the monoclonal antibody or antigen-binding fragment thereof comprises at least one of a heavy chain complementarity determining region 1 (CDR1) having an amino acid sequence at least 80% identical to SEQ ID NO: 4, a heavy chain complementarity determining region 2 (CDR2) having an amino acid sequence at least 80% identical to SEQ ID NO: 18, and a heavy chain complementarity determining region 3 (CDR3) having an amino acid sequence at least 80% identical to SEQ ID NO: 6. In some instances, the monoclonal antibody or antigen-binding fragment thereof comprises at least one of a light chain complementarity determining region 1 (CDR1) having an amino acid sequence at least 80% identical to SEQ ID NO: 1, a light chain complementarity determining region 2 (CDR2) having an amino acid sequence at least 80% identical to SEQ ID NO: 2, and a light chain complementarity determining region 3 (CDR3) having an amino acid sequence at least 80% identical to SEQ ID NO: 3. In some instances, the monoclonal antibody or antigen-binding fragment thereof comprises at least one of a light chain complementarity determining region 1 (CDR1) having an amino acid sequence at least 80% identical to SEQ ID NO: 9, a light chain complementarity determining region 2 (CDR2) having an amino acid sequence at least 80% identical to SEQ ID NO: 10, and a light chain complementarity determining region 3 (CDR3) having an amino acid sequence at least 80% identical to SEQ ID NO: 11. In some instances, the monoclonal antibody or antigen-binding fragment thereof comprises at least one of a light chain complementarity determining region 1 (CDR1) having an amino acid sequence at least 80% identical to SEQ ID NO: 17, a light chain complementarity determining region 2 (CDR2) having an amino acid sequence at least 80% identical to SEQ ID NO: 2, and a light chain complementarity determining region 3 (CDR3) having an amino acid sequence at least 80% identical to SEQ ID NO: 3. In some instances, the monoclonal antibody or antigen-binding fragment thereof comprises a heavy chain variable domain (VH) comprising an amino acid sequence at least 80% identical to an amino acid sequence set forth as SEQ ID NO: 8, SEQ ID NO:16, or SEQ ID NO:20. In some instances, the monoclonal antibody or antigen-binding fragment thereof comprises a light chain variable domain (VL) comprising an amino acid sequence at least 80% identical to an amino acid sequence set forth as SEQ ID NO: 7, SEQ ID NO: 15, or SEQ ID NO:19. In some instances, the monoclonal antibody or antigen-binding fragment thereof comprises a heavy chain variable domain (VH) comprising an amino acid sequence at least 80% identical to an amino acid sequence set forth as SEQ ID NO: 8, SEQ ID NO: 16, or SEQ ID NO:20; and a light chain variable domain (VL) comprising an amino acid sequence at least 80% identical to an amino acid sequence set forth as SEQ ID NO: 7, SEQ ID NO: 15, or SEQ ID NO: 19. In some instances, the monoclonal antibody or antigen-binding fragment thereof comprises a light chain variable domain (VL) comprising an amino acid sequence at least 80% identical to an amino acid sequence set forth as SEQ ID NO: 7, or SEQ ID NO: 15; and a heavy chain variable domain (VH) comprising an amino acid sequence at least 80% identical to an amino acid sequence set forth as SEQ ID NO: 8, or SEQ ID NO: 16. In some instances, the monoclonal antibody or antigen-binding fragment thereof comprises a heavy chain variable domain (VH) comprising an amino acid sequence at least 80% identical to an amino acid sequence set forth as SEQ ID NO: 8 and a light chain variable domain (VL) comprising an amino acid sequence at least 80% identical to an amino acid sequence set forth as SEQ ID NO: 7. In some instances, the monoclonal antibody or antigen-binding fragment thereof comprises a heavy chain variable domain (VH) comprising an amino acid sequence at least 80% identical to an amino acid sequence set forth as SEQ ID NO: 16; and a light chain variable domain (VL) comprising an amino acid sequence at least 80% identical to an amino acid sequence set forth as SEQ ID NO: 15. In some instances, the monoclonal antibody or antigen-binding fragment thereof comprises a heavy chain variable domain (VH) comprising an amino acid sequence at least 80% identical to an amino acid sequence set forth as SEQ ID NO: 20; and a light chain variable domain (VL) comprising an amino acid sequence at least 80% identical to an amino acid sequence set forth as SEQ ID NO: 19. In some instances, the monoclonal antibody or antigen-binding fragment thereof comprises a heavy chain comprising an amino acid sequence at least 80% identical to an amino acid sequence set forth as SEQ ID NO: 22, SEQ ID NO: 25, or SEQ ID NO: 26. In some instances, the monoclonal antibody or antigen-binding fragment thereof comprises a light chain comprising an amino acid sequence at least 80% identical to an amino acid sequence set forth as SEQ ID NO: 21. SEQ ID NO: 23, or SEQ ID NO: 24. In some instances, the monoclonal antibody or antigen-binding fragment thereof specifically binds to a MICA protein, a MICB protein, or both MICA and MICB protein. In some instances, the monoclonal antibody or antigen-binding fragment thereof binds to an alpha-3 domain of a MICA protein, a MICB protein, or both MICA and MICB protein. In some instances, the MICA protein is membrane-bound MICA protein, soluble MICA protein, or both. In some instances, the MICB protein is membrane-bound MICB protein, soluble MICB protein, or both. In some instances, the monoclonal antibody or antigen-binding fragment thereof is selected from a whole immunoglobulin, an scFv, a Fab, a F(ab')$_2$, or a disulfide linked Fv. In some instances, the monoclonal antibody or antigen-binding fragment thereof is an IgG or IgM. In some instances, the monoclonal antibody or antigen-binding fragment thereof is humanized or chimeric.

Disclosed herein, in certain embodiments, are pharmaceutical compositions comprising: a monoclonal antibody or an antigen-binding fragment thereof according to any one of the disclosures herein; and a pharmaceutically acceptable carrier or excipient.

Disclosed herein, in certain embodiments, are methods of treating cancer in an individual in need thereof, comprising administering to the individual an effective amount of a monoclonal antibody or an antigen-binding fragment thereof comprising a light chain complementarity determining region (CDR) having an amino acid sequence at least 80% identical to at least one of the amino acid sequences set forth as SEQ ID NOS: 1-3, 9-11, and 17, wherein the monoclonal antibody does not have at least one CDR selected from the list comprising: SASQGISNYLN, TSLLHSG, QQYSKF-PRT, GYTFTNYGMN, INTYTGEPTYADDFKG, and NYGNYLFDY. Disclosed herein, in certain embodiments, are methods of treating cancer in an individual in need thereof, comprising administering to the individual an effective amount of a monoclonal antibody or an antigen-binding fragment thereof comprising a heavy chain complementarity determining region (CDR) having an amino acid sequence at least 80% identical to at least one of the amino acid sequences set forth as SEQ ID NOS: 4-6, 12-14, and 18, wherein the monoclonal antibody does not have at least one CDR selected from the list comprising: SASQGISNYLN, TSLLHSG, QQYSKFPRT. GYTFTNYGMN, INTYTGEP-TYADDFKG, and NYGNYLEDY. In some instances, the monoclonal antibody or antigen-binding fragment thereof comprises (a) a light chain complementarity determining region (CDR) having an amino acid sequence at least 80% identical to at least one of the amino acid sequences set forth as SEQ ID NOS: 1-3, 9-11, and 17; and (b) a heavy chain complementarity determining region (CDR) having an amino acid sequence at least 80% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence at least 90% identical to at least one of the amino acid sequences set forth as SEQ ID NOS: 1-3, 9-11, and 17; and (b) a heavy chain complementarity determining region (CDR) having an amino acid sequence at least 90% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence at least 95% identical to at least one of the amino acid sequences set forth as SEQ ID NOS: 1-3, 9-11, and 17; and (b) a heavy chain complementarity determining region (CDR) having an amino acid sequence at least 95% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence at least 99% identical to at least one of the amino acid sequences set forth as SEQ ID NOS: 1-3, 9-11, and 17; and (b) a heavy chain complementarity determining region (CDR) having an amino acid sequence at least 99% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence 100% identical to at least one of the amino acid sequences set forth as SEQ ID NOS: 1-3, 9-11, and 17; and (b) a heavy chain complementarity determining region (CDR) having an amino acid sequence 100% identical to at least one of the amino acid sequences set forth as SEQ ID NOS: 4-6, 12-14, and 18. In some instances, the monoclonal antibody or antigen-binding fragment thereof comprises a light chain complementarity determining region 1 (CDR1) having an amino acid sequence at least 80% identical to one of SEQ ID NO: 1. SEQ ID NO: 9, or SEQ ID NO: 17, a light chain complementarity determining region 2 (CDR2) having an amino acid sequence at least 80% identical to one of SEQ ID NOS: SEQ ID NO: 2, or SEQ ID NO: 10, a light chain complementarity determining region 3 (CDR3) having an amino acid sequence at least 80% identical to one of SEQ ID NO: 3, or SEQ ID NO: 11, a heavy chain complementarity determining region 1 (CDR1) having an amino acid sequence at least 80% identical to one of SEQ ID NO: 4, or SEQ ID NO: 12, a heavy chain complementarity determining region 2 (CDR2) having an amino acid sequence at least 80% identical to one of SEQ ID NO: 5, SEQ ID NO: 13, or SEQ ID NO: 18, and a heavy chain complementarity determining region 3 (CDR3) having an amino acid sequence at least 80% identical to one of SEQ ID NO: 6, or SEQ ID NO:

14. In some instances, the monoclonal antibody or antigen-binding fragment thereof comprises at least one of a light chain complementarity determining region 1 (CDR1) having an amino acid sequence at least 80% identical to SEQ ID NO: 1, a light chain complementarity determining region 2 (CDR2) having an amino acid sequence at least 80% identical to SEQ ID NO: 2, and a light chain complementarity determining region 3 (CDR3) having an amino acid sequence at least 80% identical to SEQ ID NO: 3. In some instances, the monoclonal antibody or antigen-binding fragment thereof comprises at least one of a light chain complementarity determining region 1 (CDR1) having an amino acid sequence at least 80% identical to SEQ ID NO: 9, a light chain complementarity determining region 2 (CDR2) having an amino acid sequence at least 80% identical to SEQ ID NO: 10, and a light chain complementarity determining region 3 (CDR3) having an amino acid sequence at least 80% identical to SEQ ID NO: 11. In some instances, the monoclonal antibody or antigen-binding fragment thereof comprises at least one of a light chain complementarity determining region 17 (CDR1) having an amino acid sequence at least 80% identical to SEQ ID NO: 1, a light chain complementarity determining region 2 (CDR2) having an amino acid sequence at least 80% identical to SEQ ID NO: 2, and a light chain complementarity determining region 3 (CDR3) having an amino acid sequence at least 80% identical to SEQ ID NO: 3. In some instances, the monoclonal antibody or antigen-binding fragment thereof comprises at least one of a heavy chain complementarity determining region 1 (CDR1) having an amino acid sequence at least 80% identical to SEQ ID NO: 4, a heavy chain complementarity determining region 2 (CDR2) having an amino acid sequence at least 80% identical to SEQ ID NO: 5, and a heavy chain complementarity determining region 3 (CDR3) having an amino acid sequence at least 80% identical to SEQ ID NO: 6. In some instances, the monoclonal antibody or antigen-binding fragment thereof comprises at least one of a heavy chain complementarity determining region 1 (CDR1) having an amino acid sequence at least 80% identical to SEQ ID NO: 12, a heavy chain complementarity determining region 2 (CDR2) having an amino acid sequence at least 80% identical to SEQ ID NO: 13, and a heavy chain complementarity determining region 3 (CDR3) having an amino acid sequence at least 80% identical to SEQ ID NO: 14. In some instances, the monoclonal antibody or antigen-binding fragment thereof comprises at least one of a heavy chain complementarity determining region 1 (CDR1) having an amino acid sequence at least 80% identical to SEQ ID NO: 4, a heavy chain complementarity determining region 2 (CDR2) having an amino acid sequence at least 80% identical to SEQ ID NO: 18, and a heavy chain complementarity determining region 3 (CDR3) having an amino acid sequence at least 80% identical to SEQ ID NO: 6. In some instances, the monoclonal antibody or antigen-binding fragment thereof comprises a light chain variable domain (VL) comprising an amino acid sequence at least 80% identical to an amino acid sequence set forth as SEQ ID NO: 7, SEQ ID NO: 15, or SEQ ID NO: 19. In some instances, the monoclonal antibody or antigen-binding fragment thereof comprises a heavy chain variable domain (VH) comprising an amino acid sequence at least 80% identical to an amino acid sequence set forth as SEQ ID NO: 8, SEQ ID NO:16, or SEQ ID NO: 20. In some instances, the monoclonal antibody or antigen-binding fragment thereof comprises a light chain variable domain (VL) comprising an amino acid sequence at least 80% identical to an amino acid sequence set forth as SEQ ID NO: 7, SEQ ID NO: 15, or SEQ ID NO: 19; and a heavy chain variable domain (VH) comprising an amino acid sequence at least 80% identical to an amino acid sequence set forth as SEQ ID NO: 8, SEQ ID NO: 16, or SEQ ID NO: 20. In some instances, the monoclonal antibody or antigen-binding fragment thereof comprises a light chain variable domain (VL) comprising an amino acid sequence at least 80% identical to SEQ ID NO: 7 and a heavy chain variable domain (VH) comprising an amino acid sequence at least 80% identical to SEQ ID NO: 8. In some instances, the monoclonal antibody or antigen-binding fragment thereof comprises a light chain variable domain (VL) comprising an amino acid sequence at least 80% identical to SEQ ID NO: 15 and a heavy chain variable domain (VH) comprising an amino acid sequence at least 80% identical to SEQ ID NO: 16. In some instances, the monoclonal antibody or antigen-binding fragment thereof comprises a light chain variable domain (VL) comprising an amino acid sequence at least 80% identical to SEQ ID NO: 19 and a heavy chain variable domain (VH) comprising an amino acid sequence at least 80% identical to SEQ ID NO: 20. In some instances, the monoclonal antibody or antigen-binding fragment thereof comprises a light chain comprising an amino acid sequence at least 80% identical to an amino acid sequence set forth as SEQ ID NO: 21. SEQ ID NO: 23, or SEQ ID NO: 24. In some instances, the monoclonal antibody or antigen-binding fragment thereof comprises a heavy chain comprising an amino acid sequence at least 80% identical to an amino acid sequence set forth as SEQ ID NO: 22, SEQ ID NO: 25, or SEQ ID NO: 26. In some instances, the monoclonal antibody or antigen-binding fragment thereof specifically binds to a MICA protein, a MICB protein, or both MICA and MICB protein. In some instances, the monoclonal antibody or antigen-binding fragment thereof binds to an alpha-3 domain of a MICA protein, a MICB protein, or both MICA and MICB protein. In some instances, the MICA protein is membrane-bound MICA protein, soluble MICA protein, or both. In some instances, the MICB protein is membrane-bound MICB protein, soluble MICB protein, or both. In some instances, the monoclonal antibody or antigen-binding fragment thereof is selected from a whole immunoglobulin, an scFv, a Fab, a F(ab')$_2$, or a disulfide linked Fv. In some instances, the monoclonal antibody or antigen-binding fragment thereof is an IgG or IgM. In some instances, the monoclonal antibody or antigen-binding fragment thereof is humanized or chimeric. In some instances, the monoclonal antibody or antigen-binding fragment thereof reduces level of soluble MICA protein, soluble MICB protein, or both. In some instances, the monoclonal antibody or antigen-binding fragment thereof reduces shedding of soluble MICA protein, soluble MICB protein, or both. In some instances, the monoclonal antibody or antigen-binding fragment thereof inhibits shedding of soluble MICA protein, soluble MICB protein, or both. In some instances, the cancer is hepatocellular carcinoma.

Disclosed herein, in certain embodiments, are methods of treating hepatocellular carcinoma in an individual in need thereof, comprising administering to the individual an effective amount of a monoclonal antibody or an antigen-binding fragment thereof comprising a light chain complementarity determining region (CDR) having an amino acid sequence at least 80% identical to at least one of the amino acid sequences set forth as SEQ ID NOS: 1-3, 9-11, and 17, wherein the monoclonal antibody does not have at least one CDR selected from the list comprising: SASQGISNYLN, TSLLHSG, QQYSKFPRT, GYTFTNYGMN, INTYTGEP-TYADDFKG, and NYGNYLFDY. Disclosed herein, in certain embodiments, are methods of treating hepatocellular carcinoma in an individual in need thereof, comprising administering to the individual an effective amount of a monoclonal antibody or an antigen-binding fragment thereof comprising a heavy chain complementarity determining region (CDR) having an amino acid sequence at least 80% identical to at least one of the amino acid sequences set forth as SEQ ID NOS: 4-6, 12-14, and 18, wherein the monoclonal antibody does not have at least one CDR selected from the list comprising: SASQGISNYLN, TSLLHSG, QQYSKFPRT, GYTFTNYGMN, INTYTGEPTY-ADDFKG, and NYGNYLFDY. In some instances, the monoclonal antibody or antigen-binding fragment thereof comprises (a) a light chain complementarity determining region (CDR) having an amino acid sequence at least 80% identical to at least one of the amino acid sequences set forth as SEQ ID NOS: 1-3, 9-11, and 17; and (b) a heavy chain complementarity determining region (CDR) having an amino acid sequence at least 80% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence at least 90% identical to at least one of the amino acid sequences set forth as SEQ ID NOS: 1-3, 9-11, and 17; and (b) a heavy chain complementarity determining region (CDR) having an amino acid sequence at least 90% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence at least 95% identical to at least one of the amino acid sequences set forth as SEQ ID NOS: 1-3, 9-11, and 17; and (b) a heavy chain complementarity determining region (CDR) having an amino acid sequence at least 95% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence at least 99% identical to at least one of the amino acid sequences set forth as SEQ ID NOS: 1-3, 9-11, and 17; and (b) a heavy chain complementarity determining region (CDR) having an amino acid sequence at least 99% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence 100% identical to at least one of the amino acid sequences set forth as SEQ ID NOS: 1-3, 9-11, and 17; and (b) a heavy chain complementarity determining region (CDR) having an amino acid sequence 100% identical to at least one of the amino acid sequences set forth as SEQ ID NOS: 4-6, 12-14, and 18. In some instances, the monoclonal antibody or antigen-binding fragment thereof comprises a light chain complementarity determining region 1 (CDR1) having an amino acid sequence at least 80% identical to one of SEQ ID NO: 1, SEQ ID NO: 9, or SEQ ID NO: 17, a light chain complementarity determining region 2 (CDR2) having an amino acid sequence at least 80% identical to one of SEQ ID NOS: SEQ ID NO: 2, or SEQ ID NO: 10, a light chain complementarity determining region 3 (CDR3) having an amino acid sequence at least 80% identical to one of SEQ ID NO: 3, or SEQ ID NO: 11, a heavy chain complementarity determining region 1 (CDR1) having an amino acid sequence at least 80% identical to one of SEQ ID NO: 4, or SEQ ID NO: 12, a heavy chain complementarity determining region 2 (CDR2) having an amino acid sequence at least 80% identical to one of SEQ ID NO: 5, SEQ ID NO: 13, or SEQ ID NO: 18, and a heavy chain complementarity determining region 3 (CDR3) having an amino acid sequence at least 80% identical to one of SEQ ID NO: 6, or SEQ ID NO: 14. In some instances, the monoclonal antibody or antigen-binding fragment thereof comprises at least one of a light chain complementarity determining region 1 (CDR1) having an amino acid sequence at least 80% identical to SEQ ID NO: 1, a light chain complementarity determining region 2 (CDR2) having an amino acid sequence at least 80% identical to SEQ ID NO: 2, and a light chain complementarity determining region 3 (CDR3) having an amino acid sequence at least 80% identical to SEQ ID NO: 3. In some instances, the monoclonal antibody or antigen-binding fragment thereof comprises at least one of a light chain complementarity determining region 1 (CDR1) having an amino acid sequence at least 80% identical to SEQ ID NO: 9, a light chain complementarity determining region 2 (CDR2) having an amino acid sequence at least 80% identical to SEQ ID NO: 10, and a light chain complementarity determining region 3 (CDR3) having an amino acid sequence at least 80% identical to SEQ ID NO: 11. In some instances, the monoclonal antibody or antigen-binding fragment thereof comprises at least one of a light chain complementarity determining region 17 (CDR1) having an amino acid sequence at least 80% identical to SEQ ID NO: 1, a light chain complementarity determining region 2 (CDR2) having an amino acid sequence at least 80% identical to SEQ ID NO: 2, and a light chain complementarity determining region 3 (CDR3) having an amino acid sequence at least 80% identical to SEQ ID NO: 3. In some instances, the monoclonal antibody or antigen-binding fragment thereof comprises at least one of a heavy chain complementarity determining region 1 (CDR1) having an amino acid sequence at least 80% identical to SEQ ID NO: 4, a heavy chain complementarity determining region 2 (CDR2) having an amino acid sequence at least 80% identical to SEQ ID NO: 5, and a heavy chain complementarity determining region 3 (CDR3) having an amino acid sequence at least 80% identical to SEQ ID NO: 6. In some instances, the monoclonal antibody or antigen-binding fragment thereof comprises at least one of a heavy chain complementarity determining region 1 (CDR1) having an amino acid sequence at least 80% identical to SEQ ID NO: 12, a heavy chain complementarity determining region 2 (CDR2) having an amino acid sequence at least 80% identical to SEQ ID NO: 13, and a heavy chain complementarity determining region 3 (CDR3) having an amino acid sequence at least 80% identical to SEQ ID NO: 14. In some instances, the monoclonal antibody or antigen-binding fragment thereof comprises at least one of a heavy chain complementarity determining region 1 (CDR1) having an amino acid sequence at least 80% identical to SEQ ID NO: 4, a heavy chain complementarity determining region 2 (CDR2) having an amino acid sequence at least 80% identical to SEQ ID NO: 18, and a heavy chain complementarity determining region 3 (CDR3) having an amino acid sequence at least 80% identical to SEQ ID NO: 6. In some instances, the monoclonal antibody or antigen-binding fragment thereof comprises a light chain variable domain (VL) comprising an amino acid sequence at least 80% identical to an amino acid sequence set forth as SEQ ID NO: 7. SEQ ID NO: 15, or SEQ ID NO: 19. In some instances, the monoclonal antibody or antigen-binding fragment thereof comprises a heavy chain variable domain (VH) comprising an amino acid sequence at least 80% identical to an amino acid sequence set forth as SEQ ID NO: 8, SEQ ID NO: 16, or SEQ ID NO: 20. In some instances, the monoclonal antibody or antigen-binding fragment thereof comprises a light chain variable domain (VL) comprising an amino acid sequence at least 80% identical to an amino acid sequence set forth as SEQ ID NO: 7. SEQ ID NO: 15, or SEQ ID NO: 19; and a heavy chain variable domain (VH) comprising an amino acid sequence at least 80% identical to an amino acid sequence set forth as SEQ ID NO: 8. SEQ ID NO: 16, or SEQ ID NO: 20. In some instances, the monoclonal antibody or antigen-binding fragment thereof comprises a light chain variable domain (VL) comprising an amino acid sequence at least 80% identical to SEQ ID NO: 7 and a heavy chain variable domain (VH) comprising an amino acid sequence at least 80% identical to SEQ ID NO: 8. In some instances, the monoclonal antibody or antigen-binding fragment thereof comprises a light chain variable domain (VL) comprising an amino acid sequence at least 80% identical to SEQ ID NO: 15 and a heavy chain variable domain (VH) comprising an amino acid sequence at least 80% identical to SEQ ID NO: 16. In some instances, the monoclonal antibody or antigen-binding fragment thereof comprises a light chain variable domain (VL) comprising an amino acid sequence at least 80% identical to SEQ ID NO: 19 and a heavy chain variable domain (VH) comprising an amino acid sequence at least 80% identical to SEQ ID NO: 20. In some instances, the monoclonal antibody or antigen-binding fragment thereof comprises a light chain comprising an amino acid sequence at least 80% identical to an amino acid sequence set forth as SEQ ID NO: 21, SEQ ID NO: 23, or SEQ ID NO: 24. In some instances, the monoclonal antibody or antigen-binding fragment thereof comprises a heavy chain comprising an amino acid sequence at least 80% identical to an amino acid sequence set forth as SEQ ID NO: 22, SEQ ID NO: 25, or SEQ ID NO: 26. In some instances, the monoclonal antibody or antigen-binding fragment thereof specifically binds to a MICA protein, a MICB protein, or both MICA and MICB protein. In some instances, the monoclonal antibody or antigen-binding fragment thereof binds to an alpha-3 domain of a MICA protein, a MICB protein, or both MICA and MICB protein. In some instances, the MICA protein is membrane-bound MICA protein, soluble MICA protein, or both. In some instances, the MICB protein is membrane-bound MICB protein, soluble MICB protein, or both. In some instances, the monoclonal antibody or antigen-binding fragment thereof is selected from a whole immunoglobulin, an scFv, a Fab, a F(ab')$_2$, or a disulfide linked Fv. In some instances, the monoclonal antibody or antigen-binding fragment thereof is an IgG or IgM. In some instances, the monoclonal antibody or fragment thereof is humanized or chimeric. In some instances, the monoclonal antibody or antigen binding fragment thereof reduces level of soluble MICA protein, soluble MICB protein, or both. In some instances, the monoclonal antibody or antigen binding fragment thereof reduces shedding of soluble MICA protein, soluble MICB protein, or both. In some instances, the monoclonal antibody or antigen binding fragment thereof inhibits shedding of soluble MICA protein, soluble MICB protein, or both.

Disclosed herein, in certain embodiments, are methods of reducing level of soluble MICA protein, soluble MICB protein, or both in an individual in need thereof, comprising administering to the individual an effective amount of a monoclonal antibody or an antigen-binding fragment thereof comprising a light chain complementarity determining region (CDR) having an amino acid sequence at least 80% identical to at least one of the amino acid sequences set forth as SEQ ID NOS: 1-3, 9-11, and 17, wherein the monoclonal antibody does not have at least one CDR selected from the list comprising: SASQGISNYLN, TSLLHSG, QQYSKF-PRT, GYTFTNYGMN, INTYTGEPTYADDFKG, and NYGNYLFDY. Disclosed herein, in certain embodiments, are methods of reducing level of soluble MICA protein, soluble MICB protein, or both in an individual in need thereof, comprising administering to the individual an effective amount of a monoclonal antibody or an antigen-binding fragment thereof comprising a heavy chain complementarity determining region (CDR) having an amino acid sequence at least 80% identical to at least one of the amino acid sequences set forth as SEQ ID NOS: 4-6, 12-14, and 18, wherein the monoclonal antibody does not have at least one CDR selected from the list comprising: SASQGISNYLN, TSLLHSG, QQYSKFPRT, GYTFTNYGMN, INTYTGEP-TYADDFKG, and NYGNYLFDY. In some instances, the monoclonal antibody or antigen-binding fragment thereof comprises (a) a light chain complementarity determining region (CDR) having an amino acid sequence at least 80% identical to at least one of the amino acid sequences set forth as SEQ ID NOS: 1-3, 9-11, and 17; and (b) a heavy chain complementarity determining region (CDR) having an amino acid sequence at least 80% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence at least 90% identical to at least one of the amino acid sequences set forth as SEQ ID NOS: 1-3, 9-11, and 17; and (b) a heavy chain complementarity determining region (CDR) having an amino acid sequence at least 90% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence at least 95% identical to at least one of the amino acid sequences set forth as SEQ ID NOS: 1-3, 9-11, and 17; and (b) a heavy chain complementarity determining region (CDR) having an amino acid sequence at least 95% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence at least 99% identical to at least one of the amino acid sequences set forth as SEQ ID NOS: 1-3, 9-11, and 17; and (b) a heavy chain complementarity determining region (CDR) having an amino acid sequence at least 99% identical to at least one of the amino acid sequences set forth as SEQ ID NOS: 4-6, 12-14, and 18. In some instances, the monoclonal antibody or antigen-binding fragment thereof comprises (a) a light chain complementarity determining region (CDR) having an amino acid sequence 100% identical to at least one of the amino acid sequences set forth as SEQ ID NOS: 1-3, 9-11, and 17; and (b) a heavy chain complementarity determining region (CDR) having an amino acid sequence 100% identical to at least one of the amino acid sequences set forth as SEQ ID NOS: 4-6, 12-14, and 18. In some instances, the monoclonal antibody or antigen-binding fragment thereof comprises a light chain complementarity determining region 1 (CDR1) having an amino acid sequence at least 80% identical to one of SEQ ID NO: 1. SEQ ID NO: 9, or SEQ ID NO: 17, a light chain complementarity determining region 2 (CDR2) having an amino acid sequence at least 80% identical to one of SEQ ID NOS: SEQ ID NO: 2, or SEQ ID NO: 10, a light chain complementarity determining region 3 (CDR3) having an amino acid sequence at least 80% identical to one of SEQ ID NO: 3, or SEQ ID NO: 11, a heavy chain complementarity determining region 1 (CDR1) having an amino acid sequence at least 80% identical to one of SEQ ID NO: 4, or SEQ ID NO: 12, a heavy chain complementarity determining region 2 (CDR2) having an amino acid sequence at least 80% identical to one of SEQ ID NO: 5, SEQ ID NO: 13, or SEQ ID NO: 18, and a heavy chain complementarity determining region 3 (CDR3) having an amino acid sequence at least 80% identical to one of SEQ ID NO: 6, or SEQ ID NO: 14. In some instances, the monoclonal antibody or antigen-binding fragment thereof comprises at least one of a light chain complementarity determining region 1 (CDR1) having an amino acid sequence at least 80% identical to SEQ ID NO: 1, a light chain complementarity determining region 2 (CDR2) having an amino acid sequence at least 80% identical to SEQ ID NO: 2, and a light chain complementarity determining region 3 (CDR3) having an amino acid sequence at least 80% identical to SEQ ID NO: 3. In some instances, the monoclonal antibody or antigen-binding fragment thereof comprises at least one of a light chain complementarity determining region 1 (CDR1) having an amino acid sequence at least 80% identical to SEQ ID NO: 9, a light chain complementarity determining region 2 (CDR2) having an amino acid sequence at least 80% identical to SEQ ID NO: 10, and a light chain complementarity determining region 3 (CDR3) having an amino acid sequence at least 80% identical to SEQ ID NO: 11. In some instances, the monoclonal antibody or antigen-binding fragment thereof comprises at least one of a light chain complementarity determining region 1 (CDR1) having an amino acid sequence at least 80% identical to SEQ ID NO: 17, a light chain complementarity determining region 2 (CDR2) having an amino acid sequence at least 80% identical to SEQ ID NO: 2, and a light chain complementarity determining region 3 (CDR3) having an amino acid sequence at least 80% identical to SEQ ID NO: 3. In some instances, the monoclonal antibody or antigen-binding fragment thereof comprises at least one of a heavy chain complementarity determining region 1 (CDR1) having an amino acid sequence at least 80% identical to SEQ ID NO: 4, a heavy chain complementarity determining region 2 (CDR2) having an amino acid sequence at least 80% identical to SEQ ID NO: 5, and a heavy chain complementarity determining region 3 (CDR3) having an amino acid sequence at least 80% identical to SEQ ID NO: 6. In some instances, the monoclonal antibody or antigen-binding fragment thereof comprises at least one of a heavy chain complementarity determining region 1 (CDR1) having an amino acid sequence at least 80% identical to SEQ ID NO: 12, a heavy chain complementarity determining region 2 (CDR2) having an amino acid sequence at least 80% identical to SEQ ID NO: 13, and a heavy chain complementarity determining region 3 (CDR3) having an amino acid sequence at least 80% identical to SEQ ID NO: 14. In some instances, the monoclonal antibody or antigen-binding fragment thereof comprises at least one of a heavy chain complementarity determining region 1 (CDR1) having an amino acid sequence at least 80% identical to SEQ ID NO: 4, a heavy chain complementarity determining region 2 (CDR2) having an amino acid sequence at least 80% identical to SEQ ID NO: 18, and a heavy chain complementarity determining region 3 (CDR3) having an amino acid sequence at least 80% identical to SEQ ID NO: 6. In some instances, the monoclonal antibody or antigen-binding fragment thereof comprises a light chain variable domain (VL) comprising an amino acid sequence at least 80% identical to an amino acid sequence set forth as SEQ ID NO: 7, SEQ ID NO: 15, SEQ ID NO: 19. In some instances, the monoclonal antibody or antigen-binding fragment thereof comprises a heavy chain variable domain (VH) comprising an amino acid sequence at least 80% identical to an amino acid sequence set forth as SEQ ID NO: 8, SEQ ID NO:16, or SEQ ID NO: 20. In some instances, the monoclonal antibody or antigen-binding fragment thereof comprises a light chain variable domain (VL) comprising an amino acid sequence at least 80% identical to an amino acid sequence set forth as SEQ ID NO: 7, SEQ ID NO: 15, or SEQ ID NO: 19; and a heavy chain variable domain (VH) comprising an amino acid sequence at least 80% identical to an amino acid sequence set forth as SEQ ID NO: 8. SEQ ID NO: 16, or SEQ ID NO: 20. In some instances, the monoclonal antibody or antigen-binding fragment thereof comprises a light chain variable domain (VL) comprising an amino acid sequence at least 80% identical to SEQ ID NO: 7 and a heavy chain variable domain (VH) comprising an amino acid sequence at least 80% identical to SEQ ID NO: 8. In some instances, the monoclonal antibody or antigen-binding fragment thereof comprises a light chain variable domain (VL) comprising an amino acid sequence at least 80% identical to SEQ ID NO: 15 and a heavy chain variable domain (VH) comprising an amino acid sequence at least 80% identical to SEQ ID NO: 16. In some instances, the monoclonal antibody or antigen-binding fragment thereof comprises a light chain variable domain (VL) comprising an amino acid sequence at least 80% identical to SEQ ID NO: 19 and a heavy chain variable domain (VH) comprising an amino acid sequence at least 80% identical to SEQ ID NO: 20. In some instances, the monoclonal antibody or antigen-binding fragment thereof comprises a light chain comprising an amino acid sequence at least 80% identical to an amino acid sequence set forth as SEQ ID NO: 21. SEQ ID NO: 23, or SEQ ID NO: 24. In some instances, the monoclonal antibody or antigen-binding fragment thereof comprises a heavy chain comprising an amino acid sequence at least 80% identical to an amino acid sequence set forth as SEQ ID NO: 22, SEQ ID NO: 25, or SEQ ID NO: 26. In some instances, the monoclonal antibody or antigen-binding fragment thereof specifically binds to a MICA protein, a MICB protein, or both MICA and MICB protein. In some instances, the monoclonal antibody or antigen-binding fragment thereof binds to an alpha-3 domain of a MICA protein, a MICB protein, or both MICA and MICB protein. In some instances, the MICA protein is membrane-bound MICA protein, soluble MICA protein, or both. In some instances, the MICB protein is membrane-bound MICB protein, soluble MICB protein, or both. In some instances, the monoclonal antibody or antigen-binding fragment thereof is selected from a whole immunoglobulin, an scFv, a Fab, a F(ab')$_2$, or a disulfide linked Fv. In some instances, the monoclonal antibody or antigen-binding fragment thereof is an IgG or IgM. In some instances, the monoclonal antibody or fragment thereof is humanized or chimeric. In some instances, the monoclonal antibody or antigen-binding fragment thereof reduces or inhibits shedding of soluble MICA protein, soluble MICB protein, or both, thereby reducing level of soluble MICA protein, soluble MICB protein, or both in the individual. In some instances, the individual has a cancer characterized by elevated levels of soluble MICA protein, soluble MICB protein, or both. In some instances, the cancer is hepatocellular carcinoma.

Disclosed herein, in certain embodiments, are monoclonal antibodies or an antigen-binding fragments thereof according to any one of disclosures herein for use in treating cancer in an individual in need thereof. Disclosed herein, in certain embodiments, are monoclonal antibodies or an antigen-binding fragments thereof according to any one of disclosures herein for use in preparation of a medicament for treating cancer in an individual in need thereof. In some instances, the cancer is hepatocellular carcinoma.

Disclosed herein, in certain embodiments, are monoclonal antibodies or an antigen-binding fragments thereof that competitively bind to MICA/B with an antibody comprising a light chain variable domain (VL) having an amino acid sequence at least about 80% identical to an amino acid sequence set forth as SEQ ID NO: 27. Disclosed herein, in certain embodiments, are monoclonal antibodies or an antigen-binding fragments thereof that competitively bind to MICA/B with an antibody comprising a heavy chain variable domain (VH) having an amino acid sequence at least about 80% identical to an amino acid sequence set forth as SEQ ID NO: 28.

BRIEF DESCRIPTION OF THE DRAWINGS

An understanding of the features and advantages of the present invention will be obtained by reference to the following detailed description that sets forth illustrative embodiments, in which the principles of the invention are utilized, and the accompanying drawings of which.

DETAILED DESCRIPTION

Figure 1A:
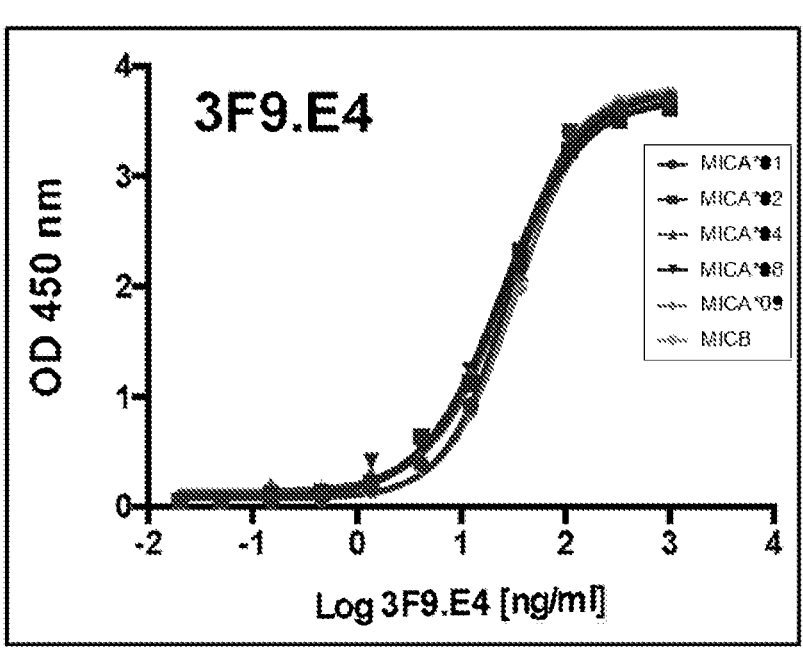
FIG. 1A-FIG. 1B exemplify binding of antibodies 3F9.E4 (FIG. 1A) and 16F10.C12 (FIG. 1B) to MICA/B alleles by ELISA.

Disclosed herein, in some embodiments, are monoclonal antibodies that bind specifically to MICA/B. In some embodiments, MICA/B antibodies herein bind to MICA/B proteins or fragments thereof and modulate immune response in an individual, thereby treating cancer (e.g. hepatocellular carcinoma).

Major histocompatibility complex class I-related chain A and B (MICA/B) are two stress-inducible ligands for natural killer cell (NK) receptor NKG2D and play an important role in mediating the cytotoxicity of NK and T cells. Soluble MICA/B shed by diseased cells (e.g. cancer cells) desensitizes NK and T cells through binding of NKG2D receptor, thereby suppressing the immune response. Accordingly, modulation of MICA/B is useful in modulating an immune response in an individual, for example, in an individual suffering from cancer. Antibodies binding to MICA/B and modulating its activity are desirable for the development of novel therapeutics for treatment of cancer.

Certain Terminology

As used herein "MICA/B" refers to MICA protein, MICB protein or both MICA and MICB proteins, including their variants, isoforms, and species homologs of human MICA/B.

As used herein "antibody" refers to a glycoprotein which exhibits binding specificity to a specific antigen. An antibody often comprises a variable domain and a constant domain in each of a heavy chain and a light chain. Accordingly, most antibodies have a heavy chain variable domain (VH) and a light chain variable domain (VL) that together form the portion of the antibody that binds to the antigen. Within each variable domain are three complementarity determining regions (CDR) which form loops in the heavy chain variable domain (VH) and light chain variable domain (VL) that contact the surface of the antigen. Antibodies herein also include "antigen binding portion" or fragments of the antibody that are capable of binding to the antigen.

As used herein "chimeric" antibodies are antibodies having a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see e.g., Morrison et al., Proc. Natl. Acad. Sci. USA 81:6851-6855 (1984)). "Humanized antibodies" herein refers chimeric antibodies having human sequences substituted in the antibody sequence.

The terms "recipient", "individual", "subject", "host", and "patient", are used interchangeably herein and in some cases, refer to any mammalian subject for whom diagnosis, treatment, or therapy is desired, particularly humans. "Mammal" for purposes of treatment refers to any animal classified as a mammal, including humans, domestic and farm animals, and laboratory, zoo, sports, or pet animals, such as dogs, horses, cats, cows, sheep, goats, pigs, mice, rats, rabbits, guinea pigs, monkeys etc. In some embodiments, the mammal is human.

As used herein, the terms "treatment," "treating." and the like, in some cases, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a disease or disorder (e.g. cancer) in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease: (b) inhibiting the disease. i.e., arresting its development; and (c) relieving the disease, i.e., causing regression of the disease. Treating may refer to any indicia of success in the treatment or amelioration or prevention of a cancer, including any objective or subjective parameter such as abatement: remission; diminishing of symptoms or making the disease condition more tolerable to the patient; slowing in the rate of degeneration or decline; or making the final point of degeneration less debilitating. The treatment or amelioration of symptoms is based on one or more objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with diseases (e.g. cancer). The term "therapeutic effect" refers to the reduction, elimination, or prevention of the disease, symptoms of the disease, or side effects of the disease in the subject.

A "therapeutically effective amount" in some cases means the amount that, when administered to a subject for treating a disease, is sufficient to effect treatment for that disease.

As used herein, singular forms "a", "and," and "the" include plural referents unless the context clearly indicates otherwise. Thus, for example, reference to "an antibody" includes a plurality of antibodies and reference to "an antibody" in some embodiments includes multiple antibodies, and so forth.

As used herein, all numerical values or numerical ranges include whole integers within or encompassing such ranges and fractions of the values or the integers within or encompassing ranges unless the context clearly indicates otherwise. Thus, for example, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.39%, 92.4%, 92.5%, etc., and so forth. In another example, reference to a range of 1-5,000 fold includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and so forth.

"About" a number, as used herein, refers to range including the number and ranging from 10% below that number to 10% above that number. "About" a range refers to 10% below the lower limit of the range, spanning to 10% above the upper limit of the range.

Percent (%) identity" refers to the extent to which two sequences (nucleotide or amino acid) have the same residue at the same positions in an alignment. For example, "an amino acid sequence is X % identical to SEQ ID NO. Y" refers to % identity of the amino acid sequence to SEQ ID NO:Y and is elaborated as X % of residues in the amino acid sequence are identical to the residues of sequence disclosed in SEQ ID NO: Y. Generally, computer programs are employed for such calculations. Exemplary programs that compare and align pairs of sequences, include ALIGN (Myers and Miller, 1988). FASTA (Pearson and Lipman, 1988; Pearson, 1990) and gapped BLAST (Altschul et al., 1997). BLASTP, BLASTN, or GCG (Devereux et al., 1984).
MICA/B Disclosed herein, in some embodiments, are monoclonal antibodies that bind specifically to MICA/B. Further disclosed herein, in some embodiments, are monoclonal antibodies that competitively bind to MICA/B.

Major Histocompatibility Complex (MHC) class I Chain-related gene A and gene B protein (MICA/B) are glycosylated, polymorphic and membrane-anchored non-classical MHC class I proteins. MICA/B are related to MHC class I and have similar domain structure comprising three extracellular Ig-like domains (alpha-1, alpha-2 and alpha-3), a transmembrane domain and a C-terminal cytoplasmic tail. However, MICA/B do not associate with β2-microglobulin, lack a CD8 binding site and do not present any antigens. MICA/B are ligands to C-type lectin-like activating receptor Natural Killer Group 2D (NKG2D) on immune effector cells, including NK, NKT and both αβ and γδ CD8+ T cells. The interaction of MICA/B and NKG2D plays a role in tumor surveillance, and immune response.

MICA/B proteins are expressed normally at low levels in normal cells, but are induced to higher levels in stressed or transformed cells (e.g. cancer cells). The interaction of NKG2D-bearing immune effector cells with stressed or diseased cells expressing MICA/B ligands on the cell surface creates a cellular immune response against the stressed/diseased cell that culminates in the death of the MICA/B expressing cells. In cancer cells, the truncated MICA/B proteins (proteins that lack the transmembrane domain and cytoplasmic tail but retain the three extracellular domain comprising alpha-1, -2 and -3 domains) are frequently shed into the blood by the action of proteases and results in the down-modulation (receptor internalization) of its intended receptor. NKG2D, on effector immune cells. In some instances, MICA/B glycoproteins are produced intracellularly that are not routinely destined to become cell surface membrane-bound, but instead are incorporated within exosomes and released outside the cell where interaction with NKG2D receptors on immune cells occurs. These truncated or soluble MICA/B ligands shed from the surface of cancer cells function like decoy molecules and lead to down-modulation of the NKG2D receptor on immune effector cells such as NK, NKT and various CD8+ T cells. In some instances, the formation of soluble MICA/B leads to the unusual situation where the effectors of the innate defense system, whose natural role is to seek and destroy transformed cells, are shut down by the immunosuppressive actions of these decoy ligand molecules, thereby enabling the cancer cells to hide from the immune system and to grow unchecked.

Hepatocellular Carcinoma (HCC)

In some embodiments, anti-MICA/B antibodies disclosed herein bind to MICA/B proteins or fragments thereof and modulate immune response in an individual, thereby treating cancer (e.g. hepatocellular carcinoma).

Hepatocellular carcinoma (HCC) is a primary malignancy of the liver and occurs predominantly in individuals with underlying chronic liver disease and cirrhosis. Tumors progress with local expansion, intrahepatic spread, and distant metastases, Hepatitis B and Hepatitis C predisposes individuals to the development of chronic liver disease and subsequent development of HCC. Obesity, diabetes, and alcohol abuse are some other causes that predispose individuals to the subsequent development of HCC.

Anti-MICA/B Antibodies

Provided herein are antibodies that specifically bind to MICA/B proteins. In some embodiments, anti-MICA/B antibodies comprise at least one heavy chain and anti-MICA/B antibodies comprise at least one light chain. In some embodiments, anti-MICA/B antibodies comprise at least one heavy chain comprising a heavy chain variable domain (VH) and at least one light chain comprising a light chain variable domain (VL). Each VH and VL comprises three complementarity determining regions (CDR). The amino acid sequences of the VH and VL and the CDRs determine the antigen binding specificity and antigen binding strength of the antibody. The amino acid sequences of the Heavy and Light chains, VH and VL and the CDRs are summarized in Table 1.

TABLE 1

| Anti-MICA/B Monoclonal Antibody Sequences | | |
| --- | --- | --- |
| | SEQUENCE | SEQ ID NO: |
| 3F9.E4 Light Chain CDR1 | RSSKSLLHSNGNTYLY | 1 |
| 3F9.E4 Light Chain CDR2 | RMSNLAS | 2 |
| 3F9.E4 Light Chain CDR3 | MQHLEYPFT | 3 |
| 3F9.E4 Heavy Chain CDR1 | GFTFSNYAMS | 4 |
| 3F9.E4 Heavy Chain CDR2 | YISPGGDYIYYADTVKG | 5 |
| 3F9.E4 Heavy Chain CDR3 | DRRHYGSYAMDY | 6 |
| 3F9.E4 Light Chain Variable domain | DIVMTQAAPSVPVTPGESVSISCRSSKSLLHSNGNTYLYWFLQRPGQS PQLLIYRMSNLASGVPDRFSGSGSGTAFTLRISRVEAEDVGVYYCMQ HLEYPFTFGSGTKLEIK | 7 |
| 3F9.E4 Heavy Chain Variable domain | EVQLQESGEGLVKPGGSLKLSCAASGFTESNYAMSWVROTPEKRLE WVAYISPOGODYIYYADTVKGRFTISRDNARNTLYLOMSSLKSEDTA MYYCTTDRRHYGSYAMDYWGQGISVTVSS | 8 |
| 16F10.C12 Light Chain CDR1 | TASSSVSSNYLH | 9 |

TABLE 1-continued

Anti-MICA/B Monoclonal Antibody Sequences

| | SEQUENCE | SEQ ID NO: |
|---|---|---|
| 16F10.C12 Light Chain CDR2 | TTSNLAS | 10 |
| 16F10.C12 Light Chain CDR3 | HQFHRSPFT | 11 |
| 16F10.C12 Heavy Chain CDR1 | GFSLTAFGVN | 12 |
| 16F10.C12 Heavy Chain CDR2 | MIWGDGNTDYNSTLRS | 13 |
| 16F10.C12 Heavy Chain CDR3 | ETYYGNYAGLGY | 14 |
| 16F10.C12 Light Chain Variable domain | QIVLTQSPAIMSASIGERVTMTCTASSSVSSNYLHWYQQKPRSSPKL WIYYTTSNLASGVPTRFSGSGSGTSYSLTISSMEAEDAATYYCHQFHRS PFTFGSGTKLEIK | 15 |
| 16F10.C12 Heavy Chain Variable domain | EVQLQESGPGLVAPSQSLSITCTVSGFSLTAFGVNWVRQPPGKGLEW LGMIWGDGNTDYNSTLRSRLSISKDNSKSQVFLKLNSLQTDDTARYF CARETYYGNYAGLGYWGQGTLVTVSA | 16 |
| 3F9HIL3L Light Chain CDR1 | RSSKSLLHSNLNTYLY | 17 |
| 3F9HIL3L Light Chain CDR2 | RMSNLAS | 2 |
| 3F9HIL3L Light Chain CDR3 | MQHLEYPFT | 3 |
| 3F9HIL3L Heavy Chain CDR1 | GFTFSNYAMS | 4 |
| 3F9HIL3L Heavy Chain CDR2 | YISPGGDYTYYADSVKG | 18 |
| 3F9HIL3L Heavy Chain CDR3 | DRRHYGSYAMDY | 6 |
| 3F9HIL3L Light Chain Variable domain | DIVMTQSPLSLPVTPGEPASISCRSSKSLLHSNLNTYLYWFLQKPGQS PQILIYRMSNLASGVPDRFSGSGSGTAFTLKISRVEAEDVGVYYCMQ HLEYPFTPGPGTKLEIKR | 19 |
| 3P9HIL3L Heavy Chain Variable domain | QVQLVESGGGLVKPGGSLRLSCAASGFTFSNYAMSWIRQAPGKGLE WVSYISPGGDYIYYADSVKGRFTISRDNAKNSLYLQMNSLRAEDTA VYYCTT | 20 |
| 3F9HIL3L Light Chain | DIVMTQSPLSLPVTPGEPASISCRSSKSLLHSNLNTYLYWFLQKPGQS PQILIYRMSNLASGVPDRFSGSGSGTAFTLKISRVEAEDVGVYYCMQ HLEYPFTFGPGTKLEIKRTVAAPSVFIFPPSDEQLKSGTASVVCLLNNF YPREAKVQWKVDNALQSGNSQESVTEQDSKDSTYSLSSTLTLSKAD YEKHKVYACEVTHQGLSSPVTKSFNRGEC* | 21 |
| 3F9HIL3L Heavy Chain | QVQLVESGGGLVKPGGSLRLSCAASGFTFSNYAMSWIRQAPGKGLE WVSYISPGGDYIYYADSVKGRFTISRDNAKNSLYLQMNSLRAEDTA VYYCTTDRRHYGSYAMDYWGQGTLVTVSSASTKGPSVFPLAPSSKS TSGGTAALGCLVKDYFPEPVTVSWNSGALTSGVHTFPAVLQSSGLYS LSSVVTVPSSSLGTQTYICNVNHKPSNTKVDKKVEPKSCDKTHTCPP CPAPELLGGPSVFLFPPKPKDTLMISRTPEVTCVVVDVSHEDPEVKFN WYVDGVEVHNAKTKPREEQYNSTYRVVSVLTVLHQDWLNGKEYK CKVSNKALPAPIEKTISKARGQPREPQVYTLPPSREEMTKNQVSLTCL VKGFYPSDIAVEWESNGQPENNYKTTPPVLDSDGSFFLYSKLTVDKS RWQQGNVFSCSVMHEALHNHYTQKSLSLSPG** | 22 |
| PDI-1 humanized LC5 Light Chain | METDTLLLWVLLLWVPGSTGDIQMTQSPSTLSASVGDRVTITCSASQ GISNYLNWYQQKPGKAPKLLIQYTSLLHSGVPSRPSGSGSGTEYTLTI SSLQPDDFATYFCQQYSKFFRTFGGGTKVEIKRTVAAPSVFIFPPSDE QLKSGTASVVCLLNNFYPREAKVQWKVDNALQSGNSQESVTEQDS KDSTYSLSSTLTLSKADYEKHKVYACEVTHQGLSSPVTKSFNRGEC* | 23 |

TABLE 1-continued

Anti-MICA/B Monoclonal Antibody Sequences

| | SEQUENCE | SEQ ID NO: |
|---|---|---|
| PDI-1 humanized LC4 Light Chain | METDTLLLWVLLLWVPGSTGDIQMTQSPSSLSASVGDRVTITCSASQ GISNYLNWYQQKPGKAPKLLIQYTSLLHSGVPSRFSGSGSGTDYTLTI SSLQPEDFATYFCQQYSKFPRTFGGGTKVEIKRTVAAPSVFIFPPSDEQ LKSGTASVVCLLNNFYPREAKVQWKVDNALQSGNSQESVTEQDSK DSTYSLSSTLTLSKADYEKHKVYACEVTHQGLSSPVTKSFNRGEC* | 24 |
| PDI-1 humanized HC4 Heavy Chain | MDPKGSLSWRILLFLSLAFELSYGQIQLVQSGSELKKPGASVKVSCK AFGYTFTNYGMNWVKQAPGQGLKWMGWINTYTGEPTYAQGFTGR FVFSLETSVSTAYLQISSLKAEDTAVYFCARNYGNYLFDYWGQGTL VTVSSASTKGPSVFPLAPSSKSTSGGTAALGCLVKDYFPEPVTVSWN SGALTSGVHTFPAVLQSSGLYSLSSVVTVPSSSLGTQTYICNVNHKPS NTKVDKKVEPKSCDKTHTCPPCPAPELLGGPSVFLFPPKPKDTLMISR TPEVTCVVVDVSHEDPEVKFNWYVDGVEVHNAKTKPREEQYNSTY RVVSVLTVLHQDWLNGKEYKCKVSNKALPAPIEKTISKAKGQPREP QVYTLPPSREEMTKNQVSLTCLVKGFYPSDIAVEWESNGQPENNYK TTPPVLDSDGSFFLYSKLTVDKSRWQQGNFSCSVMHEALHNHYTQ KSLSLSPG* | 25 |
| PDI-1 humanized HC6 Heavy Chain | MDPKGSLSWRILLFLSLAFELSYGQIQLVQSGAEVKKPGASVKVSCK AFGYTFTNYGMNWVKQAPGQGLKWMGWINTYTGEPTYADDFKGR VTFTLETSISTAYMELSRLRSDDTAVYFCARNYGNYLFDYWGQGTL VTVSSASTKGPSVFPLAPSSKSTSGGTAALGCLVKDYFPEPVTVSWN SGALTSGVHTFPAVLQSSGLYSLSSVVTVPSSSLGTQTYICNVNHKPS NTKVDKKVEPKSCDKTHTCPPCPAPELLGGPSVFLFPPKPKDTLMISR TPEVTCVVVDVSHEDPEVKFNWYVDGVEVHNAKTKPREEQYNSTY RVVSVLTVLHQDWLNGKEYKCKVSNKALPAPIEKTISKAKGQPREP QVYTLPPSREEMTKNQVSLTCLVKGFYPSDIAVEWESNGQPENNYK TTPPVLDSDGSFFLYSKLTVDKSRWQQGNFSCSVMHEALHNHYTQ KSLSLSPG* | 26 |
| PDI-1 Light Chain Variable domain | DIQMTQTTSSLSASLGDRVTISCSASQGISNYLNWYQQKPD GTLKLLIQYTSLLHSGVPSRFSGSGSGTEYSLTISNLEPEDIAT YFCQQYSKFPRT FGGGTKLEIKR | 27 |
| PDI-1 Heavy Chain Variable domain | QIQLVQSGPELKKSGETVKISCKAFGYTFTNYGMNWVKQA PGKGLKMGWINTYTGEPTYADDFKGRFAFSLETSASTAYL QINHLKNEDTATYFCARNYGNYLFDYWGQGTTLTVSS | 28 |

In some embodiments, the antibodies specifically bind to a MICA protein. In some embodiments, the antibodies specifically bind to a MICB protein. In some embodiments, the antibodies specifically bind to both MICA and MICB protein. In some embodiments, the antibodies bind to an alpha-3 domain of a MICA protein. In some embodiments, the antibodies bind to an alpha-3 domain of a MICB protein. In some embodiments, the antibodies bind to an alpha-3 domain of both MICA and MICB protein. In some embodiments, the antibodies bind to a MICA protein that is membrane-bound MICA protein. In some embodiments, the antibodies bind to a MICA protein that is soluble MICA protein. In some embodiments, the antibodies bind to a MICA protein that is both membrane-bound MICA protein and soluble MICA protein. In some embodiments, the antibodies bind to a MICB protein that is membrane-bound MICB protein. In some embodiments, the antibodies bind to a MICB protein that is soluble MICB protein. In some embodiments, the antibodies bind to a MICB protein that is both membrane-bound MICB protein and soluble MICB protein.

In some embodiments, antibodies that specifically bind to MICA/B are monoclonal antibodies. In some embodiments, the antibody is an antigen binding fragment. In some embodiments, the antibody is selected from a whole immunoglobulin, an seFv, a Fab, a F(ab')2, or a disulfide linked Fv. In some embodiments, the antibody is an IgG or an IgM. In some embodiments, the antibody is humanized. In some embodiments, the antibody is chimeric.

MICA/B Antibody Heavy and Light Chain

Disclosed herein are antibodies that specifically bind to MICA/B having a light chain. In some embodiments, antibodies binding to MICA/B comprise a light chain having an amino acid sequence at least about 70% identical to an amino acid sequence set forth as SEQ ID NO: 21, SEQ ID NO: 23, or SEQ ID NO: 24. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 21, SEQ ID NO: 23, or SEQ ID NO: 24. In some embodiments, the light chain has an amino acid sequence 100% identical to an amino acid sequence set forth as SEQ ID NO: 21, SEQ ID NO: 23, or SEQ ID NO: 24.

Further disclosed herein are antibodies that specifically bind to MICA/B having a heavy chain. In some embodiments, antibodies binding to MICA/B comprise a heavy chain having an amino acid sequence at least about 70% identical to an amino acid sequence set forth as SEQ ID NO: 22, SEQ ID NO: 25, or SEQ ID NO: 26. In some embodiments the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 22, SEQ ID NO: 25, or SEQ ID NO: 26. In some embodiments, the heavy chain has an amino acid sequence 100% identical to an amino acid sequence set forth as SEQ ID NO: 22, SEQ ID NO: 25, or SEQ ID NO: 26.

Also disclosed herein are antibodies binding to MICA/B comprising a light chain and a heavy chain. In some embodiments, antibodies binding to MICA/B comprise a light chain having an amino acid sequence at least about 70% identical to an amino acid sequence set forth as SEQ ID NO: 21, SEQ ID NO: 23, or SEQ ID NO: 24 and a heavy chain having an amino acid sequence at least about 70% identical to an amino acid sequence set forth as SEQ ID NO: 22, SEQ ID NO: 25, or SEQ ID NO: 26. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 21. SEQ ID NO: 23, or SEQ ID NO: 24 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 22. SEQ ID NO: 25, or SEQ ID NO: 26. In some embodiments, the light chain has an amino acid sequence 100% identical to an amino acid sequence set forth as SEQ ID NO: 21, SEQ ID NO: 23, or SEQ ID NO: 24 and the heavy chain has an amino acid sequence 100% identical to an amino acid sequence set forth as SEQ ID NO: 22, SEQ ID NO: 25, or SEQ ID NO: 26, In some embodiments, antibodies binding to MICA/B comprise a light chain having an amino acid sequence at least about 70% identical to an amino acid sequence set forth as SEQ ID NO: 21 and a heavy chain having an amino acid sequence at least about 70% identical to an amino acid sequence set forth as SEQ ID NO: 22. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 21 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 22. In some embodiments, the light chain has an amino acid sequence 100% identical to an amino acid sequence set forth as SEQ ID NO: 21 and the heavy chain has an amino acid sequence 100% identical to an amino acid sequence set forth as SEQ ID NO: 22.

In some embodiments, antibodies binding to MICA/B comprise a light chain having an amino acid sequence at least about 70% identical to an amino acid sequence set forth as SEQ ID NO: 23 and a heavy chain having an amino acid sequence at least about 70% identical to an amino acid sequence set forth as SEQ ID NO: 25. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 23 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 25. In some embodiments, the light chain has an amino acid sequence 100% identical to an amino acid sequence set forth as SEQ ID NO: 23 and the heavy chain has an amino acid sequence 100% identical to an amino acid sequence set forth as SEQ ID NO: 25.

In some embodiments, antibodies binding to MICA/B comprise a light chain having an amino acid sequence at least about 70% identical to an amino acid sequence set forth as SEQ ID NO: 23 and a heavy chain having an amino acid sequence at least about 70% identical to an amino acid sequence set forth as SEQ ID NO: 26. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 23 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 26. In some embodiments, the light chain has an amino acid sequence 100% identical to an amino acid sequence set forth as SEQ ID NO: 23 and the heavy chain has an amino acid sequence 100% identical to an amino acid sequence set forth as SEQ ID NO: 26.

In some embodiments, antibodies binding to MICA/B comprise a light chain having an amino acid sequence at least about 70% identical to an amino acid sequence set forth as SEQ ID NO: 24 and a heavy chain having an amino acid sequence at least about 70% identical to an amino acid sequence set forth as SEQ ID NO: 25. In some embodiments the light chain has an amino acid sequence at least about 75%, 80%, 81%, 82%, 83%, 84%, 85%, 86%, 87%, 88%, 89%, 90%, 91%, 92%, 93%, 949%, 95%, 96%, 97%, 98%, or 99% identical to an amino acid sequence set forth as SEQ ID NO: 24 and the heavy chain has an amino acid sequence at least about 75%, 80%, 81%, 82%, 83%, 84%, 85%, 86%, 87%, 88%, 89%, 90%, 919%, 92%, 93%, 94%, 95%, 96%, 97%, 98%, or 99% identical to an amino acid sequence set forth as SEQ ID NO: 25. In some embodiments, the light chain has an amino acid sequence 100% identical to an amino acid sequence set forth as SEQ ID NO: 24 and the heavy chain has an amino acid sequence 100% identical to an amino acid sequence set forth as SEQ ID NO: 25.

In some embodiments, antibodies binding to MICA/B comprise a light chain having an amino acid sequence at least about 70% identical to an amino acid sequence set forth as SEQ ID NO: 24 and a heavy chain having an amino acid sequence at least about 70% identical to an amino acid sequence set forth as SEQ ID NO: 26. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 24 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 26. In some embodiments, the light chain has an amino acid sequence 100% identical to an amino acid sequence set forth as SEQ ID NO: 24 and the heavy chain has an amino acid sequence 100% identical to an amino acid sequence set forth as SEQ ID NO: 26.

MICA/B Antibody Variable Domain

Disclosed herein are antibodies that specifically bind to MICA/B having a light chain comprising a light chain variable domain (VL). In some embodiments, antibodies binding to MICA/B comprise a light chain variable domain (VL) having an amino acid sequence at least about 70% identical to an amino acid sequence set forth as SEQ ID NO: 7. SEQ ID NO: 15, or SEQ ID NO: 19. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7. SEQ ID NO: 15, or SEQ ID NO: 19. In some embodiments, the VL has an amino acid sequence 100% identical to an amino acid sequence set forth as SEQ ID NO: 7, SEQ ID NO: 15, or SEQ ID NO: 19.

Further disclosed herein are antibodies that specifically bind to MICA/B having a heavy chain comprising a heavy chain variable domain (VH). In some embodiments, antibodies binding to MICA/B comprise a heavy chain variable domain (VH) having an amino acid sequence at least about 70% identical to an amino acid sequence set forth as SEQ ID NO: 8, SEQ ID NO: 16, or SEQ ID NO: 20. In some embodiments the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8. SEQ ID NO: 16, or SEQ ID NO: 20. In some embodiments, the VH has an amino acid sequence 100% identical to an amino acid sequence set forth as SEQ ID NO: 8, SEQ ID NO: 16, or SEQ ID NO: 20.

Also disclosed herein are antibodies binding to MICA/B comprising a light chain variable domain (VL) and a heavy chain variable domain (VH). In some embodiments, antibodies binding to MICA/B comprise a light chain variable domain (VL) having an amino acid sequence at least about 70% identical to an amino acid sequence set forth as SEQ ID NO: 7, SEQ ID NO: 15, or SEQ ID NO: 19 and a heavy chain variable domain (VH) having an amino acid sequence at least about 70% identical to an amino acid sequence set forth as SEQ ID NO: 8. SEQ ID NO: 16, or SEQ ID NO: 20. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7, SEQ ID NO: 15, or SEQ ID NO: 19 and the VH has an amino acid sequence at least about 75%, 80%, 81%, 82%, 83%, 84%, 85%, 86%, 87%, 88%, 89%, 90%, 919%, 92%, 93%, 94%, 95%, 96%, 97%, 98%, or 99% identical to an amino acid sequence set forth as SEQ ID NO: 8, SEQ ID NO: 16, or SEQ ID NO: 20. In some embodiments, the VL has an amino acid sequence 100% identical to an amino acid sequence set forth as SEQ ID NO: 7, SEQ ID NO: 15, or SEQ ID NO: 19 and the VH has an amino acid sequence 100% identical to an amino acid sequence set forth as SEQ ID NO: 8, SEQ ID NO: 16, or SEQ ID NO: 20.

In some embodiments, antibodies binding to MICA/B comprise a light chain variable domain (VL) having an amino acid sequence at least about 70% identical to an amino acid sequence set forth as SEQ ID NO: 7 and a heavy chain variable domain (VH) having an amino acid sequence at least about 70% identical to an amino acid sequence set forth as SEQ ID NO: 8. In some embodiments the VL has an amino acid sequence at least about 75%, 80%, 81%, 82%, 83%, 84%, 85%, 86%, 87%, 88%, 89%, 90%, 919%, 92%, 93%, 94%, 95%, 96%, 97%, 98%, or 99% identical to an amino acid sequence set forth as SEQ ID NO: 7 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8. In some embodiments, the VL has an amino acid sequence 100% identical to an amino acid sequence set forth as SEQ ID NO: 7 and the VH has an amino acid sequence 100% identical to an amino acid sequence set forth as SEQ ID NO: 8.

In some embodiments, antibodies binding to MICA/B comprise a light chain variable domain (VL) having an amino acid sequence at least about 70% identical to an amino acid sequence set forth as SEQ ID NO: 15 and a heavy chain variable domain (VH) having an amino acid sequence at least about 70% identical to an amino acid sequence set forth as SEQ ID NO: 16. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 15 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 16. In some embodiments, the VL has an amino acid sequence 100% identical to an amino acid sequence set forth as SEQ ID NO: 15 and the VH has an amino acid sequence 100% identical to an amino acid sequence set forth as SEQ ID NO: 16.

In some embodiments, antibodies binding to MICA/B comprise a light chain variable domain (VL) having an amino acid sequence at least about 70% identical to an amino acid sequence set forth as SEQ ID NO: 19 and a heavy chain variable domain (VH) having an amino acid sequence at least about 70% identical to an amino acid sequence set forth as SEQ ID NO: 20. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 19 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 20. In some embodiments, the VL has an amino acid sequence 100% identical to an amino acid sequence set forth as SEQ ID NO: 19 and the VH has an amino acid sequence 100% identical to an amino acid sequence set forth as SEQ ID NO: 20.

MICA/B Antibody Complementarity Determining Regions

Disclosed herein are antibodies that specifically bind to MICA/B having a light chain comprising a light chain complementarity determining region (CDR). In some embodiments, antibodies binding to MICA/B comprise a light chain CDR sequence having an amino acid sequence at least about 70% identical to at least one of the amino acid sequences set forth as SEQ ID NOS: 1-3, 9-11, and 17. In some embodiments, antibodies binding to MICA/B comprise a light chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 1-3, 9-11, and 17. In some embodiments, antibodies binding to MICA/B comprise a light chain CDR sequence having an amino acid sequence 100% identical to at least one of the amino acid sequences set forth as SEQ ID NOS: 1-3, 9-11, and 17.

Further disclosed herein are antibodies that specifically bind to MICA/B having a heavy chain comprising a heavy chain complementarity determining region (CDR). In some embodiments, antibodies binding to MICA/B comprise a heavy chain CDR sequence having an amino acid sequence at least about 70% identical to at least one of the amino acid sequences set forth as SEQ ID NOS: 4-6, 12-14, and 18. In some embodiments, antibodies binding to MICA/B comprise a heavy chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 4-6, 12-14, and 18. In some embodiments, antibodies binding to MICA/B comprise a heavy chain CDR sequence having an amino acid sequence 100% identical to at least one of the amino acid sequences set forth as SEQ ID NOS: 4-6, 12-14, and 18.

Also disclosed herein are antibodies binding to MICA/B comprising a light chain complementarity determining region (CDR) and a heavy chain complementarity determining region (CDR). In some embodiments, antibodies binding to MICA/B comprise a light chain CDR sequence having an amino acid sequence at least about 70% identical to at least one of the amino acid sequences set forth as SEQ ID NOS: 1-3, 9-11, and 17 and a heavy chain CDR sequence having an amino acid sequence at least about 70% identical to at least one of the amino acid sequences set forth as SEQ ID NOS: 4-6, 12-14, and 18. In some embodiments, antibodies binding to MICA/B comprise a light chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 1-3, 9-11, and 17 and a heavy chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 4-6, 12-14, and 18. In some embodiments, antibodies binding to MICA/B comprise a light chain CDR sequence having an amino acid sequence 100% identical to at least one of the amino acid sequences set forth as SEQ ID NOS: 1-3, 9-11, and 17 and a heavy chain CDR sequence having an amino acid sequence at least about 100% identical to at least one of the amino acid sequences set forth as SEQ ID NOS: 4-6, 12-14, and 18.

In some embodiments, antibodies binding to MICA/B comprise a light chain complementarity determining region 1 (CDR1) having an amino acid sequence at least about 70% identical to one of SEQ ID NO: 1, SEQ ID NO: 9, or SEQ ID NO: 17, a light chain complementarity determining region 2 (CDR2) having an amino acid sequence at least about 70% identical to one of SEQ ID NOS: SEQ ID NO: 2, or SEQ ID NO: 10, a light chain complementarity determining region 3 (CDR3) having an amino acid sequence at least about 70% identical to one of SEQ ID NO: 3, or SEQ ID NO: 11, a heavy chain complementarity determining region 1 (CDR1) having an amino acid sequence at least about 70% identical to one of SEQ ID NO: 4, or SEQ ID NO: 12, a heavy chain complementarity determining region 2 (CDR2) having an amino acid sequence at least about 70% identical to one of SEQ ID NO: 5, SEQ ID NO: 13, or SEQ ID NO: 18, and a heavy chain complementarity determining region 3 (CDR3) having an amino acid sequence at least about 70% identical to one of SEQ ID NO: 6, or SEQ ID NO: 14. In some embodiments, antibodies binding to MICA/B comprise a light chain complementarity determining region 1 (CDR1) having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to one of SEQ ID NO: 1. SEQ ID NO: 9, or SEQ ID NO: 17, a light chain complementarity determining region 2 (CDR2) having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to one of SEQ ID NOS: SEQ ID NO: 2, or SEQ ID NO: 10, a light chain complementarity determining region 3 (CDR3) having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to one of SEQ ID NO: 3, or SEQ ID NO: 11, a heavy chain complementarity determining region 1 (CDR1) having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to one of SEQ ID NO: 4, or SEQ ID NO: 12, a heavy chain complementarity determining region 2 (CDR2) having an amino acid sequence at least about 75%, 80%, 81%, 82%, 839%, 84%, 85%, 86%, 87%, 88%, 89%, 90%, 91%, 92%, 93%, 94%, 95%, 96%, 97%, 98%, or 99% identical to one of SEQ ID NO: 5, SEQ ID NO: 13, or SEQ ID NO: 18, and a heavy chain complementarity determining region 3 (CDR3) having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to one of SEQ ID NO: 6, or SEQ ID NO: 14. In some embodiments, antibodies binding to MICA/B comprise a light chain complementarity determining region 1 (CDR1) having an amino acid sequence 100% identical to one of SEQ ID NO: 1, SEQ ID NO: 9, or SEQ ID NO: 17, a light chain complementarity determining region 2 (CDR2) having an amino acid sequence 100% identical to one of SEQ ID NOS: SEQ ID NO: 2, or SEQ ID NO: 10, a light chain complementarity determining region 3 (CDR3) having an amino acid sequence 100% identical to one of SEQ ID NO: 3, or SEQ ID NO: 11, a heavy chain complementarity determining region 1 (CDR1) having an amino acid sequence 100% identical to one of SEQ ID NO: 4, or SEQ ID NO: 12, a heavy chain complementarity determining region 2 (CDR2) having an amino acid sequence 100% identical to one of SEQ ID NO: 5, SEQ ID NO: 13, or SEQ ID NO: 18, and a heavy chain complementarity determining region 3 (CDR3) having an amino acid sequence 100% identical to one of SEQ ID NO: 6, or SEQ ID NO: 14.

In some embodiments, antibodies binding to MICA/B comprise at least one of a light chain CDR1 having an amino acid sequence at least about 70% identical to an amino acid sequence set forth as SEQ ID NO: 1, a light chain CDR2 having an amino acid sequence at least about 70% identical to an amino acid sequence set forth as SEQ ID NO: 2, and a light chain CDR3 having an amino acid sequence at least about 70% identical to an amino acid sequence set forth as SEQ ID NO: 3. In some embodiments, antibodies binding to MICA/B comprise at least one of a light chain a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 1, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, and a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3. In some embodiments, antibodies binding to MICA/B comprise at least one of a light chain CDR1 having an amino acid sequence 100% identical to an amino acid sequence set forth as SEQ ID NO: 1, a light chain CDR2 having an amino acid sequence 100% identical to an amino acid sequence set forth as SEQ ID NO: 2, and a light chain CDR3 having an amino acid sequence 100% identical to an amino acid sequence set forth as SEQ ID NO: 3.

In some embodiments, antibodies binding to MICA/B comprise at least one of a light chain CDR1 having an amino acid sequence at least about 70% identical to an amino acid sequence set forth as SEQ ID NO: 9, a light chain CDR2 having an amino acid sequence at least about 70% identical to an amino acid sequence set forth as SEQ ID NO: 10, and a light chain CDR3 having an amino acid sequence at least about 70% identical to an amino acid sequence set forth as SEQ ID NO: 11. In some embodiments, antibodies binding to MICA/B comprise at least one of a light chain a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 9, a light chain CDR2 having an amino acid sequence at least about 75%, 80%, 81%, 82%, 83%, 84%, 85%, 86%, 87%, 88%, 89%, 90%, 919%, 92%, 93%, 94%, 95%, 96%, 97%, 98%, or 99% identical to an amino acid sequence set forth as SEQ ID NO: 10, and a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 11. In some embodiments, antibodies binding to MICA/B comprise at least one of a light chain CDR1 having an amino acid sequence 100% identical to an amino acid sequence set forth as SEQ ID NO: 9, a light chain CDR2 having an amino acid sequence 100% identical to an amino acid sequence set forth as SEQ ID NO: 10, and a light chain CDR3 having an amino acid sequence 100% identical to an amino acid sequence set forth as SEQ ID NO: 11.

In some embodiments, antibodies binding to MICA/B comprise at least one of a light chain CDR1 having an amino acid sequence at least about 70% identical to an amino acid sequence set forth as SEQ ID NO: 17, a light chain CDR2 having an amino acid sequence at least about 70% identical to an amino acid sequence set forth as SEQ ID NO: 2, and a light chain CDR3 having an amino acid sequence at least about 70% identical to an amino acid sequence set forth as SEQ ID NO: 3. In some embodiments, antibodies binding to MICA/B comprise at least one of a light chain a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 17, a light chain CDR2 having an amino acid sequence at least about 75%, 80%, 81%, 82%, 839%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, and a light chain CDR3 having an amino acid sequence at least about 75%, 80%, 81%, 829%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3. In some embodiments, antibodies binding to MICA/B comprise at least one of a light chain CDR1 having an amino acid sequence 100% identical to an amino acid sequence set forth as SEQ ID NO: 17, a light chain CDR2 having an amino acid sequence 100% identical to an amino acid sequence set forth as SEQ ID NO: 2, and a light chain CDR3 having an amino acid sequence 100% identical to an amino acid sequence set forth as SEQ ID NO: 3.

In some embodiments, antibodies binding to MICA/B comprise at least one of a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 5, a heavy chain CDR3 having an amino acid sequence at least about 70% identical to an amino acid sequence set forth as SEQ ID NO: 6. In some embodiments, antibodies binding to MICA/B comprise at least one of a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 5, a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, antibodies binding to MICA/B comprise at least one of a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 5, a heavy chain CDR3 having an amino acid sequence 100% identical to an amino acid sequence set forth as SEQ ID NO: 6.

In some embodiments, antibodies binding to MICA/B comprise at least one of a heavy chain CDR1 having an amino acid sequence at least about 70% identical to an amino acid sequence set forth as SEQ ID NO: 12, a heavy chain CDR2 having an amino acid sequence at least about 70% identical to an amino acid sequence set forth as SEQ ID NO: 13, a heavy chain CDR3 having an amino acid sequence at least about 70% identical to an amino acid sequence set forth as SEQ ID NO: 14. In some embodiments, antibodies binding to MICA/B comprise at least one of a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 12, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 13, a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 14. In some embodiments, antibodies binding to MICA/B comprise at least one of a heavy chain CDR1 having an amino acid sequence 100% identical to an amino acid sequence set forth as SEQ ID NO: 12, a heavy chain CDR2 having an amino acid sequence 100% identical to an amino acid sequence set forth as SEQ ID NO: 13, a heavy chain CDR3 having an amino acid sequence 100% identical to an amino acid sequence set forth as SEQ ID NO: 14.

In some embodiments, antibodies binding to MICA/B comprise at least one of a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 18, a heavy chain CDR3 having an amino acid sequence at least about 70% identical to an amino acid sequence set forth as SEQ ID NO: 6. In some embodiments, antibodies binding to MICA/B comprise at least one of a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 18, a heavy chain CDR3 having an amino acid sequence at least about 75%, 80%, 81%, 82%, 83%, 84%, 85%, 86%, 87%, 88%, 89%, 909%, 91%, 92%, 93%, 94%, 95%, 96%, 97%, 98%, or 99% identical to an amino acid sequence set forth as SEQ ID NO: 6. In some embodiments, antibodies binding to MICA/B comprise at least one of a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 18, a heavy chain CDR3 having an amino acid sequence 100% identical to an amino acid sequence set forth as SEQ ID NO: 6.

In some embodiments, antibodies binding to MICA/B comprise at least one of a light chain CDR1 having an amino acid sequence at least about 70% identical to an amino acid sequence set forth as SEQ ID NO: 1, a light chain CDR2 having an amino acid sequence at least about 70% identical to an amino acid sequence set forth as SEQ ID NO: 2, a light chain CDR3 having an amino acid sequence at least about 70% identical to an amino acid sequence set forth as SEQ ID NO: 3, a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 5, and a heavy chain CDR3 having an amino acid sequence at least about 70% identical to an amino acid sequence set forth as SEQ ID NO: 6. In some embodiments, antibodies binding to MICA/B comprise at least one of a light chain CDR1 having an amino acid sequence at least about 75%, 80%, 81%, 82%, 83%, 84%, 85%, 86%, 87%, 88%, 89%, 90%, 919%, 92%, 93%, 94%, 95%, 96%, 97%, 98%, or 99% identical to an amino acid sequence set forth as SEQ ID NO: 1, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3, a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 5, and a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, antibodies binding to MICA/B comprise at least one of a light chain CDR1 having an amino acid sequence 100% identical to an amino acid sequence set forth as SEQ ID NO: 1, a light chain CDR2 having an amino acid sequence 100% identical to an amino acid sequence set forth as SEQ ID NO: 2, a light chain CDR3 having an amino acid sequence 100% identical to an amino acid sequence set forth as SEQ ID NO: 3, a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 5, and a heavy chain CDR3 having an amino acid sequence 100% identical to an amino acid sequence set forth as SEQ ID NO: 6.

In some embodiments, antibodies binding to MICA/B comprise at least one of a light chain CDR1 having an amino acid sequence at least about 70% identical to an amino acid sequence set forth as SEQ ID NO: 9, a light chain CDR2 having an amino acid sequence at least about 70% identical to an amino acid sequence set forth as SEQ ID NO: 10, a light chain CDR3 having an amino acid sequence at least about 70% identical to an amino acid sequence set forth as SEQ ID NO: 11, a heavy chain CDR1 having an amino acid sequence at least about 70% identical to an amino acid sequence set forth as SEQ ID NO: 12, a heavy chain CDR2 having an amino acid sequence at least about 70% identical to an amino acid sequence set forth as SEQ ID NO: 13, and a heavy chain CDR3 having an amino acid sequence at least about 70% identical to an amino acid sequence set forth as SEQ ID NO: 14. In some embodiments, antibodies binding to MICA/B comprise at least one of a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 9, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 10, a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 11, a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 12, a heavy chain CDR2 having an amino acid sequence at least about. 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 13, and a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 14. In some embodiments, antibodies binding to MICA/B comprise at least one of a light chain CDR1 having an amino acid sequence 100% identical to an amino acid sequence set forth as SEQ ID NO: 9, a light chain CDR2 having an amino acid sequence 100% identical to an amino acid sequence set forth as SEQ ID NO: 10, a light chain CDR3 having an amino acid sequence 100% identical to an amino acid sequence set forth as SEQ ID NO: 11, a heavy chain CDR1 having an amino acid sequence 100% identical to an amino acid sequence set forth as SEQ ID NO: 12, a heavy chain CDR2 having an amino acid sequence 100% identical to an amino acid sequence set forth as SEQ ID NO: 13, and a heavy chain CDR3 having an amino acid sequence 100% identical to an amino acid sequence set forth as SEQ ID NO: 14.

In some embodiments, antibodies binding to MICA/B comprise at least one of a light chain CDR1 having an amino acid sequence at least about 70% identical to an amino acid sequence set forth as SEQ ID NO: 17, a light chain CDR2 having an amino acid sequence at least about 70% identical to an amino acid sequence set forth as SEQ ID NO: 2, a light chain CDR3 having an amino acid sequence at least about 70% identical to an amino acid sequence set forth as SEQ ID NO: 3, a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 18, and a heavy chain CDR3 having an amino acid sequence at least about 70% identical to an amino acid sequence set forth as SEQ ID NO: 6. In some embodiments, antibodies binding to MICA/B comprise at least one of a light chain CDR1 having an amino acid sequence at least about 75%, 80%, 81%, 82%, 839%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 17, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3, a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 919%, 92%, 93%, 94%, 95%, 96%, 97%, 98%, or 99% identical to an amino acid sequence set forth as SEQ ID NO: 18, and a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, antibodies binding to MICA/B comprise at least one of a light chain CDR1 having an amino acid sequence 100% identical to an amino acid sequence set forth as SEQ ID NO: 17, a light chain CDR2 having an amino acid sequence 100% identical to an amino acid sequence set forth as SEQ ID NO: 2, a light chain CDR3 having an amino acid sequence 100% identical to an amino acid sequence set forth as SEQ ID NO: 3, a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 18, and a heavy chain CDR3 having an amino acid sequence 100% identical to an amino acid sequence set forth as SEQ ID NO: 6.

In some embodiments, antibodies binding to MICA/B do not have at least one CDR selected from the list comprising: SASQGISNYLN, TSLLHSG, QQYSKFPRT, GYTFTNYGMN, INTYTGEPTYADDFKG, and NYG-NYLEDY.

Competitive Binding

Disclosed herein, in some embodiments, are antibodies that competitively bind to MICA/B with an antibody comprising a light chain variable domain (VL) having an amino acid sequence at least about 70% identical to an amino acid sequence set forth as SEQ ID NO: 27. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 27. In some embodiments, the VL has an amino acid sequence 100% identical to an amino acid sequence set forth as SEQ ID NO: 27.

Disclosed herein, in some embodiments, are antibodies that competitively bind to MICA/B with an antibody comprising a heavy chain variable domain (VH) having an amino acid sequence at least about 70% identical to an amino acid sequence set forth as SEQ ID NO: 28. In some embodiments the VH has an amino acid sequence at least about 75%, 80%, 81%, 82%, 83%, 84%, 85%, 86%, 87%, 88%, 89%, 90%, 919%, 92%, 93%, 94%, 95%, 96%, 97%, 98%, or 99% identical to an amino acid sequence set forth as SEQ ID NO: 28. In some embodiments, the VH has an amino acid sequence 100% identical to an amino acid sequence set forth as SEQ ID NO: 28.

Disclosed herein, in some embodiments, are antibodies that competitively bind to MICA/B with an antibody comprising a light chain variable domain (VL) having an amino acid sequence at least about 70% identical to an amino acid sequence set forth as SEQ ID NO: 27 and a heavy chain variable domain (VH) having an amino acid sequence at least about 70% identical to an amino acid sequence set forth as SEQ ID NO: 28. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 27 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 28. In some embodiments, the VL has an amino acid sequence 100% identical to an amino acid sequence set forth as SEQ ID NO: 27 and the VH has an amino acid sequence 100% identical to an amino acid sequence set forth as SEQ ID NO: 28.

Methods of Treatment and Use

Provided herein are methods of treating cancer (e.g. hepatocellular carcinoma) in an individual in need thereof comprising administration of an anti-MICA/B antibody disclosed herein.

Further provided herein are methods of reducing level of soluble MICA/B proteins in an individual in need thereof comprising administration of an anti-MICA/B antibody disclosed herein.

Also provided herein are methods of alleviating or inhibiting the immunosuppressive environment by preventing or blocking the interaction between soluble MICA/B and NKG2D receptors in an individual in need thereof comprising administration of an anti-MICA/B antibody disclosed herein.

In some embodiments, antibodies binding to MICA/B comprise a light chain CDR sequence having an amino acid sequence at least about 70% identical to at least one of the amino acid sequences set forth as SEQ ID NOS: 1-3, 9-11, and 17. In some embodiments, antibodies binding to MICA/B comprise a light chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 1-3, 9-11, and 17. In some embodiments, antibodies binding to MICA/B comprise a light chain CDR sequence having an amino acid sequence 100% identical to at least one of the amino acid sequences set forth as SEQ ID NOS: 1-3, 9-11, and 17.

In some embodiments, antibodies binding to MICA/B comprise a heavy chain CDR sequence having an amino acid sequence at least about 70% identical to at least one of the amino acid sequences set forth as SEQ ID NOS: 4-6, 12-14, and 18. In some embodiments, antibodies binding to MICA/B comprise a heavy chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 4-6, 12-14, and 18. In some embodiments, antibodies binding to MICA/B comprise a heavy chain CDR sequence having an amino acid sequence 100% identical to at least one of the amino acid sequences set forth as SEQ ID NOS: 4-6, 12-14, and 18.

In some embodiments, antibodies binding to MICA/B comprise a light chain CDR sequence having an amino acid sequence at least about 70% identical to at least one of the amino acid sequences set forth as SEQ ID NOS: 1-3, 9-11, and 17 and a heavy chain CDR sequence having an amino acid sequence at least about 70% identical to at least one of the amino acid sequences set forth as SEQ ID NOS: 4-6, 12-14, and 18. In some embodiments, antibodies binding to MICA/B comprise a light chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 1-3, 9-11, and 17 and a heavy chain CDR sequence having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to at least one of the amino acid sequences set forth as SEQ ID NOS: 4-6, 12-14, and 18. In some embodiments, antibodies binding to MICA/B comprise a light chain CDR sequence having an amino acid sequence 100% identical to at least one of the amino acid sequences set forth as SEQ ID NOS: 1-3, 9-11, and 17 and a heavy chain CDR sequence having an amino acid sequence at least about 100% identical to at least one of the amino acid sequences set forth as SEQ ID NOS: 4-6, 12-14, and 18.

In some embodiments, antibodies binding to MICA/B comprise a light chain complementarity determining region 1 (CDR1) having an amino acid sequence at least about 70% identical to one of SEQ ID NO: 1. SEQ ID NO: 9, or SEQ ID NO: 17, a light chain complementarity determining region 2 (CDR2) having an amino acid sequence at least about 70% identical to one of SEQ ID NOS: SEQ ID NO: 2, or SEQ ID NO: 10, a light chain complementarity determining region 3 (CDR3) having an amino acid sequence at least about 70% identical to one of SEQ ID NO: 3, or SEQ ID NO: 11, a heavy chain complementarity determining region 1 (CDR1) having an amino acid sequence at least about 70% identical to one of SEQ ID NO: 4, or SEQ ID NO: 12, a heavy chain complementarity determining region 2 (CDR2) having an amino acid sequence at least about 70% identical to one of SEQ ID NO: 5. SEQ ID NO: 13, or SEQ ID NO: 18, and a heavy chain complementarity determining region 3 (CDR3) having an amino acid sequence at least about 70% identical to one of SEQ ID NO: 6, or SEQ ID NO: 14. In some embodiments, antibodies binding to MICA/B comprise a light chain complementarity determining region 1 (CDR1) having an amino acid sequence at least about 75%, 80%, 81%, 82%, 83%, 84%, 85%, 86%, 87%, 88%, 89%, 90%, 91%, 929%, 93%, 94%, 95%, 96%, 97%, 98%, or 99% identical to one of SEQ ID NO: 1, SEQ ID NO: 9, or SEQ ID NO: 17, a light chain complementarity determining region 2 (CDR2) having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to one of SEQ ID NOS: SEQ ID NO: 2, or SEQ ID NO: 10, a light chain complementarity determining region 3 (CDR3) having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to one of SEQ ID NO: 3, or SEQ ID NO: 11, a heavy chain complementarity determining region 1 (CDR1) having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to one of SEQ ID NO: 4, or SEQ ID NO: 12, a heavy chain complementarity determining region 2 (CDR2) having an amino acid sequence at least about 75%, 80%, 81%, 82%, 839%, 84%, 85%, 86%, 87%, 88%, 89%, 90%, 91%, 92%, 93%, 94%, 95%, 96%, 97%, 98%, or 99% identical to one of SEQ ID NO: 5, SEQ ID NO: 13, or SEQ ID NO: 18, and a heavy chain complementarity determining region 3 (CDR3) having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to one of SEQ ID NO: 6, or SEQ ID NO: 14. In some embodiments, antibodies binding to MICA/B comprise a light chain complementarity determining region 1 (CDR1) having an amino acid sequence 100% identical to one of SEQ ID NO: 1. SEQ ID NO: 9, or SEQ ID NO: 17, a light chain complementarity determining region 2 (CDR2) having an amino acid sequence 100% identical to one of SEQ ID NOS: SEQ ID NO: 2, or SEQ ID NO: 10, a light chain complementarity determining region 3 (CDR3) having an amino acid sequence 100% identical to one of SEQ ID NO: 3, or SEQ ID NO: 11, a heavy chain complementarity determining region 1 (CDR1) having an amino acid sequence 100% identical to one of SEQ ID NO: 4, or SEQ ID NO: 12, a heavy chain complementarity determining region 2 (CDR2) having an amino acid sequence 100% identical to one of SEQ ID NO: 5, SEQ ID NO: 13, or SEQ ID NO: 18, and a heavy chain complementarity determining region 3 (CDR3) having an amino acid sequence 100% identical to one of SEQ ID NO: 6, or SEQ ID NO: 14.

In some embodiments, antibodies binding to MICA/B comprise at least one of a light chain CDR1 having an amino acid sequence at least about 70% identical to an amino acid sequence set forth as SEQ ID NO: 1, a light chain CDR2 having an amino acid sequence at least about 70% identical to an amino acid sequence set forth as SEQ ID NO: 2, and a light chain CDR3 having an amino acid sequence at least about 70% identical to an amino acid sequence set forth as SEQ ID NO: 3. In some embodiments, antibodies binding to MICA/B comprise at least one of a light chain a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 1, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, and a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3. In some embodiments, antibodies binding to MICA/B comprise at least one of a light chain CDR1 having an amino acid sequence 100% identical to an amino acid sequence set forth as SEQ ID NO: 1, a light chain CDR2 having an amino acid sequence 100% identical to an amino acid sequence set forth as SEQ ID NO: 2, and a light chain CDR3 having an amino acid sequence 100% identical to an amino acid sequence set forth as SEQ ID NO: 3.

In some embodiments, antibodies binding to MICA/B comprise at least one of a light chain CDR1 having an amino acid sequence at least about 70% identical to an amino acid sequence set forth as SEQ ID NO: 9, a light chain CDR2 having an amino acid sequence at least about 70% identical to an amino acid sequence set forth as SEQ ID NO: 10, and a light chain CDR3 having an amino acid sequence at least about 70% identical to an amino acid sequence set forth as SEQ ID NO: 11. In some embodiments, antibodies binding to MICA/B comprise at least one of a light chain a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 9, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 10, and a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 11. In some embodiments, antibodies binding to MICA/B comprise at least one of a light chain CDR1 having an amino acid sequence 100% identical to an amino acid sequence set forth as SEQ ID NO: 9, a light chain CDR2 having an amino acid sequence 100% identical to an amino acid sequence set forth as SEQ ID NO: 10, and a light chain CDR3 having an amino acid sequence 100% identical to an amino acid sequence set forth as SEQ ID NO: 11.

In some embodiments, antibodies binding to MICA/B comprise at least one of a light chain CDR1 having an amino acid sequence at least about 70% identical to an amino acid sequence set forth as SEQ ID NO: 17, a light chain CDR2 having an amino acid sequence at least about 70% identical to an amino acid sequence set forth as SEQ ID NO: 2, and a light chain CDR3 having an amino acid sequence at least about 70% identical to an amino acid sequence set forth as SEQ ID NO: 3. In some embodiments, antibodies binding to MICA/B comprise at least one of a light chain a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 17, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, and a light chain CDR3 having an amino acid sequence at least about 75%, 80%, 81%, 82%, 83%, 84%, 85%, 86%, 87%, 88%, 89%, 90%, 91%, 92%, 93%, 94%, 95% 96%, 97%, 98%, or 99% identical to an amino acid sequence set forth as SEQ ID NO: 3. In some embodiments, antibodies binding to MICA/B comprise at least one of a light chain CDR1 having an amino acid sequence 100% identical to an amino acid sequence set forth as SEQ ID NO: 17, a light chain CDR2 having an amino acid sequence 100% identical to an amino acid sequence set forth as SEQ ID NO: 2, and a light chain CDR3 having an amino acid sequence 100% identical to an amino acid sequence set forth as SEQ ID NO: 3.

In some embodiments, antibodies binding to MICA/B comprise at least one of a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 5, a heavy chain CDR3 having an amino acid sequence at least about 70% identical to an amino acid sequence set forth as SEQ ID NO: 6. In some embodiments, antibodies binding to MICA/B comprise at least one of a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 999% identical to an amino acid sequence set forth as SEQ ID NO: 5, a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, antibodies binding to MICA/B comprise at least one of a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 5, a heavy chain CDR3 having an amino acid sequence 100% identical to an amino acid sequence set forth as SEQ ID NO: 6.

In some embodiments, antibodies binding to MICA/B comprise at least one of a heavy chain CDR1 having an amino acid sequence at least about 70% identical to an amino acid sequence set forth as SEQ ID NO: 12, a heavy chain CDR2 having an amino acid sequence at least about 70% identical to an amino acid sequence set forth as SEQ ID NO: 13, a heavy chain CDR3 having an amino acid sequence at least about 70% identical to an amino acid sequence set forth as SEQ ID NO: 14. In some embodiments, antibodies binding to MICA/B comprise at least one of a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 12, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 13, a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 14. In some embodiments, antibodies binding to MICA/B comprise at least one of a heavy chain CDR1 having an amino acid sequence 100% identical to an amino acid sequence set forth as SEQ ID NO: 12, a heavy chain CDR2 having an amino acid sequence 100% identical to an amino acid sequence set forth as SEQ ID NO: 13, a heavy chain CDR3 having an amino acid sequence 100% identical to an amino acid sequence set forth as SEQ ID NO: 14.

In some embodiments, antibodies binding to MICA/B comprise at least one of a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 18, a heavy chain CDR3 having an amino acid sequence at least about 70% identical to an amino acid sequence set forth as SEQ ID NO: 6. In some embodiments, antibodies binding to MICA/B comprise at least one of a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 18, a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, antibodies binding to MICA/B comprise at least one of a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 18, a heavy chain CDR3 having an amino acid sequence 100% identical to an amino acid sequence set forth as SEQ ID NO: 6.

In some embodiments, antibodies binding to MICA/B comprise at least one of a light chain CDR1 having an amino acid sequence at least about 70% identical to an amino acid sequence set forth as SEQ ID NO: 1, a light chain CDR2 having an amino acid sequence at least about 70% identical to an amino acid sequence set forth as SEQ ID NO: 2, a light chain CDR3 having an amino acid sequence at least about 70% identical to an amino acid sequence set forth as SEQ ID NO: 3, a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 5, and a heavy chain CDR3 having an amino acid sequence at least about 70% identical to an amino acid sequence set forth as SEQ ID NO: 6. In some embodiments, antibodies binding to MICA/B comprise at least one of a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 1, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3, a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 5, and a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, antibodies binding to MICA/B comprise at least one of a light chain CDR1 having an amino acid sequence 100% identical to an amino acid sequence set forth as SEQ ID NO: 1, a light chain CDR2 having an amino acid sequence 100% identical to an amino acid sequence set forth as SEQ ID NO: 2, a light chain CDR3 having an amino acid sequence 100% identical to an amino acid sequence set forth as SEQ ID NO: 3, a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 5, and a heavy chain CDR3 having an amino acid sequence 100% identical to an amino acid sequence set forth as SEQ ID NO: 6.

In some embodiments, antibodies binding to MICA/B comprise at least one of a light chain CDR1 having an amino acid sequence at least about 70% identical to an amino acid sequence set forth as SEQ ID NO: 9, a light chain CDR2 having an amino acid sequence at least about 70% identical to an amino acid sequence set forth as SEQ ID NO: 10, a light chain CDR3 having an amino acid sequence at least about 70% identical to an amino acid sequence set forth as SEQ ID NO: 11, a heavy chain CDR1 having an amino acid sequence at least about 70% identical to an amino acid sequence set forth as SEQ ID NO: 12, a heavy chain CDR2 having an amino acid sequence at least about 70% identical to an amino acid sequence set forth as SEQ ID NO: 13, and a heavy chain CDR3 having an amino acid sequence at least about 70% identical to an amino acid sequence set forth as SEQ ID NO: 14. In some embodiments, antibodies binding to MICA/B comprise at least one of a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 9, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 10, a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 11, a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 12, a heavy chain CDR2 having an amino acid sequence at least about 75%, 80%, 81%, 82%, 83%, 84%, 85%, 86%, 87%, 88%, 89%, 90%, 919%: 92%, 93%, 94%, 95%, 96%, 97%, 98%, or 99% identical to an amino acid sequence set forth as SEQ ID NO: 13, and a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 14. In some embodiments, antibodies binding to MICA/B comprise at least one of a light chain CDR1 having an amino acid sequence 100% identical to an amino acid sequence set forth as SEQ ID NO: 9, a light chain CDR2 having an amino acid sequence 100% identical to an amino acid sequence set forth as SEQ ID NO: 10, a light chain CDR3 having an amino acid sequence 100% identical to an amino acid sequence set forth as SEQ ID NO: 11, a heavy chain CDR1 having an amino acid sequence 100% identical to an amino acid sequence set forth as SEQ ID NO: 12, a heavy chain CDR2 having an amino acid sequence 100% identical to an amino acid sequence set forth as SEQ ID NO: 13, and a heavy chain CDR3 having an amino acid sequence 100% identical to an amino acid sequence set forth as SEQ ID NO: 14.

In some embodiments, antibodies binding to MICA/B comprise at least one of a light chain CDR1 having an amino acid sequence at least about 70% identical to an amino acid sequence set forth as SEQ ID NO: 17, a light chain CDR2 having an amino acid sequence at least about 70% identical to an amino acid sequence set forth as SEQ ID NO: 2, a light chain CDR3 having an amino acid sequence at least about 70% identical to an amino acid sequence set forth as SEQ ID NO: 3, a heavy chain CDR1 having an amino acid sequence at least about 70% identical to an amino acid sequence set forth as SEQ ID NO: 4, a heavy chain CDR2 having an amino acid sequence at least about 70% identical to an amino acid sequence set forth as SEQ ID NO: 18, and a heavy chain CDR3 having an amino acid sequence at least about 70% identical to an amino acid sequence set forth as SEQ ID NO: 6. In some embodiments, antibodies binding to MICA/B comprise at least one of a light chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 17, a light chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 2, a light chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 3, a heavy chain CDR1 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 4, a heavy chain CDR2 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 18, and a heavy chain CDR3 having an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 6. In some embodiments, antibodies binding to MICA/B comprise at least one of a light chain CDR1 having an amino acid sequence 100% identical to an amino acid sequence set forth as SEQ ID NO: 17, a light chain CDR2 having an amino acid sequence 100% identical to an amino acid sequence set forth as SEQ ID NO: 2, a light chain CDR3 having an amino acid sequence 100% identical to an amino acid sequence set forth as SEQ ID NO: 3, a heavy chain CDR1 having an amino acid sequence 100% identical to an amino acid sequence set forth as SEQ ID NO: 4, a heavy chain CDR2 having an amino acid sequence 100% identical to an amino acid sequence set forth as SEQ ID NO: 18, and a heavy chain CDR3 having an amino acid sequence 100% identical to an amino acid sequence set forth as SEQ ID NO: 6.

In some embodiments, antibodies binding to MICA/B do not have at least one CDR selected from the list comprising: SASQGISNYLN, TSLLHSG, QQYSKFPRT, GYTFTNYGMN, INTYTGEPTYADDFKG, and NYG-NYLEDY.

In some embodiments, antibodies binding to MICA/B comprise a light chain variable domain (VL) having an amino acid sequence at least about 70% identical to an amino acid sequence set forth as SEQ ID NO: 7, SEQ ID NO: 15, or SEQ ID NO: 19. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7. SEQ ID NO: 15, or SEQ ID NO: 19. In some embodiments, the VL has an amino acid sequence 100% identical to an amino acid sequence set forth as SEQ ID NO: 7. SEQ ID NO: 15, or SEQ ID NO: 19.

In some embodiments, antibodies binding to MICA/B comprise a heavy chain variable domain (VH) having an amino acid sequence at least about 70% identical to an amino acid sequence set forth as SEQ ID NO: 8. SEQ ID NO: 16, or SEQ ID NO: 20. In some embodiments the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8, SEQ ID NO: 16, or SEQ ID NO: 20. In some embodiments, the VH has an amino acid sequence 100% identical to an amino acid sequence set forth as SEQ ID NO: 8, SEQ ID NO: 16, or SEQ ID NO: 20.

In some embodiments, antibodies binding to MICA/B comprise a light chain variable domain (VL) having an amino acid sequence at least about 70% identical to an amino acid sequence set forth as SEQ ID NO: 7, SEQ ID NO: 15, or SEQ ID NO: 19 and a heavy chain variable domain (VH) having an amino acid sequence at least about 70% identical to an amino acid sequence set forth as SEQ ID NO: 8. SEQ ID NO: 16, or SEQ ID NO: 20. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7, SEQ ID NO: 15, or SEQ ID NO: 19 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8, SEQ ID NO: 16, or SEQ ID NO: 20. In some embodiments, the VL has an amino acid sequence 100% identical to an amino acid sequence set forth as SEQ ID NO: 7, SEQ ID NO: 15, or SEQ ID NO: 19 and the VH has an amino acid sequence 100% identical to an amino acid sequence set forth as SEQ ID NO: 8, SEQ ID NO: 16, or SEQ ID NO: 20.

In some embodiments, antibodies binding to MICA/B comprise a light chain variable domain (VL) having an amino acid sequence at least about 70% identical to an amino acid sequence set forth as SEQ ID NO: 7 and a heavy chain variable domain (VH) having an amino acid sequence at least about 70% identical to an amino acid sequence set forth as SEQ ID NO: 8. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 7 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 8. In some embodiments, the VL has an amino acid sequence 100% identical to an amino acid sequence set forth as SEQ ID NO: 7 and the VH has an amino acid sequence 100% identical to an amino acid sequence set forth as SEQ ID NO: 8.

In some embodiments, antibodies binding to MICA/B comprise a light chain variable domain (VL) having an amino acid sequence at least about 70% identical to an amino acid sequence set forth as SEQ ID NO: 15 and a heavy chain variable domain (VH) having an amino acid sequence at least about 70% identical to an amino acid sequence set forth as SEQ ID NO: 16. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 15 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 16. In some embodiments, the VL has an amino acid sequence 100% identical to an amino acid sequence set forth as SEQ ID NO: 15 and the VH has an amino acid sequence 100% identical to an amino acid sequence set forth as SEQ ID NO: 16.

In some embodiments, antibodies binding to MICA/B comprise a light chain variable domain (VL) having an amino acid sequence at least about 70% identical to an amino acid sequence set forth as SEQ ID NO: 19 and a heavy chain variable domain (VH) having an amino acid sequence at least about 70% identical to an amino acid sequence set forth as SEQ ID NO: 20. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 19 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 20. In some embodiments, the VL has an amino acid sequence 100% identical to an amino acid sequence set forth as SEQ ID NO: 19 and the VH has an amino acid sequence 100% identical to an amino acid sequence set forth as SEQ ID NO: 20.

In some embodiments, antibodies binding to MICA/B comprise a light chain having an amino acid sequence at least about 70% identical to an amino acid sequence set forth as SEQ ID NO: 21, SEQ ID NO: 23, or SEQ ID NO: 24. In some embodiments the light chain has an amino acid sequence at least about 75%, 80%, 81%, 829%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 21, SEQ ID NO: 23, or SEQ ID NO: 24. In some embodiments, the light chain has an amino acid sequence 100% identical to an amino acid sequence set forth as SEQ ID NO: 21, SEQ ID NO: 23, or SEQ ID NO: 24.

In some embodiments, antibodies binding to MICA/B comprise a heavy chain having an amino acid sequence at least about 70% identical to an amino acid sequence set forth as SEQ ID NO: 22, SEQ ID NO: 25, or SEQ ID NO: 26. In some embodiments the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 22, SEQ ID NO: 25, or SEQ ID NO: 26. In some embodiments, the heavy chain has an amino acid sequence 100% identical to an amino acid sequence set forth as SEQ ID NO: 22, SEQ ID NO: 25, or SEQ ID NO: 26.

Also disclosed herein are antibodies binding to MICA/B comprising a light chain and a heavy chain. In some embodiments, antibodies binding to MICA/B comprise a light chain having an amino acid sequence at least about 70% identical to an amino acid sequence set forth as SEQ ID NO: 21, SEQ ID NO: 23, or SEQ ID NO: 24 and a heavy chain having an amino acid sequence at least about 70% identical to an amino acid sequence set forth as SEQ ID NO: 22, SEQ ID NO: 25, or SEQ ID NO: 26. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 21. SEQ ID NO: 23, or SEQ ID NO: 24 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 22, SEQ ID NO: 25, or SEQ ID NO: 26. In some embodiments, the light chain has an amino acid sequence 100% identical to an amino acid sequence set forth as SEQ ID NO: 21, SEQ ID NO: 23, or SEQ ID NO: 24 and the heavy chain has an amino acid sequence 100% identical to an amino acid sequence set forth as SEQ ID NO: 22. SEQ ID NO: 25, or SEQ ID NO: 26.

In some embodiments, antibodies binding to MICA/B comprise a light chain having an amino acid sequence at least about 70% identical to an amino acid sequence set forth as SEQ ID NO: 21 and a heavy chain having an amino acid sequence at least about 70% identical to an amino acid sequence set forth as SEQ ID NO: 22. In some embodiments the light chain has an amino acid sequence at least about 75%, 80%, 81%, 82%, 83%, 84%, 85%, 86%, 879%, 88%, 89%, 90%, 91%, 92%, 93%, 94%, 95%, 96%, 97%, 98%, or 99% identical to an amino acid sequence set forth as SEQ ID NO: 21 and the heavy chain has an amino acid sequence at least about 75%, 80%, 81%, 82%, 83%, 849%, 85%, 86%, 87%, 88%, 89%, 90%, 91%, 92%, 93%, 94%, 95%, 96%, 97%, 98%, or 99% identical to an amino acid sequence set forth as SEQ ID NO: 22. In some embodiments, the light chain has an amino acid sequence 100% identical to an amino acid sequence set forth as SEQ ID NO: 21 and the heavy chain has an amino acid sequence 100% identical to an amino acid sequence set forth as SEQ ID NO: 22.

In some embodiments, antibodies binding to MICA/B comprise a light chain having an amino acid sequence at least about 70% identical to an amino acid sequence set forth as SEQ ID NO: 23 and a heavy chain having an amino acid sequence at least about 70% identical to an amino acid sequence set forth as SEQ ID NO: 25. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 23 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 25. In some embodiments, the light chain has an amino acid sequence 100% identical to an amino acid sequence set forth as SEQ ID NO: 23 and the heavy chain has an amino acid sequence 100% identical to an amino acid sequence set forth as SEQ ID NO: 25.

In some embodiments, antibodies binding to MICA/B comprise a light chain having an amino acid sequence at least about 70% identical to an amino acid sequence set forth as SEQ ID NO: 23 and a heavy chain having an amino acid sequence at least about 70% identical to an amino acid sequence set forth as SEQ ID NO: 26. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 23 and the heavy chain has an amino acid sequence at least about 75%, 80%, 81%, 82%, 83%, 849%, 85%, 86%, 87%, 88%, 89%, 90%, 91%, 92%, 93%, 94%, 95%, 96%, 97%, 98%, or 99% identical to an amino acid sequence set forth as SEQ ID NO: 26. In some embodiments, the light chain has an amino acid sequence 100% identical to an amino acid sequence set forth as SEQ ID NO: 23 and the heavy chain has an amino acid sequence 100% identical to an amino acid sequence set forth as SEQ ID NO: 26.

In some embodiments, antibodies binding to MICA/B comprise a light chain having an amino acid sequence at least about 70% identical to an amino acid sequence set forth as SEQ ID NO: 24 and a heavy chain having an amino acid sequence at least about 70% identical to an amino acid sequence set forth as SEQ ID NO: 25. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 24 and the heavy chain has an amino acid sequence at least about 75%, 80%, 81%, 82%, 83%, 849%, 85%, 86%, 87%, 88%, 89%, 90%, 91%, 92%, 93%, 94%, 95%, 96%, 97%, 98%, or 99% identical to an amino acid sequence set forth as SEQ ID NO: 25. In some embodiments, the light chain has an amino acid sequence 100% identical to an amino acid sequence set forth as SEQ ID NO: 24 and the heavy chain has an amino acid sequence 100% identical to an amino acid sequence set forth as SEQ ID NO: 25.

In some embodiments, antibodies binding to MICA/B comprise a light chain having an amino acid sequence at least about 70% identical to an amino acid sequence set forth as SEQ ID NO: 24 and a heavy chain having an amino acid sequence at least about 70% identical to an amino acid sequence set forth as SEQ ID NO: 26. In some embodiments the light chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 24 and the heavy chain has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 26. In some embodiments, the light chain has an amino acid sequence 100% identical to an amino acid sequence set forth as SEQ ID NO: 24 and the heavy chain has an amino acid sequence 100% identical to an amino acid sequence set forth as SEQ ID NO: 26.

In some embodiments, antibodies competitively bind to MICA/B with an antibody comprising a light chain variable domain (VL) having an amino acid sequence at least about 70% identical to an amino acid sequence set forth as SEQ ID NO: 27. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 27. In some embodiments, the VL has an amino acid sequence 100% identical to an amino acid sequence set forth as SEQ ID NO: 27.

In some embodiments, antibodies competitively bind to MICA/B with an antibody comprising a heavy chain variable domain (VH) having an amino acid sequence at least about 70% identical to an amino acid sequence set forth as SEQ ID NO: 28. In some embodiments the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 28. In some embodiments, the VH has an amino acid sequence 100% identical to an amino acid sequence set forth as SEQ ID NO: 28.

In some embodiments, antibodies competitively bind to MICA/B with an antibody comprising a light chain variable domain (VL) having an amino acid sequence at least about 70% identical to an amino acid sequence set forth as SEQ ID NO: 27 and a heavy chain variable domain (VH) having an amino acid sequence at least about 70% identical to an amino acid sequence set forth as SEQ ID NO: 28. In some embodiments the VL has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 27 and the VH has an amino acid sequence at least about 75%, 80%, 81%, 82%, 83%, 84%, 85%, 86%, 87%, 88%, 89%, 90%, 91%, 92%, 93%, 94%, 95%, 96%, 97%, 98%, or 99% identical to an amino acid sequence set forth as SEQ ID NO: 28. In some embodiments, the VL has an amino acid sequence 100% identical to an amino acid sequence set forth as SEQ ID NO: 27 and the VH has an amino acid sequence 100% identical to an amino acid sequence set forth as SEQ ID NO: 28.

In some embodiments, the antibodies specifically bind to a MICA protein. In some embodiments, the antibodies specifically bind to a MICB protein. In some embodiments, the antibodies specifically bind to both MICA and MICB protein. In some embodiments, the antibodies bind to an alpha-3 domain of a MICA protein. In some embodiments, the antibodies bind to an alpha-3 domain of a MICB protein. In some embodiments, the antibodies bind to an alpha-3 domain of both MICA and MICB protein. In some embodiments, the antibodies bind to a MICA protein that is membrane-bound MICA protein. In some embodiments, the antibodies bind to a MICA protein that is soluble MICA protein. In some embodiments, the antibodies bind to a MICA protein that is both membrane-bound MICA protein and soluble MICA protein. In some embodiments, the antibodies bind to a MICB protein that is membrane-bound MICB protein. In some embodiments, the antibodies bind to a MICB protein that is soluble MICB protein. In some embodiments, the antibodies bind to a MICB protein that is both membrane-bound MICB protein and soluble MICB protein.

In some embodiments, antibodies that specifically bind to MICA/B are monoclonal antibodies. In some embodiments, the antibody is an antigen binding fragment. In some embodiments, the antibody is selected from a whole immunoglobulin, an scFv, a Fab, a F(ab')2, or a disulfide linked Fv. In some embodiments, the antibody is an IgG or an IgM. In some embodiments, the antibody is humanized. In some embodiments, the antibody is chimeric.

In some embodiments, the antibodies disclosed herein reduce level of soluble MICA protein. In some embodiments, the antibodies disclosed herein reduce level of soluble MICB protein. In some embodiments, the antibodies disclosed herein reduce level of both soluble MICA protein and soluble MICB protein. In some embodiments, the antibodies disclosed herein reduce shedding of soluble MICA protein. In some embodiments, the antibodies disclosed herein reduce shedding of soluble MICB protein. In some embodiments, the antibodies disclosed herein reduce shedding of both soluble MICA protein and soluble MICB protein. In some embodiments, the antibodies disclosed herein inhibit shedding of soluble MICA protein. In some embodiments, the antibodies disclosed herein inhibit shedding of soluble MICB protein. In some embodiments, the antibodies disclosed herein inhibit shedding of both soluble MICA protein and soluble MICB protein.

Any suitable route of administration is contemplated for use with the methods disclosed herein. In some embodiments, the antibody is administered by intravenous administration. In some embodiments, the antibody is administered by subcutaneous administration. In some embodiments, the antibody is administered locally. In some embodiments, the antibody is administered systemically (e.g., intravenously, intramuscularly, subcutaneously, intradermally, orally, intranasally, sublingually). In some embodiments, the antibody is formulated as a salve, lotion or emulsion. In some embodiments, the antibody is formulated as a solution. In some embodiments, the antibody is formulated for topical, oral, buccal, or nasal administration.

In some embodiments, the individual is monitored prior to administration of the antibody. Symptoms are identified and their severity is assessed. An antibody as described herein is administered alone or in combination with additional treatments, singly or multiply over time as discussed herein or known to one of skill in the art. In some embodiments, the individual is monitored such that the efficacy of the treatment regimen is determined. In some embodiments, a treatment regimen is modified in response to preliminary treatment outcomes, such that treatment dose or frequency or dose and frequency is altered so as to attain a desired level of subject response in light of symptom alleviation, side effect reduction, or a combination of symptom alleviation and side effect reduction.

Therapeutically effective amounts or dosages are contemplated to include dosages of about 0.01 mg/kg to about 20 mg/kg, about for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2 mg/kg, about 2.1 mg/kg, about 2.2 mg/kg, about 2.3 mg/kg, about 2.4 mg/kg, about 2.5 mg/kg, about 2.6 mg/kg, about 2.7 mg/kg, about 2.8 mg/kg, about 2.9 mg/kg, about 3 mg/kg, about 3.1 mg/kg, about 3.2 mg/kg, about 3.3 mg/kg, about 3.4 mg/kg, about 3.5 mg/kg, about 3.6 mg/kg, about 3.7 mg/kg, about 3.8 mg/kg, about 3.9 mg/kg, about 4 mg/kg, about 4.1 mg/kg, about 4.2 mg/kg, about 4.3 mg/kg, about 4.4 mg/kg, about 4.5 mg/kg, about 4.6 mg/kg, about 4.7 mg/kg, about 4.8 mg/kg, about 4.9 mg/kg, about 5 mg/kg, about 5.1 mg/kg, about 5.2 mg/kg, about 5.3 mg/kg, about 5.4 mg/kg, about 5.5 mg/kg, about 5.6 mg/kg, about 5.7 mg/kg, about 5.8 mg/kg, about 5.9 mg/kg, about 6 mg/kg, about 6.1 mg/kg, about 6.2 mg/kg, about 6.3 mg/kg, about 6.4 mg/kg, about 6.5 mg/kg, about 6.6 mg/kg, about 6.7 mg/kg, about 6.8 mg/kg, about 6.9 mg/kg, about 7 mg/kg, about 7.1 mg/kg, about 7.2 mg/kg, about 7.3 mg/kg, about 7.4 mg/kg, about 7.5 mg/kg, about 7.6 mg/kg, about 7.7 mg/kg, about 7.8 mg/kg, about 7.9 mg/kg, about 8 mg/kg, about 8.1 mg/kg, about 8.2 mg/kg, about 8.3 mg/kg, about 8.4 mg/kg, about 8.5 mg/kg, about 8.6 mg/kg, about 8.7 mg/kg, about 8.8 mg/kg, about 8.9 mg/kg, about 9 mg/kg, about 9.1 mg/kg, about 9.2 mg/kg, about 9.3 mg/kg, about 9.4 mg/kg, about 9.5 mg/kg, about 9.6 mg/kg, about 9.7 mg/kg, about 9.8 mg/kg, about 9.9 mg/kg, about 10 mg/kg, about 10.1 mg/kg, about 10.2 mg/kg, about 10.3 mg/kg, about 10.4 mg/kg, about 10.5 mg/kg, about 10.6 mg/kg, about 10.7 mg/kg, about 10.8 mg/kg, about 10.9 mg/kg, about 11 mg/kg, about 11.1 mg/kg, about 11.2 mg/kg, about 11.3 mg/kg, about 11.4 mg/kg, about 11.5 mg/kg, about 11.6 mg/kg, about 11.7 mg/kg, about 11.8 mg/kg, about 11.9 mg/kg, about 12 mg/kg, about 12.1 mg/kg, about 12.2 mg/kg, about 12.3 mg/kg, about 12.4 mg/kg, about 12.5 mg/kg, about 12.6 mg/kg, about 12.7 mg/kg, about 12.8 mg/kg, about 12.9 mg/kg, about 13 mg/kg, about 13.1 mg/kg, about 13.2 mg/kg, about 13.3 mg/kg, about 13.4 mg/kg, about 13.5 mg/kg, about 13.6 mg/kg, about 13.7 mg/kg, about 13.8 mg/kg, about 13.9 mg/kg, about 14 mg/kg, about 14.1 mg/kg, about 14.2 mg/kg, about 14.3 mg/kg, about 14.4 mg/kg, about 14.5 mg/kg, about 14.6 mg/kg, about 14.7 mg/kg, about 14.8 mg/kg, about 14.9 mg/kg, about 15 mg/kg, about 15.1 mg/kg, about 15.2 mg/kg, about 15.3 mg/kg, about 15.4 mg/kg, about 15.5 mg/kg, about 15.6 mg/kg, about 15.7 mg/kg, about 15.8 mg/kg, about 15.9 mg/kg, about 16 mg/kg, about 16.1 mg/kg, about 16.2 mg/kg, about 16.3 mg/kg, about 16.4 mg/kg, about 16.5 mg/kg, about 16.6 mg/kg, about 16.7 mg/kg, about 16.8 mg/kg, about 16.9 mg/kg, about 17 mg/kg, about 17.1 mg/kg, about 17.2 mg/kg, about 17.3 mg/kg, about 17.4 mg/kg, about 17.5 mg/kg, about 17.6 mg/kg, about 17.7 mg/kg, about 17.8 mg/kg, about 17.9 mg/kg, about 18 mg/kg, about 18.1 mg/kg, about 18.2 mg/kg, about 18.3 mg/kg, about 18.4 mg/kg, about 18.5 mg/kg, about 18.6 mg/kg, about 18.7 mg/kg, about 18.8 mg/kg, about 18.9 mg/kg, about 19 mg/kg, about 19.1 mg/kg, about 19.2 mg/kg, about 19.3 mg/kg, about 19.4 mg/kg, about 19.5 mg/kg, about 19.6 mg/kg, about 19.7 mg/kg, about 19.8 mg/kg, about 19.9 mg/kg, about or 20 mg/kg, Therapeutically effective amounts or dosages, in some cases, are contemplated to include dosages of about 0.1 mg/kg to about 2.0 mg/kg, Methods of treatment herein comprise one or more administrations of anti-MICA/B antibodies in doses disclosed herein. In some embodiments, methods comprise one administration of anti-MICA/B antibodies. In some embodiments, methods comprise two administrations of anti-MICA/B antibodies. In some embodiments, methods comprise three administrations of anti-MICA/B antibodies. In some embodiments, methods comprise four administrations of anti-MICA/B antibodies. In some embodiments, methods comprise five administrations of anti-MICA/B antibodies. In some embodiments, methods comprise six administrations of anti-MICA/B antibodies. In some embodiments, one or more administrations of anti-MICA/B antibodies are administered daily. In some embodiments, one or more administrations of anti-MICA/B antibodies are administered weekly. In some embodiments, one or more administrations of anti-MICA/B antibodies are administered biweekly. In some embodiments, one or more administrations of anti-MICA/B antibodies are administered monthly. In some embodiments, one or more administrations of anti-MICA/B antibodies are administered every three months. In some embodiments, one or more administrations of anti-MICA/B antibodies are administered every six months. In some embodiments, one or more administrations of anti-MICA/B antibodies are administered yearly.

In some embodiments, the methods of treatment disclosed herein, is a monotherapy. In some embodiments, the methods of treatment disclosed herein, is a combination therapy. In some embodiments, combination therapy comprises administrations of anti-MICA/B antibodies in combination with another therapeutic agent. In some embodiments, the therapeutic agent comprises a chemotherapeutic agent. In some embodiments, the chemotherapeutic agent include, but is not limited to, cytotoxic agents, anti-metabolite agents (e.g., folate antagonists, purine analogs, pyrimidine analogs, etc.), topoisomerase inhibitors (e.g., camptothecin derivatives, anthracenedione, anthracyclines, epipodophyllotoxins, quinoline alkaloids, etc.), anti-microtubule agents (e.g., taxanes, vinca alkaloids), protein synthesis inhibitors (e.g., cephalotaxine, camptothecin derivatives, quinoline alkaloids), alkylating agents (e.g., alkyl sulfonates, ethylenimines, nitrogen mustards, nitrosoureas, platinum derivatives, triazenes, etc.), alkaloids, terpenoids, kinase inhibitors and immune checkpoint inhibitors. In some embodiments, the anti-MICA/B antibodies disclosed herein are administered in combination with a therapeutic agent that induces an immune response. In some embodiments, the anti-MICA/B antibodies disclosed herein are administered in combination with a therapeutic agent that inhibits downregulation of an immune response. In some embodiments, inducing an immune response comprises activation or upregulating activity of NK cells. In some embodiments, inducing an immune response comprises activation or upregulating activity of T cells. In some embodiments, the immune check point inhibitor target comprises PD-1. In some embodiments, the immune check point inhibitor target comprises PD-L1. In some embodiments, the immune checkpoint inhibitor comprises Pembrolizumab, Nivolumab, Cemiplimab, AMP-224, AMP-514, PDR001, Atezolizumab, Avelumab. Durvalumab, BMS-936559, and CK-301.

Pharmaceutical Compositions

Also disclosed herein are pharmaceutical compositions comprising anti-MICA/B antibodies disclosed herein and a pharmaceutically acceptable carrier or excipient.

In some embodiments, excipients for use with the compositions disclosed herein include maleic acid, tartaric acid, lactic acid, citric acid, acetic acid, sodium bicarbonate, sodium phosphate, histidine, glycine, sodium chloride, potassium chloride, calcium chloride, zinc chloride, water, dextrose, N-methylpyrrolidone, dimethyl sulfoxide, N,N-dimethylacetamide, ethanol, propylene glycol, polyethylene glycol, diethylene glycol monoethyl ether, and surfactant polyoxyethylene-sorbitan monooleate.

In some embodiments, the compositions further comprise an additional therapeutic agent. In some embodiments, the therapeutic agent is a chemotherapeutic agent. The chemotherapeutic agents can include, among others, cytotoxic agents, anti-metabolite agents (e.g., folate antagonists, purine analogs, pyrimidine analogs, etc.), topoisomerase inhibitors (e.g., camptothecin derivatives, anthracenedione, anthracyclines, epipodophyllotoxins, quinoline alkaloids, etc.), anti-microtubule agents (e.g., taxanes, vinca alkaloids), protein synthesis inhibitors (e.g., cephalotaxine, camptothecin derivatives, quinoline alkaloids), alkylating agents (e.g., alkyl sulfonates, ethylenimines, nitrogen mustards, nitrosoureas, platinum derivatives, triazenes, etc.), alkaloids, terpenoids, and kinase inhibitors.

In some embodiments, the antibody and the therapeutic agent are in the same formulation. In some embodiments, the antibody and the therapeutic agent are in different formulation. In some embodiments, antibody described herein is used prior to the administration of the other therapeutic agent. In some embodiments, antibody described herein is used concurrently with the administration of the other therapeutic agent. In some embodiments, antibody described herein is used subsequent to the administration of the other therapeutic agent.

Pharmaceutical formulations, in some embodiments, are made to be compatible with a particular local, regional or systemic administration or delivery route. Thus, pharmaceutical formulations include carriers, diluents, or excipients suitable for administration by particular routes. Specific non-limiting examples of routes of administration for compositions herein are parenteral, e.g., intravenous, intra-arterial, intradermal, intramuscular, subcutaneous, intra-pleural, transdermal (topical), transmucosal, intra-cranial, intra-spinal, intra-ocular, rectal, oral (alimentary), mucosal administration, and any other formulation suitable for the treatment method or administration protocol.

In some embodiments, solutions or suspensions used for parenteral application include: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates; and agents for the adjustment of tonicity such as sodium chloride or dextrose. In some embodiments, pH is adjusted with acids or bases, such as hydrochloric acid or sodium hydroxide.

Pharmaceutical formulations for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In some embodiments, the carrier is a solvent or dispersion medium containing, for example, water, ethanol, polyol (for example, glycerol, propylene glycol, and liquid polyetheylene glycol, and the like), or suitable mixtures thereof. Fluidity is maintained, in some embodiments, for example, by the use of a coating such as lecithin, by the maintenance of the required particle size in the case of dispersion, and by the use of surfactants. Antibacterial and antifungal agents include, for example, parabens, chlorobutanol, phenol, ascorbic acid, and thimerosal. Isotonic agents, for example, sugars; polyalcohols such as mannitol or sorbitol: or sodium chloride, in some embodiments, are included in the composition. In some cases, also included is an agent which delays absorption, in some embodiments, for example, aluminum monostearate or gelatin prolongs absorption of injectable compositions.

In some embodiments, sterile injectable formulations are prepared by incorporating the active composition in the required amount in an appropriate solvent with one or a combination of above ingredients. Generally, dispersions are prepared by incorporating the active composition into a sterile vehicle containing a basic dispersion medium and any other ingredient. In the case of sterile powders for the preparation of sterile injectable solutions, methods of preparation include, for example, vacuum drying and freeze-drying which yields a powder of the active ingredient plus any additional desired ingredient from a previously prepared solution thereof.

For transmucosal or transdermal administration, penetrants appropriate to the barrier to be permeated are used in the formulation. Such penetrants are known in the art, and include, for example, for transmucosal administration, detergents, bile salts, and fusidic acid derivatives. In some embodiments, transmucosal administration is accomplished through the use of nasal sprays, inhalation devices (e.g., aspirators) or suppositories. For transdermal administration, the active compounds are formulated into ointments, salves, gels, creams or patches.

In some embodiments, the pharmaceutical formulations are prepared with carriers that protect against rapid elimination from the body, such as a controlled release formulation or a time delay material such as glyceryl monostearate or glyceryl stearate. The formulations, in some embodiments, are also delivered using articles of manufacture such as implants and microencapsulated delivery systems to achieve local, regional or systemic delivery or controlled or sustained release.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1. Antibody Binding Kinetics Measurement

Affinity kinetics was determined on a ForteBio Octet Red96 analyzer. Briefly, anti-MICA/B mAb (30 µg/ml) was captured on Dip and Read™ Anti-mouse IgG Fc Capture (AMC) Biosensors (ForteBio) at room temperature in an assay buffer of PBS+0.1% BSA+0.02% Tween-20 (pH 7.2). Sensors were washed in assay buffer and then incubated with purified 6×His-MICA*08 or 6×His-MICA*04 proteins (100 nM), in 2-fold dilution series for 5 minutes in assay buffer to determine association kinetics of the antibody with the protein antigen. Sensors were then incubated in assay buffer for 10 minutes to determine dissociation kinetics. The resulting kinetics parameters were calculated with ForteBio analysis suite 8.0 using a 1:1 model. Results for these assays are shown in Table 2.

TABLE 2

Kinetic measurements of anti-MICA/B antibodies to MICA antigen by BioLayer Interferometry.

| Antibody | KD (M) | kon (1/Ms) | kdis(1/s) |
|---|---|---|---|
| 3F9.E4 | 1.18E−09 | 3.83E+05 | 4.21E−04 |
| 16F10.C12 | 6.45E−09 | 9.33E+04 | 5.48E−04 |

Example 2. Antibody Binding to MICA/B Alleles

Figure 1B:
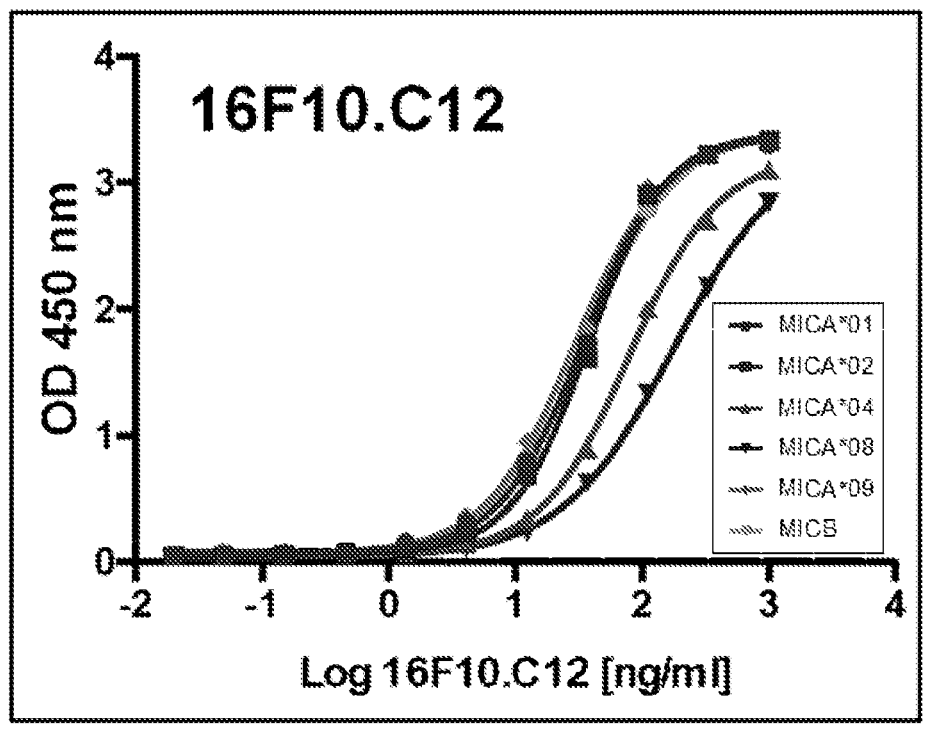

Recombinant MICA*01, MICA*02, MICA*04, MICA*OS, MICA*09, and MICB proteins were diluted to 1 µg/ml in 50 mM sodium carbonate buffer, pH 9.6, and coated onto high binding 96-well microplates (Corning #9018), 100 ng in 100 ul per well. The following morning, coated ELISA plates were washed three times with TBS-Tween-20, pH 7.4 and then blocked in SuperBlock T20 Blocking Buffer (Pierce #37536). After blocking, ELISA plates were washed once with TBS-T and incubated with serially diluted anti-MICA antibody (0-1 µg/ml) for approximately two hours at room temperature. Following the incubation. ELISA plates were washed three times with TBS-T and then incubated with Goat anti-Mouse IgG (H+L)-HRP conjugate (ThermoFisher Scientific #626520) for 45 minutes at room temperature with shaking (~400 rpm). After the incubation, ELISA plates were washed three times with TBS-T and incubated with Super Sensitive Liquid Substrate TMB (Sigma #T4444), 100 ul per well, until color development was sufficient. The reaction was stopped with IN sulfuric acid, 100 ul per well. Optical density (OD) values were measured at 450 nm using a microplate reader. The results of this assay are shown in FIG. 1A-FIG. 1B.

Example 3. Antibody Binding to Cell Surface MICA

Figures 2, 3:
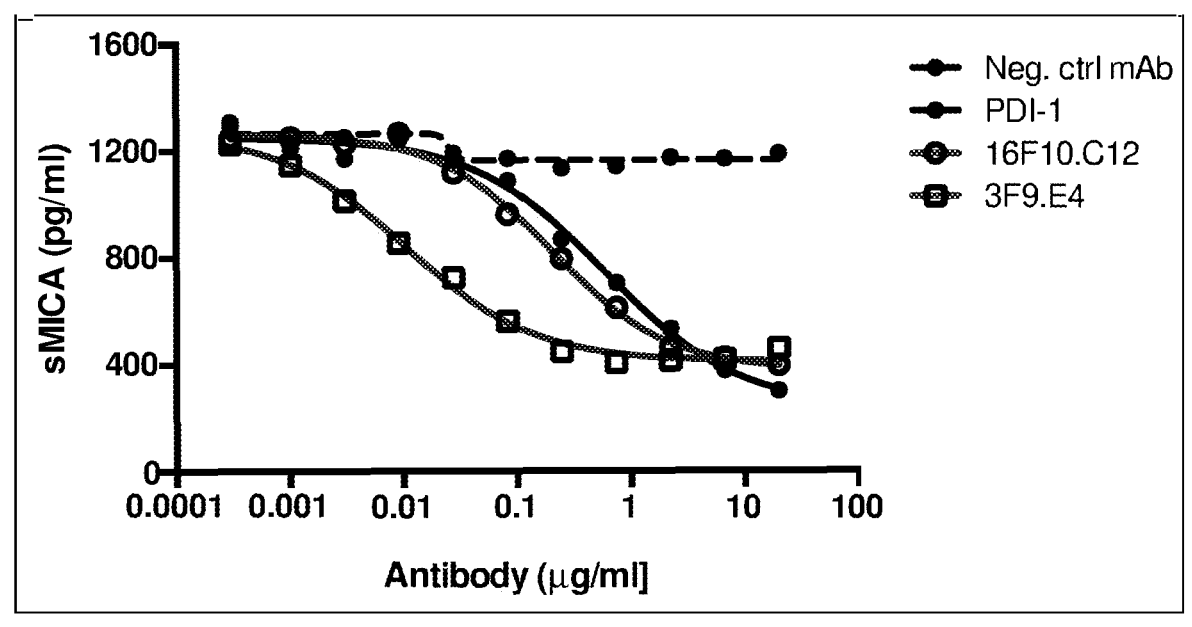
FIG. 2 exemplifies antibody 3F9.E4 binds to the cell surface MICA, evaluated by staining of TRAMP C2 cells transfected with MICA*08 in comparison to parental TC2 cells.
FIG. 3 exemplifies antibodies 3F9.E4 and 16F10.C12 inhibit MICA shedding from PLC/PRF/5 cells.

Mouse prostate adenocarcinoma TRAMP-C2 cells (TC2) (ATCC, Manassas, Va.) were used to generate a stable cell line expressing MICA*08 allele (TC2-MICA-08). Binding of anti-MICA antibody to TC2-MICA-08 was analyzed by flow cytometry. Briefly, cells were first stained with LIVE/DEAD Near IR Stain (Thermo) for 30 min at 4° C., and then washed once by centrifugation with FACS Buffer (1 mM EDTA, 25 mM HEPES, 2% FBS in 1×PBS). About 2–3×10$^5$ TC2-MICA-08 cells were incubated with 100 µl of FACS Buffer containing 500 ng anti-MICA antibody at 4° C. for 30 min, followed by incubation with 100 ul 2 g/ml PE conjugated goat-anti-mouse IgG (Biolegend, San Diego, Calif.) secondary Ab at 4° C. for 30 min. Cells were then washed once and cell pellet resuspended with FACS Buffer for FACS analysis gated on live cells. Significantly higher PE fluorescence signal was observed with TC2-MICA-08 cells compared to parental TC2 cells indicated binding of anti-MICA mAb to surface expressed MICA. Result for this assay is shown in FIG. 2.

Example 4. Antibody Inhibits MICA Shedding from PLC/PRF/5 Cells

4×10$^4$ PLC/PRF/5 cells (Hepatocellular Carcinoma) (ATCC, Manassas, Va.) were plated in 96-well plate and incubated at 37° C. overnight. Cells were then treated with 100 ul Complete Media (MEM+10% FBS. Thermo, Grand Island, N.Y.) containing anti-MICA antibody that binds to MICA α3 domain and negative control antibodies, respectively, and incubated at 37° C. for another day. Cell supernatants containing shed MICA were used to determine the level of soluble MICA by ELISA. Briefly, 96-well plate was coated with 100 µl 2 µg/ml anti-human MICA/B (clone BAMO1, MBL, Japan) overnight at 4° C. Plate was blocked and then incubated with cell supernatants and MICA standards for 2 hours. After incubation, plates were washed and followed by 1 hour incubation with 1 µg/ml proprietary anti-human MICA/MICB mAb, clone 10E9 conjugated with biotin. Next. 100 ul HRP conjugated streptavidin (HRP-SA) (R&D Systems, Minneapolis, Minn.) was added to wells and incubated for 30 min Samples were developed with TMB for 4 min, stopped with IN sulfuric acid and detected with absorbance at 450 nm. Soluble MICA level was interpolated from standard curve. Result for this assay is shown in FIG. 3.

Figure 4A:
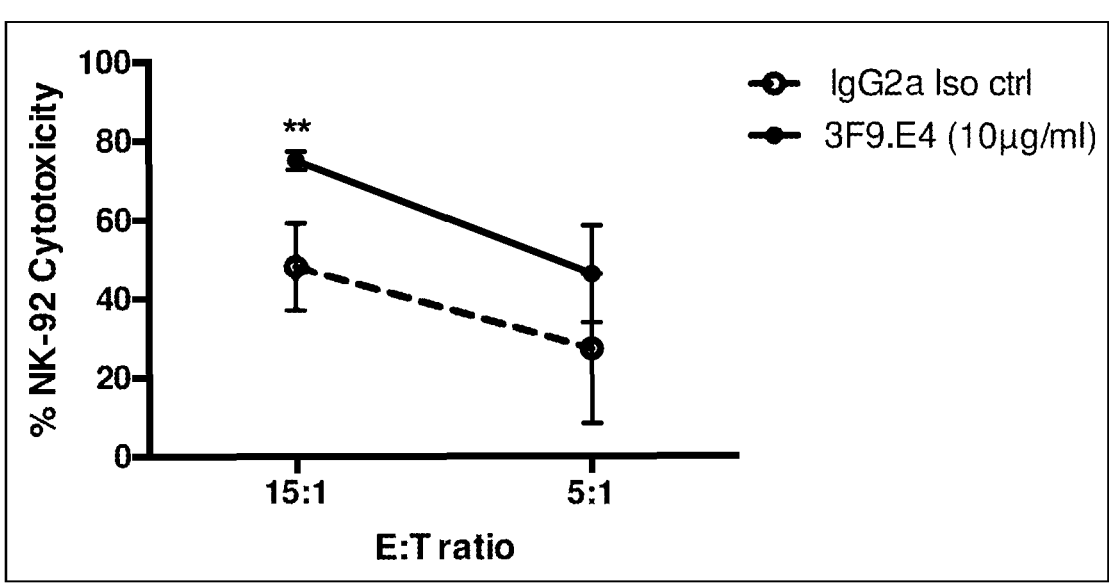
FIG. 4A-FIG. 4B exemplifies antibodies 3F9.E4 (FIG. 4A) and 16F10.C12 (FIG. 4B) enhance NK-92 cells mediated cytotoxicity of PLC/PRF/5 cells.
Figure 4B:
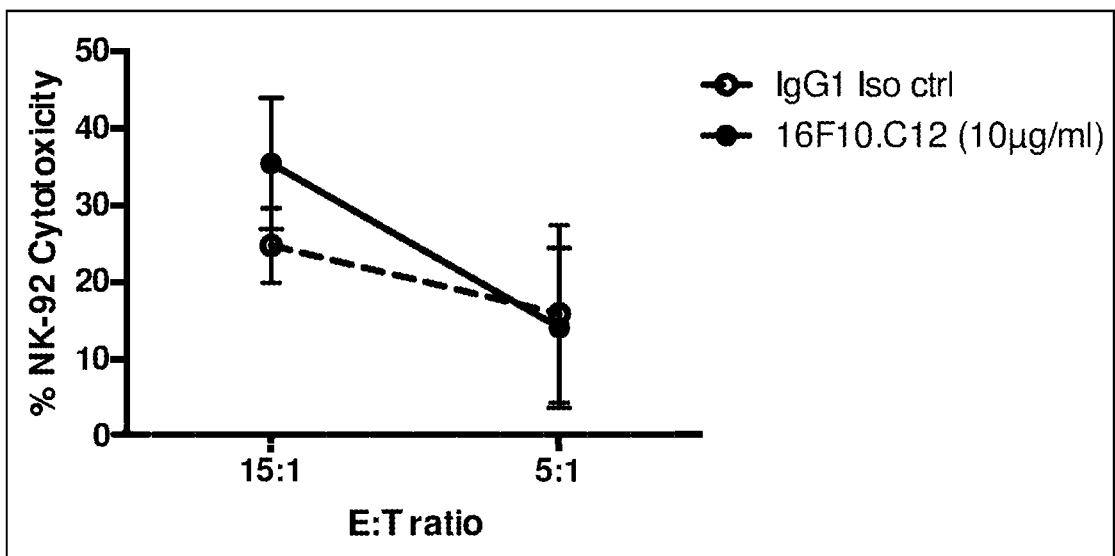

Example 5. Antibody Enhances NK-92 Cells Mediated Cytotoxicity to PLC/PRF/5 Cells PLC/PRF/5 (Target) cells were suspended in RPMI-1640 with 10% FBS, and plated into 96-well flat bottom plates (Costar) at 6000 cells/well. Cells were then incubated with anti-MICA antibody (10 µg/ml) that binds to MICA α3 domain for 24 hours before being labeled with calcein AM (1 µM) for 3 hours at 37° C., 5% $CO_2$. Wells were washed, and NK-92 cells (Effector) suspended in RPMI-1640 with 10% FBS were then added to wells at various Effector-to-Target (E:T) ratios as indicated and co-cultured with target cells for 4 hours. At the end of the cultures, the supernatant was removed, replaced with PBS, and the calcein AM signal was measured using a VICTOR Multilabel plate reader (Perkin Elmer). An isotype matched nonreactive immunoglobulin (R&D) antibody was used as a control. Results for this assay are shown in FIG. 4A-FIG. 4B.

Figure 5:
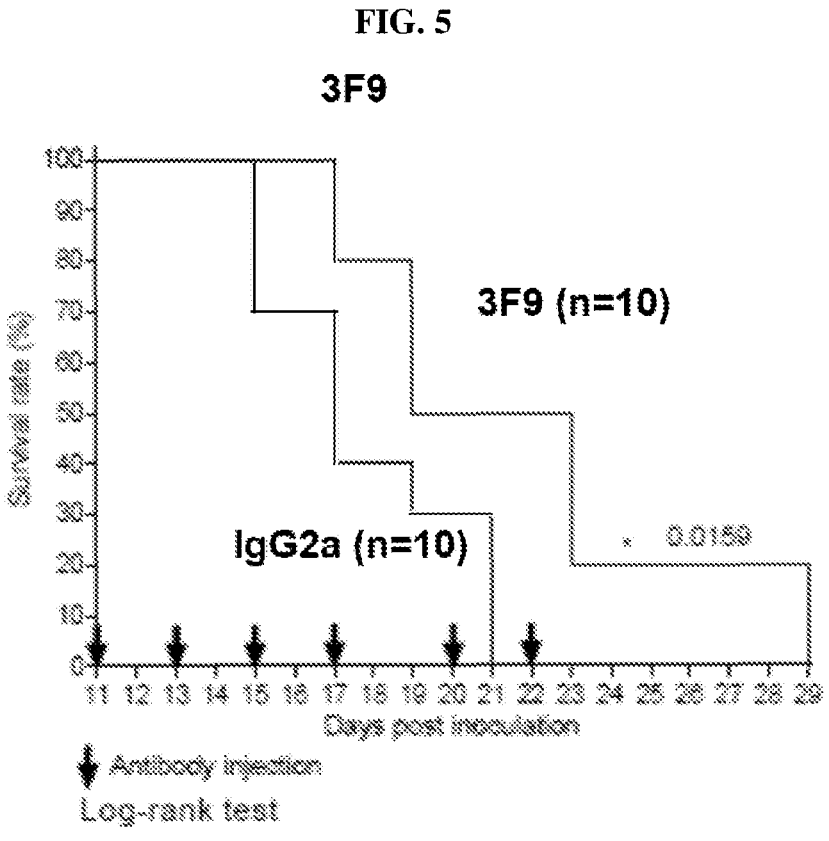
FIG. 5 exemplifies antitumor activity of antibody 3F9 against B16/MICA transfectants relative to isotype control (IC).

Example 6. Efficacy of 3F9.E4 in Tumor Therapy In Vivo (Survival) and NKG2S Expression by Tumor-Infiltrating Lymphocytes in Tumor-Bearing Mice MICA transgenic mice (MICAgen) were inoculated with $10^4$B16F10-MICA*01 cells (B16 transfectant) and, upon day 11, when tumors reached the desired threshold size, mice were treated with 3F9.E4 or isotype control (arrows indicate days of injection) (Log-rank test). Results are shown in FIG. 5.

Figure 6A:
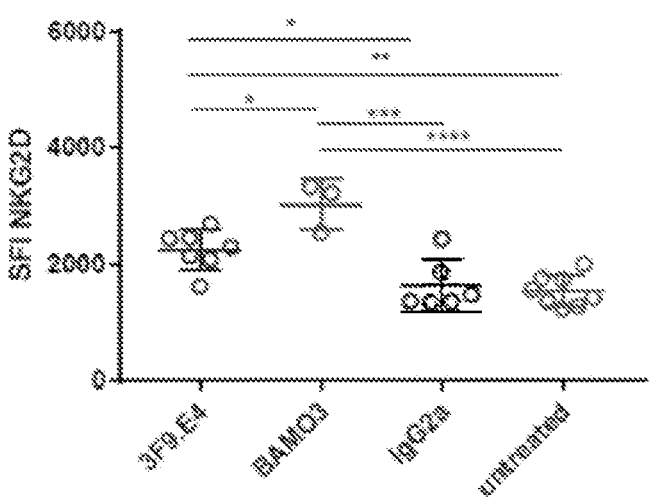
FIG. 6A-FIG. 6C exemplify higher percentage of NKG2D positive NK cells (FIG. 6A), CD8+ T cells (FIG. 6B) and gamma delta T cells (FIG. 6C) are observed in tumor infiltrates (TILs) in 3F9 antibody treated tumors compared to isotype control.
Figure 6B:
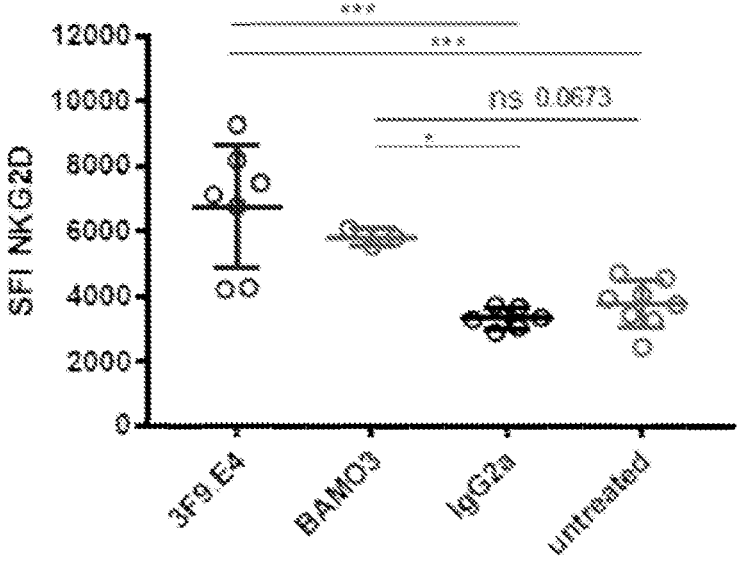
Figure 6C:
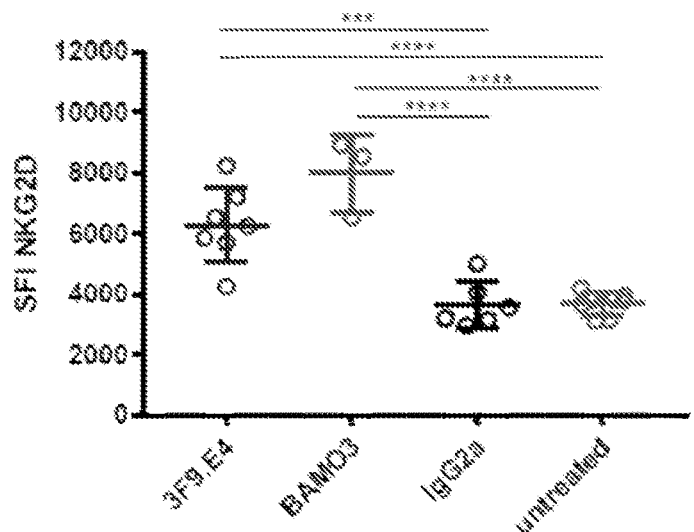

Mice were sacrificed when reaching a high tumor load and tumor-infiltrating lymphocytes analyzed for NKG2D expression (SFI) by NK cells, CD8 αβ T cells, and γδ T cells. NKG2D expression strength (SFI) of NKG2D-expressing cells are shown in FIG. 6A-FIG. 6C. Each symbol represents analyses of an individual mouse. (One-way ANOVA+Tukey's multiple comparisons test).

Figure 7A:
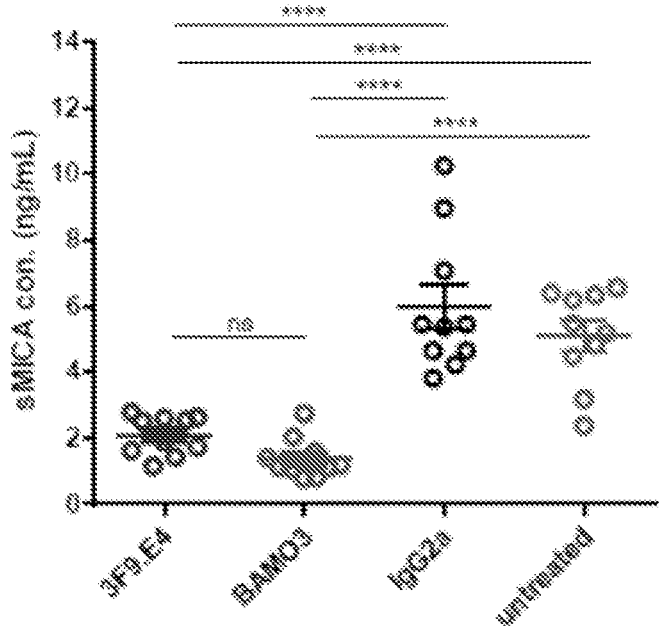
FIG. 7A-FIG. 7B exemplify treatment with 3F9 antibody in B16/MICA in MICA transgenic animals reduces levels of soluble MICA (FIG. 7A) and surface MICA in tumors (FIG. 7B).
Figure 7B:
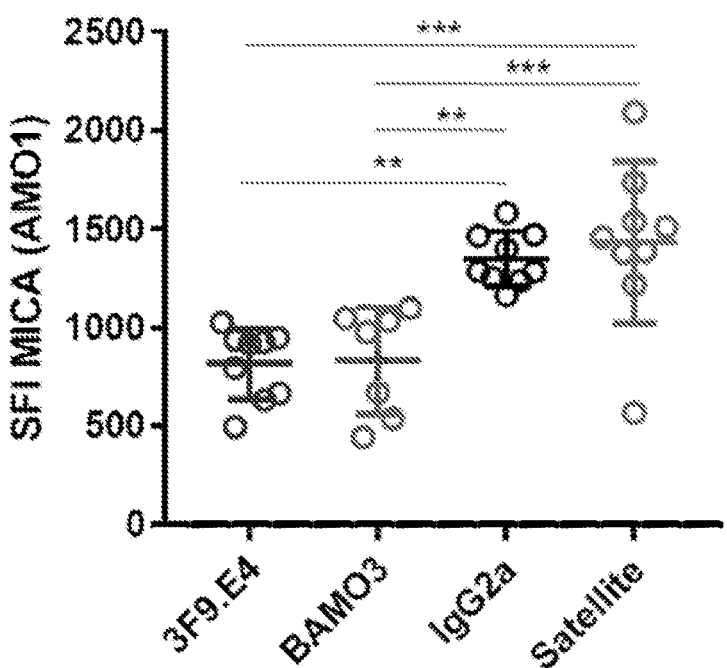

Example 7. MICA Expression by B16 Transfectant Tumors Ex Vivo and Detection of Soluble MICA in Sera of Tumor-Bearing Mice MICA transgenic mice (MICAgen) were inoculated with $10^4$B16F10-MICA*01 cells (B16 transfectant) and, upon day 11, when tumors reached the desired threshold size, mice were treated with 3F9.E4 or BAMO3 or isotype control. Mice were sacrificed when reaching a high tumor load and isolated single tumor cells analyzed for MICA expression with mAb AMO1 staining (One-way ANOVA+ Tukey's multiple comparisons test). AMO1 binds to the a1a2-domain of MICA (≠BAMO3 and 3F9). Each symbol represents analysis of an individual mouse. Results are shown in FIG. 7B. Sera was also analyzed for sMICA using AMO1/BAMO1 sandwich ELISA. Each symbol represents an individual mouse (Unpaired t-test). Results are shown in FIG. 7A.

Example 8. Epitope Binning

Figure 8A:
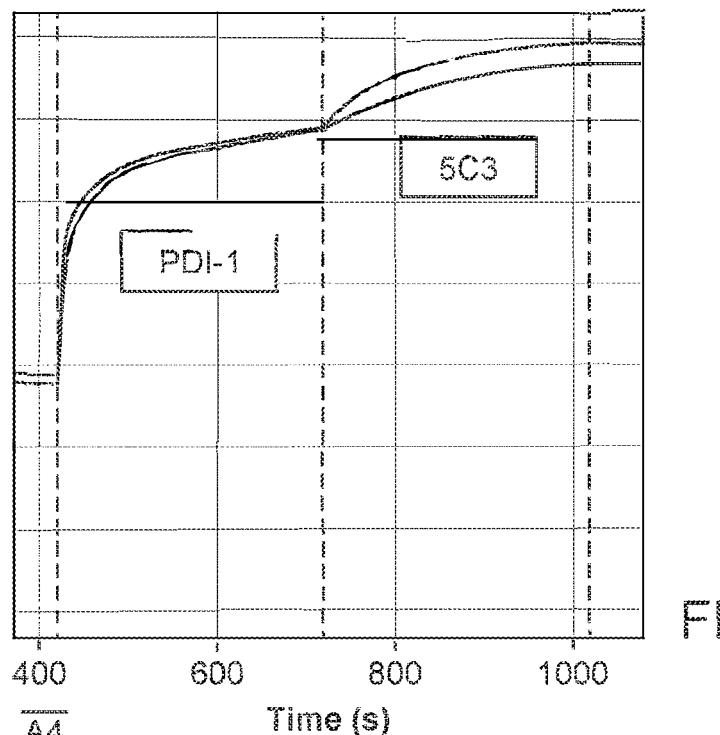
FIG. 8A-FIG. 8C exemplify competition binding assay to illustrate that all antibodies bind to a "structural" epitope and antibody 3F9.E4 competitively binds antibody PDI-1 (FIG. 8B) and antibody 16F10 binds a slightly different epitope than PDI-1 and 3F9, but in close proximity (FIG. 8C).
Figure 8B:
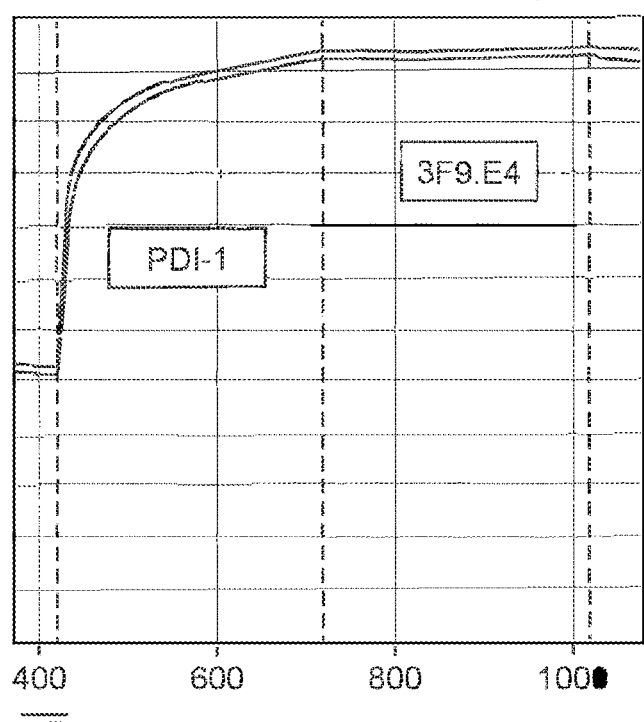
Figure 8C:
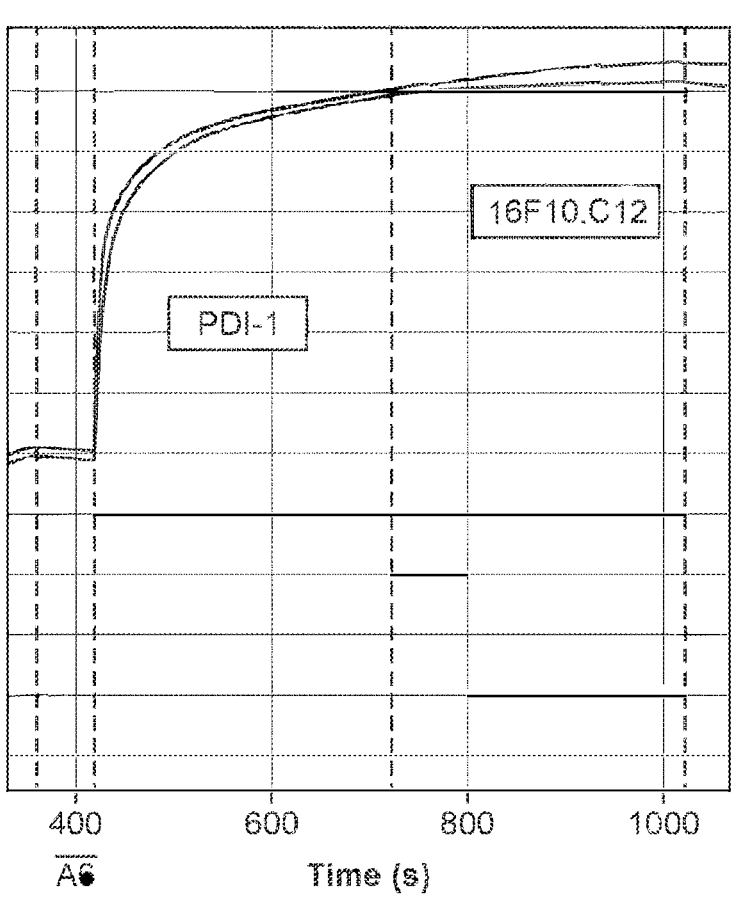

MICA*04-His protein (30 ng/ml) was immobilized onto Ni-NTA (FortrBio, #18-5101) biosensor tips for a biolayer interferometry instrument (Octet Red, ForteBio) for 300 s. The baseline signal was measured again for 60 s before biosensor tips were immersed into wells containing 1 mM or 0.5 mM of primary antibody for 300 s. Following this process, biosensors were immersed into wells containing 100 nM or 50 nM of a second mAb for 300 s. Percent binding of a second mAbs in the presence of the first mAb was determined by comparing the maximal signal of the second mAb after the first mAb was added to the maximum signal of the second mAb alone. mAbs were considered noncompeting if maximum binding of the second mAb was ≥66% of its uncompleted binding. A level between 33% and 66% of its uncompleted binding was considered intermediate competition, and ≤33% was considered competing. Results for this assay are shown in FIG. 8A-FIG. 8C.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments described herein may be employed. It is intended that the following claims define the scope of the invention and that methods and structures within the scope of these claims and their equivalents be covered thereby.

---

SEQUENCE LISTING

```
Sequence total quantity: 34
SEQ ID NO: 1            moltype = AA  length = 16
FEATURE                Location/Qualifiers
REGION                 1..16
                       note = Description of Artificial Sequence: Synthetic peptide
source                 1..16
                       mol_type = protein
                       organism = synthetic construct
SEQUENCE: 1
RSSKSLLHSN GNTYLY                                                    16

SEQ ID NO: 2            moltype = AA  length = 7
FEATURE                Location/Qualifiers
REGION                 1..7
                       note = Description of Artificial Sequence: Synthetic peptide
source                 1..7
                       mol_type = protein
                       organism = synthetic construct
SEQUENCE: 2
RMSNLAS                                                              7
```

-continued

```
SEQ ID NO: 3             moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 3
MQHLEYPFT                                                           9

SEQ ID NO: 4             moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 4
GFTFSNYAMS                                                          10

SEQ ID NO: 5             moltype = AA  length = 17
FEATURE                  Location/Qualifiers
REGION                   1..17
                         note = Description of Artificial Sequence: Synthetic peptide
source                   1..17
                         mol_type = protein
                         organism = synthetic construct
SEQUENCE: 5
YISPGGDYIY YADTVKG                                                  17

SEQ ID NO: 6             moltype = AA  length = 12
FEATURE                  Location/Qualifiers
REGION                   1..12
                         note = Description of Artificial Sequence: Synthetic peptide
source                   1..12
                         mol_type = protein
                         organism = synthetic construct
SEQUENCE: 6
DRRHYGSYAM DY                                                       12

SEQ ID NO: 7             moltype = AA  length = 112
FEATURE                  Location/Qualifiers
REGION                   1..112
                         note = Description of Artificial Sequence: Synthetic
                          polypeptide
source                   1..112
                         mol_type = protein
                         organism = synthetic construct
SEQUENCE: 7
DIVMTQAAPS VPVTPGESVS ISCRSSKSLL HSNGNTYLYW FLQRPGQSPQ LLIYRMSNLA  60
SGVPDRFSGS GSGTAFTLRI SRVEAEDVGV YYCMQHLEYP FTFGSGTKLE IK          112

SEQ ID NO: 8             moltype = AA  length = 121
FEATURE                  Location/Qualifiers
REGION                   1..121
                         note = Description of Artificial Sequence: Synthetic
                          polypeptide
source                   1..121
                         mol_type = protein
                         organism = synthetic construct
SEQUENCE: 8
EVQLQESGEG LVKPGGSLKL SCAASGFTFS NYAMSWVRQT PEKRLEWVAY ISPGGDYIYY  60
ADTVKGRFTI SRDNARNTLY LQMSSLKSED TAMYYCTTDR RHYGSYAMDY WGQGISVTVS  120
S                                                                  121

SEQ ID NO: 9             moltype = AA  length = 12
FEATURE                  Location/Qualifiers
REGION                   1..12
                         note = Description of Artificial Sequence: Synthetic peptide
source                   1..12
                         mol_type = protein
                         organism = synthetic construct
SEQUENCE: 9
TASSSVSSNY LH                                                       12

SEQ ID NO: 10            moltype = AA  length = 7
FEATURE                  Location/Qualifiers
REGION                   1..7
```

```
                         note = Description of Artificial Sequence: Synthetic peptide
source                   1..7
                         mol_type = protein
                         organism = synthetic construct
SEQUENCE: 10
TTSNLAS                                                              7

SEQ ID NO: 11            moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 11
HQFHRSPFT                                                            9

SEQ ID NO: 12            moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 12
GFSLTAFGVN                                                           10

SEQ ID NO: 13            moltype = AA  length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 13
MIWGDGNTDY NSTLRS                                                    16

SEQ ID NO: 14            moltype = AA  length = 12
FEATURE                  Location/Qualifiers
REGION                   1..12
                         note = Description of Artificial Sequence: Synthetic peptide
source                   1..12
                         mol_type = protein
                         organism = synthetic construct
SEQUENCE: 14
ETYYGNYAGL GY                                                        12

SEQ ID NO: 15            moltype = AA  length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 15
QIVLTQSPAI MSASIGERVT MTCTASSSVS SNYLHWYQQK PRSSPKLWIY TTSNLASGVP  60
TRFSGSGSGT SYSLTISSME AEDAATYYCH QFHRSPFTFG SGTKLEIK               108

SEQ ID NO: 16            moltype = AA  length = 120
FEATURE                  Location/Qualifiers
REGION                   1..120
                         note = Description of Artificial Sequence: Synthetic
                          polypeptide
source                   1..120
                         mol_type = protein
                         organism = synthetic construct
SEQUENCE: 16
EVQLQESGPG LVAPSQSLSI TCTVSGFSLT AFGVNWVRQP PGKGLEWLGM IWGDGNTDYN  60
STLRSRLSIS KDNSKSQVFL KLNSLQTDDT ARYFCARETY YGNYAGLGYW GQGTLVTVSA  120

SEQ ID NO: 17            moltype = AA  length = 16
FEATURE                  Location/Qualifiers
REGION                   1..16
                         note = Description of Artificial Sequence: Synthetic peptide
source                   1..16
                         mol_type = protein
                         organism = synthetic construct
SEQUENCE: 17
```

-continued

```
RSSKSLLHSN LNTYLY                                                16

SEQ ID NO: 18          moltype = AA   length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 18
YISPGGDYIY YADSVKG                                               17

SEQ ID NO: 19          moltype = AA   length = 113
FEATURE                Location/Qualifiers
REGION                 1..113
                       note = Description of Artificial Sequence: Synthetic
                        polypeptide
source                 1..113
                       mol_type = protein
                       organism = synthetic construct
SEQUENCE: 19
DIVMTQSPLS LPVTPGEPAS ISCRSSKSLL HSNLNTYLYW FLQKPGQSPQ ILIYRMSNLA  60
SGVPDRFSGS GSGTAFTLKI SRVEAEDVGV YYCMQHLEYP FTFGPGTKLE IKR        113

SEQ ID NO: 20          moltype = AA   length = 98
FEATURE                Location/Qualifiers
REGION                 1..98
                       note = Description of Artificial Sequence: Synthetic
                        polypeptide
source                 1..98
                       mol_type = protein
                       organism = synthetic construct
SEQUENCE: 20
QVQLVESGGG LVKPGGSLRL SCAASGFTFS NYAMSWIRQA PGKGLEWVSY ISPGGDYIYY  60
ADSVKGRFTI SRDNAKNSLY LQMNSLRAED TAVYYCTT                         98

SEQ ID NO: 21          moltype = AA   length = 219
FEATURE                Location/Qualifiers
REGION                 1..219
                       note = Description of Artificial Sequence: Synthetic
                        polypeptide
source                 1..219
                       mol_type = protein
                       organism = synthetic construct
SEQUENCE: 21
DIVMTQSPLS LPVTPGEPAS ISCRSSKSLL HSNLNTYLYW FLQKPGQSPQ ILIYRMSNLA  60
SGVPDRFSGS GSGTAFTLKI SRVEAEDVGV YYCMQHLEYP FTFGPGTKLE IKRTVAAPSV 120
FIFPPSDEQL KSGTASVVCL LNNFYPREAK VQWKVDNALQ SGNSQESVTE QDSKDSTYSL 180
SSTLTLSKAD YEKHKVYACE VTHQGLSSPV TKSFNRGEC                        219

SEQ ID NO: 22          moltype = AA   length = 450
FEATURE                Location/Qualifiers
REGION                 1..450
                       note = Description of Artificial Sequence: Synthetic
                        polypeptide
source                 1..450
                       mol_type = protein
                       organism = synthetic construct
SEQUENCE: 22
QVQLVESGGG LVKPGGSLRL SCAASGFTFS NYAMSWIRQA PGKGLEWVSY ISPGGDYIYY  60
ADSVKGRFTI SRDNAKNSLY LQMNSLRAED TAVYYCTTDR RHYGSYAMDY WGQGTLVTVS 120
SASTKGPSVF PLAPSSKSTS GGTAALGCLV KDYFPEPVTV SWNSGALTSG VHTFPAVLQS 180
SGLYSLSSVV TVPSSSLGTQ TYICNVNHKP SNTKVDKKVE PKSCDKTHTC PPCPAPELLG 240
GPSVFLFPPK PKDTLMISRT PEVTCVVVDV SHEDPEVKFN WYVDGVEVHN AKTKPREEQY 300
NSTYRVVSVL TVLHQDWLNG KEYKCKVSNK ALPAPIEKTI SKAKGQPREP QVYTLPPSRE 360
EMTKNQVSLT CLVKGFYPSD IAVEWESNGQ PENNYKTTPP VLDSDGSFFL YSKLTVDKSR 420
WQQGNVFSCS VMHEALHNHY TQKSLSLSPG                                  450

SEQ ID NO: 23          moltype = AA   length = 234
FEATURE                Location/Qualifiers
REGION                 1..234
                       note = Description of Artificial Sequence: Synthetic
                        polypeptide
source                 1..234
                       mol_type = protein
                       organism = synthetic construct
SEQUENCE: 23
METDTLLLWV LLLWVPGSTG DIQMTQSPST LSASVGDRVT ITCSASQGIS NYLNWYQQKP  60
GKAPKLLIQY TSLLHSGVPS RFSGSGSGTE YTLTISSLQP DDFATYFCQQ YSKFPRTFGG 120
```

```
GTKVEIKRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGEC          234

SEQ ID NO: 24            moltype = AA  length = 234
FEATURE                  Location/Qualifiers
REGION                   1..234
                         note = Description of Artificial Sequence: Synthetic
                          polypeptide
source                   1..234
                         mol_type = protein
                         organism = synthetic construct
SEQUENCE: 24
METDTLLLWV LLLWVPGSTG DIQMTQSPSS LSASVGDRVT ITCSASQGIS NYLNWYQQKP   60
GKAPKLLIQY TSLLHSGVPS RFSGSGSGTD YTLTISSLQP EDFATYFCQQ YSKFPRTFGG   120
GTKVEIKRTV AAPSVFIFPP SDEQLKSGTA SVVCLLNNFY PREAKVQWKV DNALQSGNSQ   180
ESVTEQDSKD STYSLSSTLT LSKADYEKHK VYACEVTHQG LSSPVTKSFN RGEC          234

SEQ ID NO: 25            moltype = AA  length = 471
FEATURE                  Location/Qualifiers
REGION                   1..471
                         note = Description of Artificial Sequence: Synthetic
                          polypeptide
source                   1..471
                         mol_type = protein
                         organism = synthetic construct
SEQUENCE: 25
MDPKGSLSWR ILLFLSLAFE LSYGQIQLVQ SGSELKKPGA SVKVSCKAFG YTFTNYGMNW   60
VKQAPGQGLK WMGWINTYTG EPTYAQGFTG RFVFSLETSV STAYLQISSL KAEDTAVYFC   120
ARNYGNYLFD YWGQGTLVTV SSASTKGPSV FPLAPSSKST SGGTAALGCL VKDYFPEPVT   180
VSWNSGALTS GVHTFPAVLQ SSGLYSLSSV VTVPSSSLGT QTYICNVNHK PSNTKVDKKV   240
EPKSCDKTHT CPPCPAPELL GGPSVFLFPP KPKDTLMISR TPEVTCVVVD VSHEDPEVKF   300
NWYVDGVEVH NAKTKPREEQ YNSTYRVVSV LTVLHQDWLN GKEYKCKVSN KALPAPIEKT   360
ISKAKGQPRE PQVYTLPPSR EEMTKNQVSL TCLVKGFYPS DIAVEWESNG QPENNYKTTP   420
PVLDSDGSFF LYSKLTVDKS RWQQGNVFSC SVMHEALHNH YTQKSLSLSP G            471

SEQ ID NO: 26            moltype = AA  length = 471
FEATURE                  Location/Qualifiers
REGION                   1..471
                         note = Description of Artificial Sequence: Synthetic
                          polypeptide
source                   1..471
                         mol_type = protein
                         organism = synthetic construct
SEQUENCE: 26
MDPKGSLSWR ILLFLSLAFE LSYGQIQLVQ SGAEVKKPGA SVKVSCKAFG YTFTNYGMNW   60
VKQAPGQGLK WMGWINTYTG EPTYADDFKG RVTFTLETSI STAYMELSRL RSDDTAVYFC   120
ARNYGNYLFD YWGQGTLVTV SSASTKGPSV FPLAPSSKST SGGTAALGCL VKDYFPEPVT   180
VSWNSGALTS GVHTFPAVLQ SSGLYSLSSV VTVPSSSLGT QTYICNVNHK PSNTKVDKKV   240
EPKSCDKTHT CPPCPAPELL GGPSVFLFPP KPKDTLMISR TPEVTCVVVD VSHEDPEVKF   300
NWYVDGVEVH NAKTKPREEQ YNSTYRVVSV LTVLHQDWLN GKEYKCKVSN KALPAPIEKT   360
ISKAKGQPRE PQVYTLPPSR EEMTKNQVSL TCLVKGFYPS DIAVEWESNG QPENNYKTTP   420
PVLDSDGSFF LYSKLTVDKS RWQQGNVFSC SVMHEALHNH YTQKSLSLSP G            471

SEQ ID NO: 27            moltype = AA  length = 108
FEATURE                  Location/Qualifiers
REGION                   1..108
                         note = Description of Artificial Sequence: Synthetic
                          polypeptide
source                   1..108
                         mol_type = protein
                         organism = synthetic construct
SEQUENCE: 27
DIQMTQTTSS LSASLGDRVT ISCSASQGIS NYLNWYQQKP DGTLKLLIQY TSLLHSGVPS   60
RFSGSGSGTE YSLTISNLEP EDIATYFCQQ YSKFPRTFGG GTKLEIKR                108

SEQ ID NO: 28            moltype = AA  length = 118
FEATURE                  Location/Qualifiers
REGION                   1..118
                         note = Description of Artificial Sequence: Synthetic
                          polypeptide
source                   1..118
                         mol_type = protein
                         organism = synthetic construct
SEQUENCE: 28
QIQLVQSGPE LKKSGETVKI SCKAFGYTFT NYGMNWVKQA PGKGLKWMGW INTYTGEPTY   60
ADDFKGRFAF SLETSASTAY LQINHLKNED TATYFCARNY GNYLFDYWGQ GTTLTVSS     118

SEQ ID NO: 29            moltype = AA  length = 11
FEATURE                  Location/Qualifiers
```

-continued

```
REGION                  1..11
                        note = Description of Artificial Sequence: Synthetic peptide
source                  1..11
                        mol_type = protein
                        organism = synthetic construct
SEQUENCE: 29
SASQGISNYL N                                                        11

SEQ ID NO: 30           moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 30
TSLLHSG                                                             7

SEQ ID NO: 31           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 31
QQYSKFPRT                                                           9

SEQ ID NO: 32           moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 32
GYTFTNYGMN                                                          10

SEQ ID NO: 33           moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 33
INTYTGEPTY ADDFKG                                                   16

SEQ ID NO: 34           moltype = AA  length = 9
FEATURE                 Location/Qualifiers
REGION                  1..9
                        note = Description of Artificial Sequence: Synthetic peptide
source                  1..9
                        mol_type = protein
                        organism = synthetic construct
SEQUENCE: 34
NYGNYLFDY                                                           9
```

The invention claimed is:

1. A monoclonal antibody or an antigen-binding fragment thereof, wherein the monoclonal antibody or antigen binding fragment thereof specifically binds to a MICA protein, a MICB protein, or both MICA and MICB, comprising
   a. A light chain variable domain (VL) comprising an amino acid sequence 100% identical to SEQ ID NO: 7 and a heavy chain variable domain (VH) comprising an amino acid sequence 100% identical to SEQ ID NO: 8; or
   b. A VL comprising an amino acid sequence 100% identical to SEQ ID NO: 15 and a heavy chain variable domain (VH) comprising an amino acid sequence 100% identical to SEQ ID NO: 16.

2. The monoclonal antibody of claim 1, wherein the monoclonal antibody or antigen binding fragment thereof is selected from a whole immunoglobulin, an scFv, a Fab, a F(ab')2, or a disulfide linked Fv.

3. The monoclonal antibody of claim 1, wherein the monoclonal antibody or antigen binding fragment thereof is an IgG or IgM.

4. The monoclonal antibody of claim 1, wherein the monoclonal antibody or antigen binding fragment thereof is humanized or chimeric.

* * * * *